US008386184B2

(12) United States Patent
Bartkowiak et al.

(10) Patent No.: US 8,386,184 B2
(45) Date of Patent: Feb. 26, 2013

(54) SYSTEMS AND METHODS FOR DETERMINING AN AMOUNT OF STARTING REAGENT USING THE POLYMERASE CHAIN REACTION

(75) Inventors: Miroslaw Bartkowiak, Raleigh, NC (US); Richard L. Moore, Glenville, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 981 days.

(21) Appl. No.: 12/196,339

(22) Filed: Aug. 22, 2008

(65) Prior Publication Data

US 2009/0068666 A1    Mar. 12, 2009

Related U.S. Application Data

(60) Provisional application No. 60/968,466, filed on Aug. 28, 2007.

(51) Int. Cl.
*G06F 19/00* (2011.01)
*C12Q 1/68* (2006.01)
*C12P 19/34* (2006.01)

(52) U.S. Cl. ............................ 702/19; 435/6.1; 435/91.2
(58) Field of Classification Search .................. None
See application file for complete search history.

(56) References Cited

U.S. PATENT DOCUMENTS

| | | | |
|---|---|---|---|
| 6,232,079 B1 | 5/2001 | Wittwer et al. | |
| 6,303,305 B1 | 10/2001 | Wittwer et al. | |
| 6,387,621 B1 | 5/2002 | Wittwer | |
| 6,503,720 B2 | 1/2003 | Wittwer et al. | |
| 6,783,934 B1 | 8/2004 | McMillan et al. | |
| 6,911,327 B2 | 6/2005 | McMillan et al. | |
| 6,942,971 B2 | 9/2005 | McMillan et al. | |
| 2004/0097460 A1* | 5/2004 | Ivey et al. | 514/44 |

FOREIGN PATENT DOCUMENTS

| | | |
|---|---|---|
| EP | 0906449 B1 | 3/2004 |
| EP | 1041158 B1 | 10/2005 |
| EP | 0912760 B1 | 11/2005 |
| EP | 1059523 B1 | 7/2007 |
| EP | 0912766 B1 | 4/2009 |
| EP | 1674585 B1 | 10/2010 |
| WO | WO 97/46707 | 12/1997 |
| WO | WO 97/46712 | 12/1997 |
| WO | WO 01/84463 | 11/2001 |
| WO | 2004/024951 | 3/2004 |
| WO | 2007/081613 | 7/2007 |

OTHER PUBLICATIONS

Heid (Genome Research (1996) vol. 6, pp. 986-994).*
Ginzinger et al. (Experimental Hematology (2002) vol. 30, pp. 503-512.*
Hellemans et al. (Genome Biology (2007) vol. 8:R19, pp. R19-R19.14).*
Lalam et al. (C.R. Acad. Scr. Paris (2005) Ser. I 341, pp. 631-634).*
Ramakers et al. (Neuroscience Letters (2003) vol. 339, pp. 62-66.*
PCT International Search Report and Written Opinion mailed Dec. 22, 2008 for International Patent Application No. PCT/US2008/074614.
Becker Sven et al., "Quantitative Tracing, by Taq Nuclease Assays, of a Synechococcus Ecotype in a Highly Diversified Natural Population." Applied and Environmental Microbiology, vol. 68, No. 9, Sep. 2002, pp. 4486-4494.
Schnell S. et al, "Enzymological Considerations for a Theoretical Description of the Quantitative Competive Polymerase Chain Reaction (QC-PCR)." Journal of Theoretical Biology, Academic Press, London, GB, vol. 184, Jan. 1, 1997, pp. 433-440.
Becker Sven et al., "PCR Bias in Ecological Analysis: a Case Study for Quantitative Taq Nuclease Assays in Analyses of Microbial Communities." Applied and Environmental Microbiology, vol. 66, No. 11, Nov. 2000, pp. 4945-4953.
Burg, et al. (1995) *Analytical Biochemistry* 230:263-272.
Pritham, et al. (1998) *Journal of Clinical Ligand Assay* 21:404-412.
Rasmussen et al. (1998) *Biochemica* 2:8-11.

* cited by examiner

*Primary Examiner* — Lori A Clow
(74) *Attorney, Agent, or Firm* — Knobbe Martens Olson & Bear LLP

(57) ABSTRACT

Systems and methods for calculating an initial amount of target nucleic acid $N_0$ in a sample are provided. A plurality of fluorescent measurements is received. Each respective fluorescent measurement $FS_n$ is taken in a different cycle n in a PCR amplification experiment of the sample. Then, a model for the PCR amplification experiment is computed. For each respective fluorescent measurement, the model comprises a respective equation for $N_n$, where (i) $N_n$ is the calculated amount of the target nucleic acid in cycle n of the corresponding PCR amplification experiment, and (ii) the equation for $N_n$ is expressed in terms of K and $N_0$, where K is the Michaelis-Menton constant. The model can be refined by adjusting K and $N_0$ until differences between model values $N_n$ and corresponding fluorescent measurements are minimized, thereby calculating the initial amount of a target nucleic acid $N_0$ as the minimized value for $N_0$ for the model.

56 Claims, 41 Drawing Sheets

SYSTEMS AND METHODS FOR DETERMINING AN AMOUNT OF STARTING REAGENT USING THE POLYMERASE CHAIN REACTION

CROSS REFERENCE TO RELATED APPLICATION

This application claims benefit, under 35 U.S.C. §119(e), of U.S. Provisional Patent Application No. 60/968,466, filed on Aug. 28, 2007, which is hereby incorporated by reference herein in its entirety.

1 FIELD OF THE INVENTION

Disclosed are systems and methods for extracting quantitative information about the initial amount of a target nucleic acid $N_o$ in a sample from individual polymerase chain reaction (PCR) amplification curves governed by Michaelis-Menten kinetics.

2 BACKGROUND OF THE INVENTION

The polymerase chain reaction (PCR) is an in vitro method for enzymatically synthesizing or amplifying defined nucleic acid sequences. The reaction typically uses two oligonucleotide primers that hybridize to opposite strands of a DNA molecule and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in real-time PCR, or kinetic PCR, to facilitate detection and quantification of the amplification process.

Referring to FIG. 1, the steps of a cycle in the real-time polymerase chain reaction (PCR) are described. There are three steps in a PCR cycle. In step 1 of the cycle, the temperature is raised to about 95 degrees, and then the target DNA that is to be amplified gets denatured into two separate strands at that point. In step 2 of the cycle, the temperature is lowered to about 50 degrees at which point primers are annealed to the single strands. The primers are short oligomers that specifically attach to each of the two denatured DNA strands. In step 3 of the cycle, the temperature is raised to 72 degrees and a polymerase enzyme extends the separated strands so that, after each cycle, where for each double-stranded DNA, two copies of the double-stranded DNA are produced. These steps are repeated in each cycle in order to amplify target nucleic acid. For instance, the aforementioned steps of the PCR cycle may be repeated forty or more times.

Referring to FIG. 2, during real-time PCR, a fluorescent signal is measured during the cycling. This fluorescent signal is a measure of the number of double-stranded DNA that has been produced. Curve 202 is the measurement of the fluorescent signal after each cycle on an absolute scale and curve 204 is the measurement of the fluorescent signal after each cycle on a logarithmic scale. From curve 202, is can be seen that there are three distinct phases during real-time PCR. The first phase is the exponential phases. In the particular case illustrated in FIG. 2, the exponential phase roughly consists of cycles 1-26. The second phase is the linear phase. During the linear phase, the fluorescent signal grows linearly as a function of PCR cycle then the signal starts leveling off. In the particular case illustrated in FIG. 2, the linear phase consists of PCR cycles 27-31. The cycles where the fluorescent signal begins leveling off is referred to as the plateau phase. In the particular case illustrated in FIG. 2, the plateau phase consists of PCR cycles 32-40.

Part of the exponential phase is not visible because the fluorescent signal is less than the background. This can be seen in FIG. 2, where the fluorescent signal is below background noise for PCR cycles 1 through 20. So, for the first PCR cycles, no detectable fluorescent signal is read. The fluorescent signal is not observed until it becomes strong enough to measure it. In the particular case illustrated in FIG. 1, the fluorescent signal is strong enough to measure after the $21^{st}$ PCR cycle. Often the fluorescent signal cannot be detected for the first several PCR cycles because there are typically as few as 20 to 100 copies of the original target double stranded nucleic acid that is to be amplified. Thus, there is essentially nothing to measure during the initial stages of the real time PCR because the strength of fluorescent signal is proportional to the number of copies of double stranded nucleic acid that are in the reaction mixture.

Assuming one hundred percent efficiency, each PCR cycle will double the number of double stranded target nucleic acids in the reaction mixture. Therefore, assuming that the PCR is one hundred percent efficient, the total number of templates (double stranded target nucleic acid) in each cycle doubles so that, after n-cycles, the number templates $N_n$ in the reaction mixture will be $N_o$, where $N_o$ is the number of copies of the template in the initial reaction mixture before real-time PCR amplification was initiated, times two to the power of n:

$$N_n = N_o * 2^n \quad (1)$$

If the efficiency is other than one hundred percent, then the number of templates $N_n$ in the reaction mixture after n-cycles will be:

$$N_n = N_o * (1+E)^n \quad (2)$$

where E is the efficiency. In practice, real-time PCR is not one hundred percent efficient and thus E is a real value less than one. Taking the log of equation (2) yields:

$$\text{Log}(N_n) = \text{Log}(N_o) + n\, \text{Log}(1+E)^n \quad (3)$$

Where $\text{Log}(N_n)$, the logarithm of the number of copies of the template in the reaction mixture in the $n^{th}$ cycle, is the summation of logarithm of the initial number of templates $N_o$ and n times the log of the efficiency plus 1 to the $n^{th}$ power. Referring to FIG. 3, the advantage of expressing $N_n$ in the logarithmic form of Equation 3 is that a threshold line T can be established. The threshold line T is set at a value above background noise. Placement of the threshold line T can be varied, but it is placed somewhere in the exponential phase of the curve that is above background noise. Once the threshold line T has been placed, the goal is to accurately determine the number $C_T$ of real-time PCR cycles that are required to achieve a fluorescent signal that is equal to or greater than T. From Equation (3), $C_T$ will be:

$$C_T = -\text{Log}(N_o)/\text{Log}(1+E) + \text{Log}(T)/\text{Log}(1+E) \quad (4)$$

From FIG. 3, it can be seen that the logarithm of the fluorescent signal has a negative value for the initial number of copies. The threshold value T can be varied, but from Equation 4, it can be seen that $C_T$ should depend as minus log $N_o$.

Referring to FIG. 4, in quantitative PCR, several amplification curves are computed. This can be done in the linear scale (402) or the log-scale (404). In FIG. 4, the amplification curves are for the target nucleic acid PBEF1. Each of these amplification curves represents a serial dilution of an initial sample of PBEF1. Furthermore, each of these serial dilutions may be performed in triplicate. In other words, the initial sample is divided into three samples, where the number of the target nucleic acid is the same in each of the samples. Real-time PCR is performed on each of the three samples. Each of the three samples is then serial diluted and real-time PCR is performed on the serially diluted samples. The goal of all this work and the computation of all the amplification curves are to find out how many copies of the template nucleic acid ($N_o$) were initially in the sample.

The premise behind serial dilutions is that, when $N_o$ is the number of target nucleic acid in the original sample, and the sample is repeatedly diluted by a factor of two, $N_o$ should likewise by reduced by a factor of two. Thus, according to Equation (4), when $C_T$ is calculated for each of the serial dilutions, $C_T$ should be linear function of $Log(N_O)$ with the slope of $-1/Log(1+E)$. Computation of $C_T$ as a function of $Log(N_o)$ is called a standard curve. Such a standard curve is illustrated for the amplification curves of PBEF1 in FIG. 5. The value $Log(N_o)$ is taken on the illustrated y-axis and $C_T$ is taken on the X-axis. Furthermore, as illustrated in FIG. 5, the standard curve is linear.

Because the standard curve is linear, it is possible to compute the coefficient of determination, $R^2$, or an adjusted $R^2$ and the efficiency E. An adjusted $R^2$ is defined as:

$$1 - (1 - R^2)\frac{n-1}{n-p-1} \quad (5)$$

where p is the total number of regressors in the model and n is sample size. For the data in FIG. 4 and plotted as a standard curve in FIG. 5, the adjusted $R^2$ is 0.999011. Thus, FIG. 5 shows that with smaller $N_0$s, it takes fewer cycles to achieve $C_T$ and as $N_0$ is increased a logarithm, linearly $C_T$ becomes greater. Thus, from the standard curve, the value $C_T$ for the initial undiluted sample $N_0$ can be computed from the slope. From Equation 4, $$C_T = -Log(N_0)/Log(1+E) + Log(T)/Log(1+E) \quad (6)$$

$$= -3.4 Log(N_0) + 26.081 \quad (7)$$

For the data in FIG. 4 and plotted as a standard curve in FIG. 5, the efficiency E is 96.8%, which is nearly a perfect 100%.

Equation 4, and the computations set forth in Equations 6 and 7 which are examples of computations of Equation 4, have a number of underlying assumptions. One assumption is that, for all the cycles for which the fluorescent signal is larger than background, the fluorescent signal will be proportional to the number of copies of the target nucleic acid (and its amplified copies). This assumption is not problematic. Furthermore, Equation 4 assumes that each of the cycles leading up to $C_T$ is in the exponential phase. T cannot be set in the linear or plateau phase because the assumptions underlying Equation 4 do not work in those phases. Again, this assumption is not problematic because T can be set in the exponential phase. Furthermore, automated software in many PCR machines can find a reasonable value for T on an automated basis, or the user can set T somewhere in the exponential phase.

One problematic assumption behind Equation 4 is that it assumes that efficiency E in each of the cycles leading up to $C_T$ are the same, including cycles where the fluorescent signal simply is not measurable because it is still less than the background. However, it is not possible to verify this assumption when no measurable signal is obtain from the first several PCR cycles. Moreover, another problematic assumption is that Equation 4 assumes that the efficiency will be the same for all the response curves (e.g., the response curves illustrated in FIG. 4), independent of the initial template concentration and individual reactions conditions. So, Equation 4 assumes that, for the entire set of response curve experiments, E is the same. The assumption that E is the same for each cycle before $C_T$ in a given PCR experiment and that E is constant for each of the PCR experiments done in a serial dilution presents a significant problem because there is no guarantee that these assumptions are, in fact valid. For example, consider the case in which there are two different samples each with a different target nucleic and the goal is to quantifiably compare the initial concentration of the target nucleic acids in the two samples. From the above analysis, a comparison of the initial concentration of the two target nucleic acids may be problematic using conventional techniques because there is no guarantee that E will be the same in the PCR experiments used to generate the amplification curves for the two samples. This point can also be seen below, in conjunction with FIG. 7 where it is shown that the efficiency of the PCR reactions for the IFNAR1 amplification curves is substantially below the efficiency of the efficiency of the PCR reactions for the PBEF1 amplification curves of FIG. 4 (E=83.5% for IFNAR1, as compared to E=96.8% for PBEF1).

Referring to FIG. 6, the efficiency of a given PCR experiment can be checked. By definition, the efficiency of any given cycle n in a PCR experiment $E_n$ (termed local efficiency, as opposed to the assumed constant efficiency of the overall PCR experiment throughout the plurality of cycles of the PCR experiment) is (i) the number of copies of the target nucleic acid in the current cycle $N_n$ divided by (ii) the number of copies of the target nucleic acid in the previous cycle $N_{n-1}$ minus 1:

$$E_n = N_n/N_{n-1} - 1 \quad (8)$$

FIG. 6, which plots local efficiency $E_n$ for each of the cycles of a real-time PCR experiment in the PBEF1 amplification curves, shows that $E_n$ varies all over the place. There is no requirement that $E_n$ be set to one hundred percent for calculations based upon Equation 4, but such calculations do assume that $E_n$ is constant. As can be seen in FIG. 6, the value of $E_n$ is not known in the initial cycles, because there is no measurable fluorescent signal. And, for those cycles in the exponential phase where a measurable fluorescent signal is seen, $E_n$ falls off. As seen in FIG. 6, when a measurable fluorescent signal is detected near cycle 20, the efficiency is somewhere around 1. Then it falls off, all the way down to zero. Furthermore, there is no guarantee that the efficiency for cycles less than 20 are constant either. From what is observable, the efficiency is not constant.

FIG. 6 illustrates that the efficiency of the PCR reaction is not anywhere near 97%. But, the standard curves for the same sample, as illustrated in FIGS. 4 and 5, indicate that the efficiency of the PCR reactions is, in fact 97%. Thus, there is a discrepancy between the efficiency E computed by the standard curve of FIG. 5 and the local efficiency computed in FIG. 6.

Moreover, as indicated above, the standard curve illustrated in FIG. 5 has no mechanism for compensating for variations in efficiency that will arise when different reagents or different reaction conditions are used in the various PCR reactions used to generate the data for a standard curve.

Referring to FIG. 7, amplification curves for the target nucleic acid IFNAR1 are illustrated as well as the standard curve from these amplification curves. From the standard curve:

$$C_T = -Log(N_0)/Log(1+E) + Log(T)/Log(1+E) \quad (9)$$

$$= -3.795 Log(N_0) + 30.955 \quad (10)$$

Furthermore, E for the IFNAR1 data is 83.5 percent. Referring to FIG. 8, which plots local efficiency $E_n$ for each of the cycles of a real-time PCR experiment in the IFNAR1 amplification curves, shows that $E_n$ varies all over the place.

Referring to FIG. 9 the determination of how adjusted $R^2$ and efficiency vary for the PBEF1 and IFNAR1 datasets discussed above as a function of threshold T placement. Referring to FIG. 8, the data for FIG. 9 is, for example, computed by setting threshold T line 802 to one value, calculating the $C_T$, moving T somewhere else, and recalculating $C_T$ and so forth. If the threshold T (line 802) is moved too high, then the data no longer falls completely in the exponential region, particularly on the log scale. In the log scale this exponential phase should be linear. If line 802 (T) is moved above where it starts falling off, then you're already not in the exponential phase of the Equation 4. So it is expected that if the threshold is moved high enough, than the assumptions underlying Equation 4 will no longer be valid and efficiency will go down. As illustrated in FIG. 9, the higher threshold T is set (in terms of fluorescent signal strength) the more efficiency starts falling off. Thus, not only is efficiency dependent on starting reagent (PBEF1 versus IFNAR1), it is also dependent on the choice for the value of T.

Ideally, there should be a low enough T, such that calculated efficiency is 98% or a value close to 98%. And, when the threshold is increased, the efficiency should go down because regions of the PCR experiment where the efficiency is going down are being incorporated (see for example the local efficiencies computed for PBEF1 and IFNAR1 in FIGS. 6 and 8). But as illustrated in FIG. 9, this is not always the case. As illustrated in FIG. 9, IFNAR1, does what it's supposed to do. The efficiency begins on the order of 0.85. Then, at the threshold T is set higher, the efficiency falls down. But in the case of PBEF1, the efficiency begins at 0.98 and, when T is increased thereby including less efficient cycles into the computation, the efficiency does not go down, but, as illustrated in FIG. 9, actually increases.

The above analysis indicates that the concept of the efficiency is problematic. Thus, methods that rely on efficiency in order to compare the starting concentration of target nucleic acids in one sample to the starting concentration of a target nucleic acid in another sample are problematic.

The standard curve can be used to calculate, to predict, the starting value for $N_0$. That is the goal of quantitative PCR: calculation of $N_0$ from the $C_T$s, based upon the standard curve. So in principle, the standard curve is computed thereby giving the relation between $C_T$ and $N_0$. This relation can be used in further experiments to predict the specific value for $N_0$. So, from the same data used to calculate the standard curve, one can try to predict the specific value for $N_0$ to check how well the method works for the same set of data. Referring to FIG. 10, absolute error AE in the prediction of $N_0$ using the standard curves as set forth above can be computed when the actual $N_0$ of the sample is known. The absolute error is defined as:

$$AE = |N_0^{actual} - N_0^{predicted}| \qquad (11)$$

In other words, AE is the absolute value of the difference between the known initial $N_0$ and the predicted $N_0$. Because AE is becomes less sensitive when the initial $N_0$ increases, absolute relative error, which divides absolute error by the actual $N_0$ to provide an error value that doesn't vary significantly as a function of the value of $N_0$. From FIG. 10, it can be seen that for the PBEF1 data, the mean ARE (over all the serial dilutions) is 3.9% whereas for IFNAR1, the mean ARE (over all the serial dilutions) is 6.5%. This shows that the ARE varies from gene to gene and as a function of $N_0$, but the values obtained for PBEF1 and IFNAR1 are typical for a fully-quantitative PCR.

In gene expression measurements, there is an additional step, because the desired quantity is mRNA concentration, not the measured cDNA. So the additional step is determining the efficiency of the reverse transcription from the desired quantity, initial mRNA concentration, the measured quantity, cDNA. The reverse transcriptase reaction contributes most of the variation to the measurement of the mRNA quantity. While it is possible to determine the efficiency of the reverse transcription reaction and therefore the desired value, initial mRNA concentration, in practice this is a difficult process. Thus, to circumvent the need for determining the efficiency of the reverse transcriptase reaction, in practice what is done is to compare the measured abundance value of the gene of interest to that of a reference gene. As shown below, this circumvents the need to know the efficiency of the reverse transcriptase reaction for the gene of interest. In the method, two different genes are measured at the same time: the one of interest and the one that is assumed will not vary (e.g. is not regulated by the biological condition under study). The relative expression for two genes, A and B is given by:

$$\frac{N_A}{N_B} = \kappa_{RS} \frac{\eta_A (1+E_B)^{C_{TB}-1}}{\eta_B (1+E_A)^{C_{TA}-1}} \qquad (12)$$

where $\kappa_{RS}$ is the relative sensitivity of the detection chemistries for genes A and B, $\eta_A$ is the cDNA reverse transcriptase yield for gene A, $\eta_B$ is the cDNA reverse transcriptase yield for gene B, $E_A$ is the efficiency of the PCR reaction for gene A, $E_B$ is the efficiency of the PCR reaction for gene B, $N_A$ is the mRNA abundance of gene A, $N_B$ is the mRNA abundance of gene B, $C_{TB}$ is $C_T$ for gene A, and $C_{TB}$ is $C_T$ for gene B.

The value $\kappa_{RS}$ will depend on many different reaction conditions. In order to avoid the problem of determining the unknown parameters $\kappa_{RS}$, $\eta_A$ and $\eta_B$, the "comparative quantification" method (or $\Delta\Delta C_T$-method) is used. Parameters $\kappa_{RS}$, $\eta_A$, and $\eta_B$ cancel out when a ratio of the ratios $N_A/N_B$ for different samples is considered, assuming that the parameters' values do not vary from sample to sample.

Typically, the gene of interest (gene A) is a gene of interest. For example, the abundance of the mRNA of gene A is being studied because it is believed that the abundance of the mRNA of that gene various as a function of the state of a disease under study in members of a population. In such instances, a gene B is chosen as a reference gene for computations in accordance with Equation 12 that is not believed to vary as a function of the state of the disease under study in the members of the population and, moreover, where it is believed that the expression level of the mRNA for gene B does not change in the members of the population. So, two quantitative PCR reactions are done at the same time, one for the gene of interest (e.g., gene A) in and one for the reference gene (e.g. gene B). From these experiments, $N_A$ and $N_B$ are calculated. If the parameters $\kappa_{RS}$, $\eta_A$ and $\eta_B$, do not change, than it is sufficient to simply compare the ratios:

$$\rho \equiv \frac{(1+E_B)^{C_{TB}-1}}{(1+E_A)^{C_{TA}-1}} = \psi \frac{N_A}{N_B} \quad (13)$$

for different samples, with $\psi = \eta_A/\eta_B \kappa_{RS}$ being a constant. This is because the values for $\eta_A$, $\eta_B$ and $\kappa_{RS}$ are not important if they do not vary from sample to sample. Thus, if the goal is to compare a disease state with a healthy state, then the ratio of the quantity $(1+E_B)^{C_{TB}-1}$ and the quantity $(1+E_A)^{C_{TA}-1}$ is all that is needed if $\eta_A$, $\eta_B$ and $\kappa_{RS}$ do not vary. Additionally, if the assumption is made that the efficiency for both genes A and B (the gene of interest and the reference gene) is the same, and that efficiency is E ($E_A = E_B \equiv E$), than Equation 13 will reduce to Equation 14:

$$\psi \frac{N_A}{N_B} = (1+E)^{C_{TB}-C_{TA}} \quad (14)$$

With Equation 14, different samples can be quantitatively compared by just comparing $\Delta C_T \equiv C_{TB} - C_{TA}$. If the efficiencies $E_A$ and $E_B$ are known than $\rho$ from Equation 14 can be calculated.

In conventional quantitative PCR, $\Delta C_T$ is the metric that is used to compare different samples. However, as discussed above, $\Delta C_T$ assumes that $E_A$ and $E_B$ are the same. Exemplary data indicates that the assumption that $E_A$ and $E_B$ are the same is problematic because the calculated efficiency of various genes that have been studied ranges. For example, E for the gene PBEF1 is E=0.9684±0.0094, E for the gene ADM is E=0.91411±0.0164, E for IL1R2 is E=0.7744±0.0156, E for IRAK3 is 1.0118±0.0130, and E for JAK3 is 0.9777±0.0102. Even more problematically, the E for some genes varies from test to test. For example, the E for the reference gene (gene 18S in the considered example) have been variously computed as 0.88, 0.93, 0.97, and 1.1.

Given the variation in $E_A$ and $E_B$ when Equation 14 assumes no such variation, of interest is how much error the variation in $E_A$ and $E_B$ introduces into the ratio $N_A/N_B$ when just $\Delta C_T$ is used to compare different samples. Applying standard error propagation law:

$$z = f(x_1, x_2, \ldots, x_n) \quad (15)$$

$$\sigma_z^2 = \sum_{i=1}^{n} \left(\frac{\partial F}{\partial x_i}\right)^2 \sigma_{x_i}^2 \quad (16)$$

and thus:

$$z = \text{Log}_{10}\rho = \text{Log}_{10} \frac{(1+E_B)^{C_{TB}-1}}{(1+E_A)^{C_{TA}-1}} \quad (17)$$

and the use of typical values for the parameters:

$E_A = E_B \cong 96\%$, $CT_A \cong 9.5$, $CT_B \cong 26$, and $\sigma(CT_A) = \sigma(CT_B) \cong 0.12$, the coefficient of variance of $\text{Log}_{10}\rho$, $CV(\text{Log}_{10}\rho)$, can be computed. $\text{Log}_{10}\rho$ is the measure of the ratio of genes A and B. $CV(\text{Log}_{10}\rho) \equiv \rho(\text{Log}_{10}\rho)/\text{Log}_{10}\rho$ as a function of $CV(E_B)$ and $CV(E_A)$. As illustrated in the top graph of FIG. 11, $CV(\text{Log}_{10}\rho)$, does not vary much as a function of the coefficient of variance of the gene with low CT (here gene B). Typically, the reference gene will have low CT. Thus, even if the coefficient of variance of the efficiency of the reference gene goes from, say, 2% to 8%, $CV(\text{Log}_{10}\rho)$ will not change very much, as exhibited by the flat curves in the upper graph in FIG. 11. On the other hand, referring to the lower graph of FIG. 11, the coefficient of variance of the efficiency of the gene with high CT (here gene B) has dramatic effect on the error of $\text{Log}_{10}\rho$. As can be seen in the lower graph of FIG. 11, the relationship between the coefficient of variance of gene B and the error of $\text{Log}_{10}\rho$ share a linear relationship. Thus, the lower graph shows that significant error arises if the assumption that the efficiency doesn't vary, when in fact it does.

Referring to FIG. 12, it is seen that the $C_T$ values for the reference gene 18S for four different samples each with three replicates per sample exhibits little variation from sample to sample, consistent with the assumption that the 18S gene is not expressed in the subjects that provided the samples. FIG. 13 shows the mean $C_T$ values of 18S and their 95% confidence intervals (CI) based on the three replicates. As shown in FIG. 13, there is little variation of the $C_T$ of 18S from sample to sample, consistent with the assumption that 18S is not expressed in the subjects that provided the samples. Thus, FIGS. 12 and 13 collectively show that the abundance of 18S mRNA does not vary from sample to sample, although the samples are from completely different patients. In FIG. 14, $C_T$ values of a gene that is expressed, PBEF1, for four different samples with three replicates for each sample are given. In FIG. 15, mean $C_T$ values for PBEF1 are well separated for different samples. In FIG. 15, the 95% confidence intervals shown are based on the three replicates for each sample. In FIG. 16, it is seen that means of $\Delta CT \equiv CT_{PBEF1} - CT_{18S}$ are quite well separated from sample to sample. However, as discussed in the background section above, $\Delta C_T$ does not directly reflect potential differences in the ratio $N_{18S}/N_{PBEF1}$ for different samples, and one has to consider the variability of these ratios (or at least of $\rho$ or $\text{Log}_{10}\rho$).

Referring to FIG. 17, if the gene efficiencies $E_{PBEF1}$ and $E_{18S}$ do not vary from sample to sample, and the only source of the efficiency uncertainty is related to the regression of the standard curve, then the means of the calculated $\log_{10}\rho$ are still potentially well separated. This suggests that the standard quantitative PCR (qPCR) analysis is capable of detecting differences in the ratio $N_{18S}/N_{PBEF1}$ in the subjects that provided the samples, if such differences exist. In this example, E=0.9684±0.0094 is assumed for both PBEF1 and 18S. With this efficiency of 18S, typical coefficient of variance values for the resulting metric $\log_{10}\rho$ for the considered example genes and samples are between about 1.5% and 3%.

Referring to FIG. 18 if, however, the variability of $E_{PBEF1}$ and $E_{18S}$ from sample to sample is taken into account, the confidence intervals of $\log_{10}\rho$ for the ratio $N_{18S}/N_{PBEF1}$ are so large that the sample separation becomes questionable. In this example $E_{18S}$=0.97±0.094 (CV~10%) and $E_{PBEF1}$=0.97±0.047 (CV~5%) are assumed, representing a potential worse-case scenario. These results suggest that unless something can be done to control the efficiency variation, the standard qPCR analysis presented here may not lead to a reliable detection of differences in the ratio $N_{18S}/N_{PBEF1}$.

If the conditions of FIG. 17 hold true, a determination can be made as to whether there are differences in the ratio $N_{18S}/N_{PBEF1}$ in various subjects because the 95% confidence interval do not overlap. But if the conditions of FIG. 18 hold true, where an error in the assumptions of efficiency are made, the confidence intervals start overlapping and the ability to discriminate changes in the ratio $N_{18S}/N_{PBEF1}$ from sample to sample is lost.

Thus, given the likely sources of error in the equations above when the assumptions underlying the equations are, in fact, not correct, what is needed are new methods for extracting quantitative information about the initial amount of a target nucleic acid from individual PCR amplification curves.

3 SUMMARY OF THE INVENTION

The present invention provides systems and methods for extracting quantitative information about the initial target concentration of a nucleic acid from individual PCR amplification curves. The approach is based, in part, on the fact that the PCR reaction is governed by Michaelis-Menten kinetics (MMK). In the present invention, PCR amplification curves are fitted to the MMK model leading to the direct estimation of the initial template DNA concentration and the effective Michaelis-Menten constant of the PCR reaction. Unlike the conventional methods described above, methods of the present invention require no information and no assumptions about the PCR amplification efficiency. Advantageously, unlike conventional methods, the systems and methods of the present invention can use amplification curve points from both exponential and linear amplification phases when there are not enough available exponential-phase points above the background noise. The MMK model provides direct estimation of the initial template DNA concentration without the necessity of conducting separate efficiency studies. Advantageously, the systems and methods of the present invention require only one calibration point, whereas as standard qPCR approaches need at least two. In contrast to the standard qPCR approaches discussed above, it is possible to construct the standard curve in the linear scale of the initial template concentration and to refine it by including a quadratic term or by using weighted regression to minimize, for example, mean absolute relative error (MARE). As discussed in the background section, standard qPCR quantification methods may lead to very high uncertainties in the ratio $N_A/N_B$ of the initial number of considered genes A and B due to the PCR efficiency variation. In contrast, the systems and methods of the present invention eliminate uncertainties related to PCR efficiency and may reduce the coefficient of variation of $\text{Log}(N_A/N_B)$ as much as 10-fold compared to the standard qPCR approach.

One aspect of the invention provides a method of calculating an initial amount of a target nucleic acid $N_0$ in a sample. In the method a first plurality of fluorescent measurements is received. The fluorescent measurements $FS_n$ in the first plurality of fluorescent measurements comprise fluorescents measurement taken in different cycles n in a first PCR amplification experiment of the sample. A first model is then calculated for the first PCR amplification experiment. The model provides a calculation of the initial amount of target nucleic acid $N_0$ in the sample. For each respective fluorescent measurement in the first plurality of fluorescent measurements, the first model comprises a respective equation for $N_n$, where (i) $N_n$ is the calculated amount of the target nucleic acid in cycle n of the first PCR amplification experiment from which the respective fluorescent measurement was taken, and (ii) the respective equation for $N_n$ is expressed only in terms of K and $N_0$, regardless of the cycle n of the first PCR amplification experiment, where K is the effective Michaelis-Menten constant for the first PCR amplification experiment. Refinement of the first model can be performed. For example, refinement of the first model can comprise adjusting K and $N_0$ until differences between values $N_n$ computed by the first model and corresponding fluorescent measurements in the first plurality of fluorescent measurements are minimized, thereby calculating the initial amount of a target nucleic acid $N_0$ as the minimized value for $N_0$ for the first model. In some embodiments, refinement of the first model is not performed, but rather values for K and $N_0$ are identified by a complete search for all possible values for K and $N_0$. In such a complete search, the values K and $N_0$ identified from the complete search should provide the best agreement for the values $N_n$ computed by the first model for each of the values of n used in the model.

In some embodiments, the method further comprises outputting the calculated initial amount of a target nucleic acid $N_0$ calculated in the calculating step to, e.g., a user interface device, a monitor, a computer-readable storage medium, a computer-readable memory, or a local or remote computer system; or displaying the calculated initial amount of a target nucleic acid $N_0$ calculated in the calculating step.

In some embodiments, the first model comprises an equation for $N_1$, the calculated amount of the target nucleic acid in cycle 1 of the first PCR amplification experiment, where $$N_1 = N_o\left(1 + \frac{K}{K+N_0}\right).$$

In some embodiments, the first model comprises an equation for $N_2$, the calculated amount of the target nucleic acid in cycle 2 of the first PCR amplification experiment, where $$N_2 = N_o\left(1 + \frac{K}{K+N_0}\right)\left(1 + \frac{K}{K+N_0\left(1+\frac{K}{K+N_0}\right)}\right).$$

In some embodiments, the first model comprises an equation for $N_3$, the calculated amount of the target nucleic acid in cycle 3 of the first PCR amplification experiment, where $$N_3 = N_o\left(1 + \frac{K}{K+N_0}\right)\left(1 + \frac{K}{K+N_0\left(1+\frac{K}{K+N_0}\right)}\right)$$
$$\left(1 + \frac{K}{K+N_0\left(1+\frac{K}{K+N_0\left(1+\frac{K}{K+N_0}\right)}\right)\left(1+\frac{K}{K+N_0\left(1+\frac{K}{K+N_0}\right)}\right)}\right).$$

In some embodiments, refinement of the first model by adjustment of K and $N_0$ comprises minimizing the sum of squares of a plurality of residuals $N_n$-$FS_n$ with respect to $N_0$ and K. In some embodiments, the first PCR amplification experiment comprises cycles in a linear phase and cycles in an exponential amplification phase and the first plurality of fluorescent measurements consists of fluorescent measurements taken from cycles in the exponential phase of the first PCR amplification experiment and cycles in the linear phase of the first PCR amplification experiment.

In some embodiments, the first plurality of fluorescent measurements is fluorescent measurements taken from a contiguous number of cycles in the first PCR amplification experiment that is bounded by cycle $n_{start}$ and cycle $n_{end}$. In some embodiments, $n_{start}$ is the PCR cycle in the first PCR amplification experiment for which (i) the local efficiency of all subsequent cycles in the first PCR amplification experiment consistently decreases, and (ii) the efficiency of the cycle $n_{start}+1$ of the first PCR amplification experiment is less than 1.05. In some embodiments, $n_{end}$ is the first cycle in the first PCR amplification experiment where a second derivative of the observed fluorescent signal ($d^2FS/dn^2$) is less than zero. In some embodiments, the first PCR amplification experiment comprises cycles in a linear phase and the first plurality of fluorescent measurements typically consists of between seven and twelve points in the linear phase of the first PCR amplification experiment.

In some embodiments, the receiving step comprises receiving a plurality of fluorescent measurements for each PCR amplification experiment in a plurality of PCR amplification experiments. In such embodiments, the calculating step comprises computing a model in a plurality of models for each PCR amplification experiment in the plurality of PCR amplification experiments, where, for each respective model in the plurality of models, the respective model comprises a respective equation for $N_n$ for the corresponding fluorescent measurement n in the PCR amplification experiment corresponding to the respective model. Each $N_n$ in the respective model is the amount of target nucleic acid in cycle n of the PCR amplification experiment corresponding to the respective model from which the respective fluorescent measurement was taken. In this embodiment, each respective equation for $N_n$ in the respective model is expressed only in terms of K and $N_0$, regardless of the cycle n of the corresponding fluorescent measurement in the corresponding PCR amplification experiment that is corresponding to the respective equation for $N_n$, where K is the Michaelis-Menten constant for the corresponding PCR amplification experiment. In some embodiments, the plurality of models is refined. For example, refinement of each respective model in the plurality of models can be done by adjusting K and $N_0$ for each equation for $N_n$ in the respective model until differences between values $N_n$ computed by the respective model and corresponding fluorescent measurements in the plurality of fluorescent measurements of the PCR amplification experiment corresponding to the respective model are minimized, thereby calculating the initial amount of a target nucleic acid $N_0$ as the minimized value for $N_0$ for each respective model.

In some embodiments, each PCR amplification experiment in the plurality of PCR amplification experiments represents a serial dilution of the sample. In such embodiments, the method further comprises plotting $\log_{10}(N_0)$ of the initial amount of a target nucleic acid $N_0$ calculated for each model in the plurality of models as a function of relative concentration of the sample used in the PCR amplification experiment for each model in the plurality of models. The relative concentration of the sample is determined by the dilution factor used in each serial dilution. In some embodiments, each PCR amplification experiment in the plurality of PCR amplification experiments represents a serial dilution of the sample, and the method further comprises plotting the initial amount of a target nucleic acid $N_0$ calculated for each model in the plurality of models as a function of relative concentration of the sample used in the PCR amplification experiment for each model in the plurality of models.

In some embodiments, each PCR amplification experiment in the plurality of PCR amplification experiments represents a serial dilution of the sample, and the method further comprises refining the value $N_0$ calculated for each model in the plurality of models as a function of relative concentration of the sample so that a single refined value for $N_0$ is computed for the plurality of models. In some embodiments, the refining step comprises performing a weighted regression to minimize a mean absolute relative error (ARE) of a plurality of ARE values with respect to the value $N_0$ calculated by each model in the plurality of models, where each $$ARE = \frac{|C_0^{actual} - C_0^{predicted}|}{C_0^{actual}}$$

value in the plurality of ARE values is for a respective model in the plurality of models, $C_0^{actual}$ is the actual relative concentration of the sample used for the PCR amplification experiment corresponding to the respective model, and $C_0^{predicted}$ is the calculated relative concentration of the sample used for the PCR amplification experiment corresponding to the respective model that is determined by the calculated value $N_0$ for the respective model.

In some embodiments, each PCR amplification experiment in the plurality of PCR amplification experiments represents a serial dilution of the sample, where the serial dilution is done in duplicate or triplicate (or some larger number of replicates) and a different model is computed for each duplicate of each serial dilution or each triplicate (or some larger number of replicates) of each serial dilution. In some embodiments, the receiving step comprises receiving a plurality of fluorescent measurements for a second PCR amplification experiment using the sample. Further, the calculating step comprises calculating a second model for the second PCR amplification experiment, where, for each respective fluorescent measurement in the second plurality of fluorescent measurements, the second model comprises a respective equation for $N_n$, where (i) $N_n$ is the calculated amount of target nucleic acid in cycle n of the second PCR amplification experiment from which the respective fluorescent measurement was taken, (ii) the respective equation for $N_n$ in the second model is expressed only in terms of $K_2$ and $N_0$, regardless of the cycle n, where $K_2$ is the Michaelis-Menten constant for the second PCR amplification experiment, and refinement of the second model comprises adjusting $K_2$ and $N_0$ until a difference between values $N_n$ computed by said second model and corresponding fluorescent measurements in the second plurality of fluorescent measurements are minimized. The method further comprises computing $$\rho = \frac{N_{AM}}{N_{BM}}$$

where $N_{AM}$ is the calculated $N_0$ for the sample computed by the first model and $N_{BM}$ is the calculated $N_0$ for the sample computed by the second model. In some embodiments, the first amplification experiment amplifies mRNA of a first gene and the second amplification experiment amplifies mRNA of a second gene, where $N_{AM}$ is a measure of an abundance of the mRNA of the first gene in the sample and $N_{BM}$ is a measure of an abundance of the mRNA of the second gene in the sample. In some embodiments, the first gene is a gene associated with a phenotypic characterization and the second gene is a gene that is not associated with the phenotypic characterization.

In some embodiments, $\rho$ is above a threshold value, and the member of a species that contributed the sample is deemed to have the phenotypic characterization. In some embodiments, $\rho$ is above a threshold value, and the member of a species that contributed the sample is deemed to not have the phenotypic characterization. In some embodiments $\rho$ is below a threshold value, and the member of a species that contributed the sample is deemed to have the phenotypic characterization. In some embodiments, when ρ is below a threshold value, the member of a species that contributed the sample is deemed to not have the phenotypic characterization. In some embodiments, the phenotypic characterization is a cell type, a cell morphology, a disease state (absence, presence, stage), an abnormal state in a tissue or organ, an abnormal cell type, or an abnormal cell morphology. In some embodiments, the phenotypic characterization is an indication that the test subject from which the sample was taken is likely to develop sepsis. In some embodiments, the initial amount of a target nucleic acid $N_0$ in the sample is a concentration of the mRNA of a first gene in the sample. In some embodiments, the initial amount of a target nucleic acid $N_0$ in the sample is a number of mRNA molecules transcribed from a first gene in the sample.

Another aspect of the invention provides a method of determining whether a sample has a phenotypic characterization. The method comprises (A) calculating a first model for a first PCR amplification experiment comprising a first plurality of cycles, where the first PCR amplification experiment comprises a first plurality of fluorescent measurements. Each respective measurement in the first plurality of fluorescent measurements is taken from a different cycle in the first plurality of cycles of the first PCR amplification experiment. The first PCR amplification experiment is a PCR amplification of a first gene in the sample. The first model comprises a respective equation of an amount $N_n$ of the first gene for each cycle n in the first PCR amplification experiment. In certain embodiments, each respective equation for $N_n$ in the first model is expressed only in terms of $K_1$ and $N_{AM}$, regardless of the cycle n represented by the respective equation $N_n$, wherein $K_1$ is the Michaelis-Menten constant for the first PCR amplification experiment and $N_{AM}$ is the amount of the first gene in the sample prior to the first PCR amplification experiment of the sample. The method further comprises (B) calculating a second model for a second PCR amplification experiment comprising a second plurality of cycles. The second PCR amplification experiment comprises a second plurality of fluorescent measurements. Each respective measurement in the second plurality of fluorescent measurements is taken from a different cycle in the second plurality of cycles of the second PCR amplification experiment. The second PCR amplification experiment is a PCR amplification of a second gene in the sample. The second model comprises a respective equation of an amount $N_n$ of the second gene for each cycle n in the second PCR amplification experiment. Each respective equation for $N_n$ in the second model is expressed only in terms of $K_2$ and $N_{BM}$, regardless of the cycle n represented by the respective equation $N_n$, where $K_2$ is the Michaelis-Menten constant for the second PCR amplification experiment, and $N_{BM}$ is the amount of the second gene in the sample prior to the second PCR amplification experiment of the sample. The method further comprises (C) using the first model to determine a value for $N_{AM}$ and the second model to determine a value for $N_{BM}$. The method further comprises (D) computing $$\rho = \frac{N_{AM}}{N_{BM}}$$

where the value computed for ρ is indicative of whether the sample has the phenotypic characterization.

In some embodiments, a plurality of first models are calculated, where each first model is a PCR amplification experiment of the first gene from a serial dilution of the sample and where $N_{AM}$ is taken as a measure of central tendency of the values $N_{AM}$ determined from each of the first models. Further, a plurality of second models are calculated, where each second model is a PCR amplification experiment of the second gene is from a serial dilution of the sample and where $N_{BM}$ is taken as a measure of central tendency of the values $N_{BM}$ determined from each of the second models.

In some embodiments, a first aliquot of the sample is used in the serial dilutions of step (A) and a second aliquot of the sample is used in the serial dilutions of step (B). In some embodiments, the serial dilution of step (A) is done in duplicate or triplicate (or some larger number of replicates) and a different first model is computed for each PCR amplification experiment of each dilution, for the first gene, and where $N_{AM}$ is deemed to be a measure of central tendency of the values $N_{AM}$ computed from each of the first models. Further, in some embodiments, the serial dilution of step (B) is done in duplicate or triplicate (or some larger number of replicates) and a different first model is computed for each PCR amplification experiment of each dilution, for the second gene, and where $N_{BM}$ is deemed to be a measure of central tendency of the values $N_{BM}$ computed from each of the second models.

In some embodiments, each PCR amplification experiment in the plurality of PCR amplification experiments represents a serial dilution of the sample, and the method further comprises refining the value $N_{AM}$ calculated for each model in the plurality of first models as a function of relative concentration of the sample prior to the computing step (C) and refining the value $N_{BM}$ calculated for each model in the plurality of second models as a function of relative concentration of the sample prior to the computing step (C). In some embodiments, refinement of $N_{AM}$ comprises performing a weighted regression to minimize mean absolute relative error (ARE) of a plurality of ARE values with respect to $N_{AM}$ calculated by each of the first models, where each $$ARE = \frac{|C_0^{actual} - C_0^{predicted}|}{C_0^{actual}}$$

value in the plurality of ARE values is for a respective first model in the plurality of first models, and where $C_0^{actual}$ is the actual relative concentration of the sample used in a first PCR amplification experiment corresponding to the respective first model and $C_0^{predicted}$ is the calculated relative concentration of the sample used for the first PCR amplification experiment corresponding to the respective first model that is determined by the calculated value $N_{AM}$ for the respective first model. Further, refinement of $N_{BM}$ comprises performing a weighted regression to minimize mean absolute relative error (ARE) of a plurality of ARE values with respect to $N_{BM}$ calculated by each of the second models, where each $$ARE = \frac{|C_0^{actual} - C_0^{predicted}|}{C_0^{actual}}$$

value in the plurality of ARE values is for a respective second model in the plurality of second models, and where $C_0^{actual}$ is the actual relative concentration of the sample used in a second PCR amplification experiment corresponding to the respective second model and $C_0^{predicted}$ is the calculated relative concentration of the sample used for the second PCR amplification experiment corresponding to the respective second model that is determined by the calculated value $N_{AM}$ for the respective second model.

In some embodiments, $N_{AM}$ is a concentration of the mRNA for the first gene in the sample and $N_{BM}$ is a concentration of the mRNA for the first gene in the sample. In some embodiments, $N_{AM}$ is a number of mRNA molecules transcribed from the first gene in the sample and $N_{BM}$ is a number of mRNA molecules transcribed from the second gene in the sample. In some embodiments, the first amplification experiment amplifies mRNA of a first gene and the second amplification experiment amplifies mRNA of a second gene and $N_{AM}$ is a measure of an abundance of the mRNA of the first gene in the sample while $N_{BM}$ is a measure of an abundance of the mRNA of the second gene in the sample. In some embodiments, the first gene is a gene associated with a phenotypic characterization and wherein the second gene is a gene that is not associated with the phenotypic characterization.

In some embodiments, when $\rho$ is above a threshold value, the member of a species that contributed the sample is deemed to have the phenotypic characterization. In some embodiments, when $\rho$ is above a threshold value, the member of a species that contributed the sample is deemed to not have the phenotypic characterization. In some embodiments, when $\rho$ is below a threshold value, the member of a species that contributed the sample is deemed to have the phenotypic characterization. In some embodiments, when p is below a threshold value, the member of a species that contributed the sample is deemed to not have the phenotypic characterization.

In some embodiments, the phenotypic characterization is a cell type, a cell morphology, a disease state, an abnormal state in a tissue or organ, an abnormal cell type, or an abnormal cell morphology. In some embodiments, the initial amount of a target nucleic acid $N_0$ in the sample is a concentration of the mRNA of a first gene in the sample. In some embodiments, the initial amount of a target nucleic acid $N_0$ in the sample is a number of mRNA molecules transcribed from a first gene in the sample. In some embodiments, the method further comprises (D) outputting $\rho$ to a user interface device, a monitor, a computer-readable storage medium, a computer-readable memory, or a local or remote computer system; or displaying $\rho$.

Another aspect of the present invention provides a polymerase chain reaction (PCR) system comprising a PCR analysis module that generates a first plurality of fluorescent measurements, where each respective fluorescent measurement FS, in the first plurality of fluorescent measurements is a fluorescent measurement taken in a different cycle n in a first PCR amplification experiment of a sample. The PCR system further comprises an intelligence module adapted to process the first plurality of fluorescent measurements by calculating a model for the first PCR amplification experiment that provides an estimate of the initial amount $N_0$ of a target nucleic acid in the sample. For each respective fluorescent measurement in the first plurality of fluorescent measurements, the model comprises a respective equation for $N_n$, where (i) $N_n$ is the calculated amount of the target nucleic acid in cycle n of the first PCR amplification experiment from which the respective fluorescent measurement was taken, and (ii) the respective equation for $N_n$ is expressed only in terms of K and $N_0$, regardless of the cycle n of the first PCR amplification experiment, where K is the Michaelis-Menten constant for the first PCR amplification experiment and $N_0$ is an initial amount of a target nucleic acid in the sample. In some embodiments, the model is refined. For example, the model can be refined by adjusting K and $N_0$ until differences between values $N_n$ computed by the model and corresponding fluorescent measurements in the first plurality of fluorescent measurements are minimized, thereby determining an initial amount of a target nucleic acid $N_0$ in the sample. In some embodiments, the intelligence module further comprises instructions for outputting $N_0$ to a user interface device, a monitor, a computer-readable storage medium, a computer-readable memory, or a local or remote computer system; or displaying $N_0$.

Another aspect of the present invention provides a computer system for calculating an initial amount of a target nucleic acid $N_0$ in a sample, the computer system comprising a processor and a memory, coupled to the processor, the memory storing a module comprising instructions for receiving a first plurality of fluorescent measurements, where each respective fluorescent measurement $FS_n$ in the first plurality of fluorescent measurements is a fluorescent measurement taken in a different cycle n in a first PCR amplification experiment of the sample. The memory further stores instructions for calculating a model for the first PCR amplification experiment that provides an estimate of the initial amount $N_0$ of a target nucleic acid, where, for each respective fluorescent measurement in the first plurality of fluorescent measurements, the model comprises a respective equation for $N_n$. Here, (i) $N_n$ is the calculated amount of the target nucleic acid in cycle n of the first PCR amplification experiment from which the respective fluorescent measurement was taken, and (ii) the respective equation for $N_n$ is expressed only in terms of K and $N_0$, regardless of the cycle n of the first PCR amplification experiment, wherein K is the Michaelis-Menten constant for the first PCR amplification experiment. In some embodiments the model is refined. For example, the model can be refined by adjusting K and $N_0$ until differences between values $N_n$ computed by the model and corresponding fluorescent measurements in the first plurality of fluorescent measurements are minimized, thereby calculating the initial amount of a target nucleic acid $N_0$ as the minimized value for $N_0$ for the model. In some embodiments, the module further comprises instructions for outputting the calculated initial amount of a target nucleic acid $N_0$ to a user interface device, a monitor, a computer-readable storage medium, a computer-readable memory, or a local or remote computer system; or displaying the calculated initial amount of a target nucleic acid $N_0$.

Another aspect of the present invention provides a computer-readable medium storing a computer program, executable by a computer, to calculate an initial amount of a target nucleic acid $N_0$ in a sample. The computer program comprises (A) instructions for receiving a first plurality of fluorescent measurements, where each respective fluorescent measurement $FS_n$ in the first plurality of fluorescent measurements is a fluorescent measurement taken in a different cycle n in a first PCR amplification experiment of the sample. The computer program further comprises (B) instructions for calculating a first model for the first PCR amplification experiment that provides an estimate of the initial amount $N_0$ of a target nucleic acid, where, for each respective fluorescent measurement in the first plurality of fluorescent measurements, the first model comprises a respective equation for $N_n$, where (i) $N_n$ is the calculated amount of the target nucleic acid in cycle n of the first PCR amplification experiment from which the respective fluorescent measurement was taken, and (ii) the respective equation for $N_n$ is expressed only in terms of K and $N_0$, regardless of the cycle n of the first PCR amplification experiment, where K is the Michaelis-Menten constant for the first PCR amplification experiment. In some embodiments, the model is refined. For example, the model can be refined by adjusting K and $N_0$ until differences between values $N_n$ computed by the first model and corresponding fluorescent measurements in the first plurality of fluorescent measurements are minimized, thereby calculating the initial amount of a target nucleic acid $N_0$ as the minimized value for $N_0$ for the first model. In some embodiments, the computer program product further comprises instructions for outputting the calculated initial amount of a target nucleic acid $N_0$ to a user interface device, a monitor, a computer-readable storage medium, a computer-readable memory, or a local or remote computer system; or displaying the calculated initial amount of a target nucleic acid $N_0$.

Another aspect of the invention comprises a computer data signal representing a program for controlling a computer to execute instructions for receiving a first plurality of fluorescent measurements, where each respective fluorescent measurement $FS_n$ in the first plurality of fluorescent measurements is a fluorescent measurement taken in a different cycle n in a first PCR amplification experiment of a sample. The program further comprises instructions for calculating a first model for the first PCR amplification experiment that provides an estimate of the initial amount $N_0$ of a target nucleic acid, where, for each respective fluorescent measurement in the first plurality of fluorescent measurements, the first model comprises a respective equation for $N_n$. Here, (i) $N_n$ is the calculated amount of the target nucleic acid in cycle n of the first PCR amplification experiment from which the respective fluorescent measurement was taken, and (ii) the respective equation for $N_n$ is expressed only in terms of K and $N_0$, regardless of the cycle n of the first PCR amplification experiment, wherein K is the Michaelis-Menten constant for the first PCR amplification experiment. In some embodiments, the model is refined. For example, the model can be refined by adjusting K and $N_0$ until differences between values $N_n$ computed by the first model and corresponding fluorescent measurements in the first plurality of fluorescent measurements are minimized, thereby calculating an initial amount of a target nucleic acid $N_0$ as the minimized value for $N_0$ for the first model. In some embodiments, the program further controls a computer to execute instructions for outputting the calculated initial amount of a target nucleic acid $N_0$ to a user interface device, a monitor, a computer-readable storage medium, a computer-readable memory, or a local or remote computer system; or displaying the calculated initial amount of a target nucleic acid $N_0$.

In general, any of the models in the present invention can be refined. In some embodiments, such models are not refined, but rather values for K and $N_0$ are identified by a complete search for all possible values for K and $N_0$. In such a complete search, the values K and $N_0$ identified from the complete search should provide the best agreement for the values $N_n$ computed by the first model for each of the values of n used in the model. When refinement is used to refine a model, any refining technique including, but not limited to, regression, least squares, a stochastic method (e.g., simulated annealing, genetic algorithms) or linear discriminant functions can be used. See, for example, Duda et al. *Pattern Classification*, 2$^{nd}$ ed., John Wiley & Sons, New York, 2001, and Hastie et al., *The Elements of Statistical Learning*, Springer-Verlag, 2001, each of which is hereby incorporated by reference herein in its entirety for their teachings of model refinement methods.

4 BRIEF DESCRIPTION OF THE DRAWINGS

Figure 1:
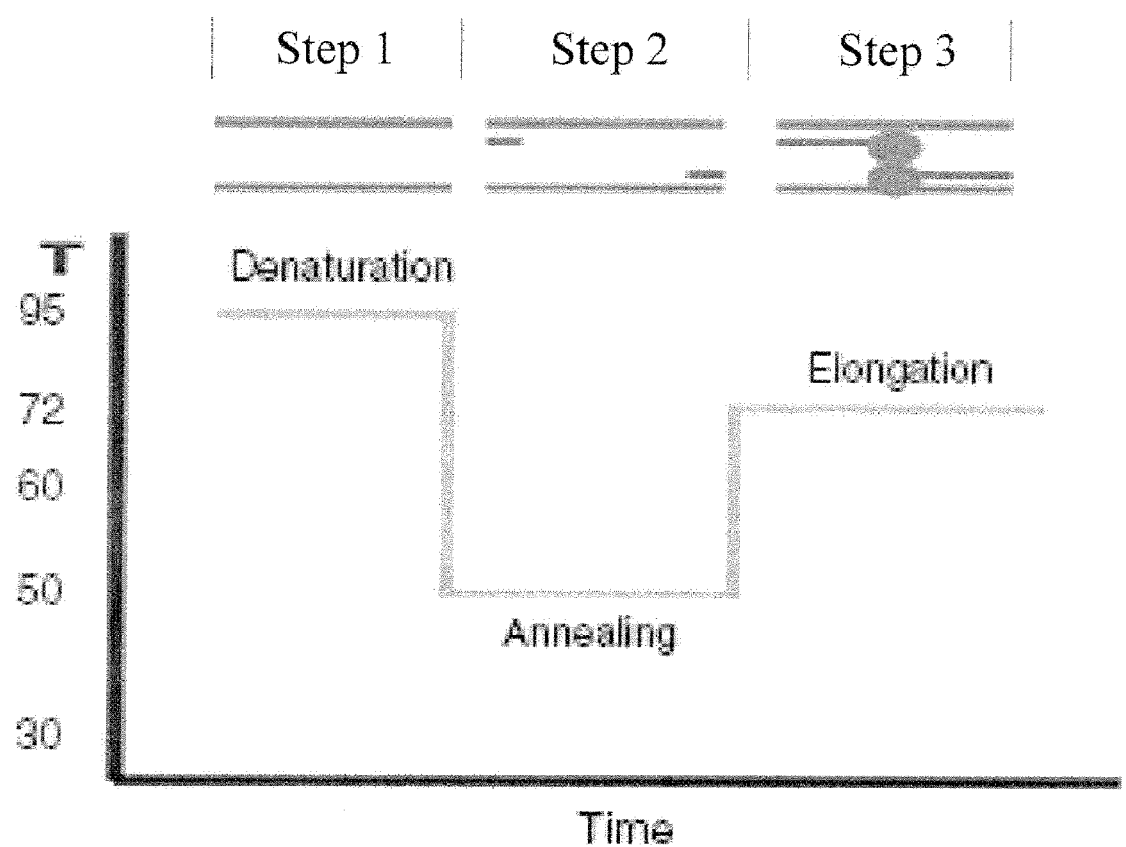
FIG. 1 illustrates the steps of the real-time polymerase chain reaction (PCR) in accordance with the prior art.
Figure 2:
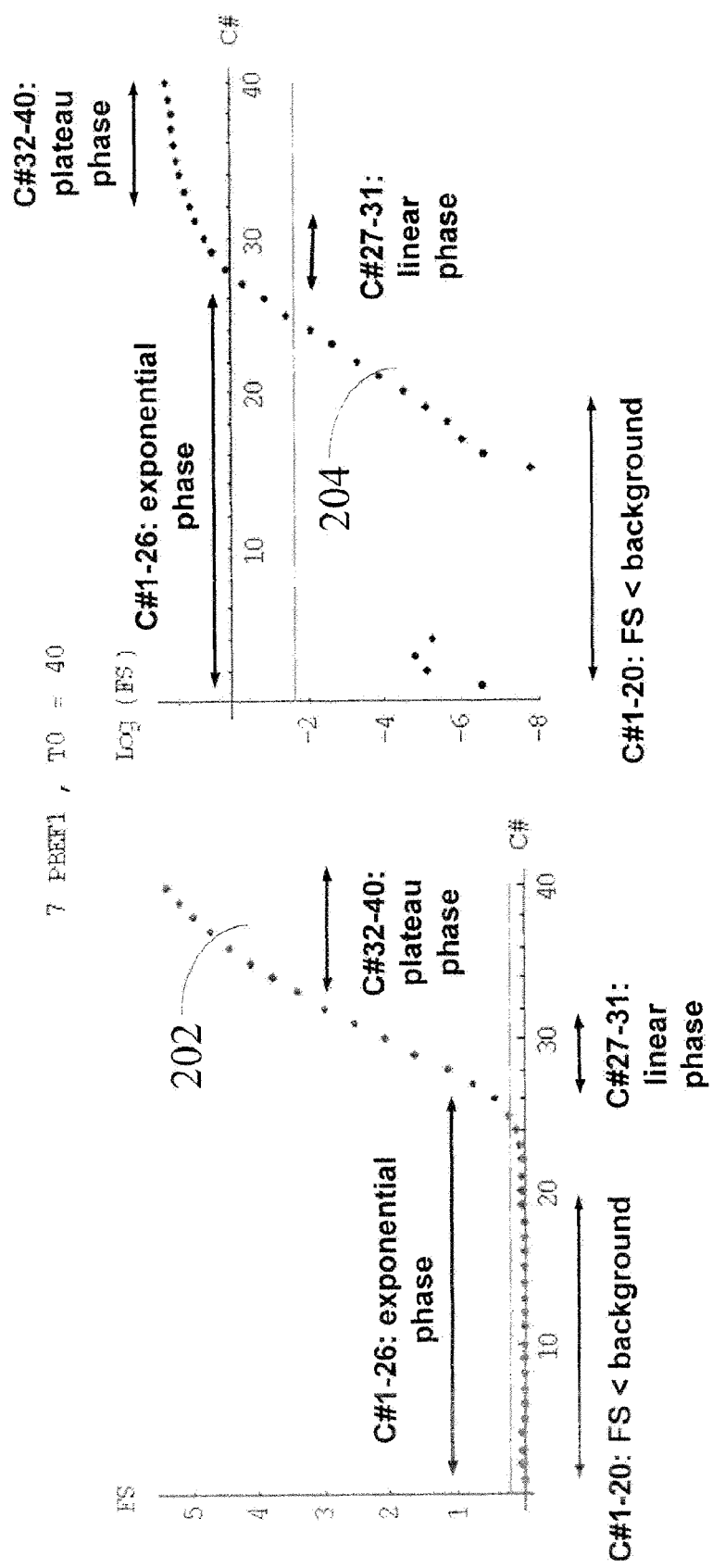
FIG. 2 illustrates the fluorescent signal that is measured after each cycle in a real-time PCR experiment on an absolute scale and a logarithmic scale.
Figure 3:
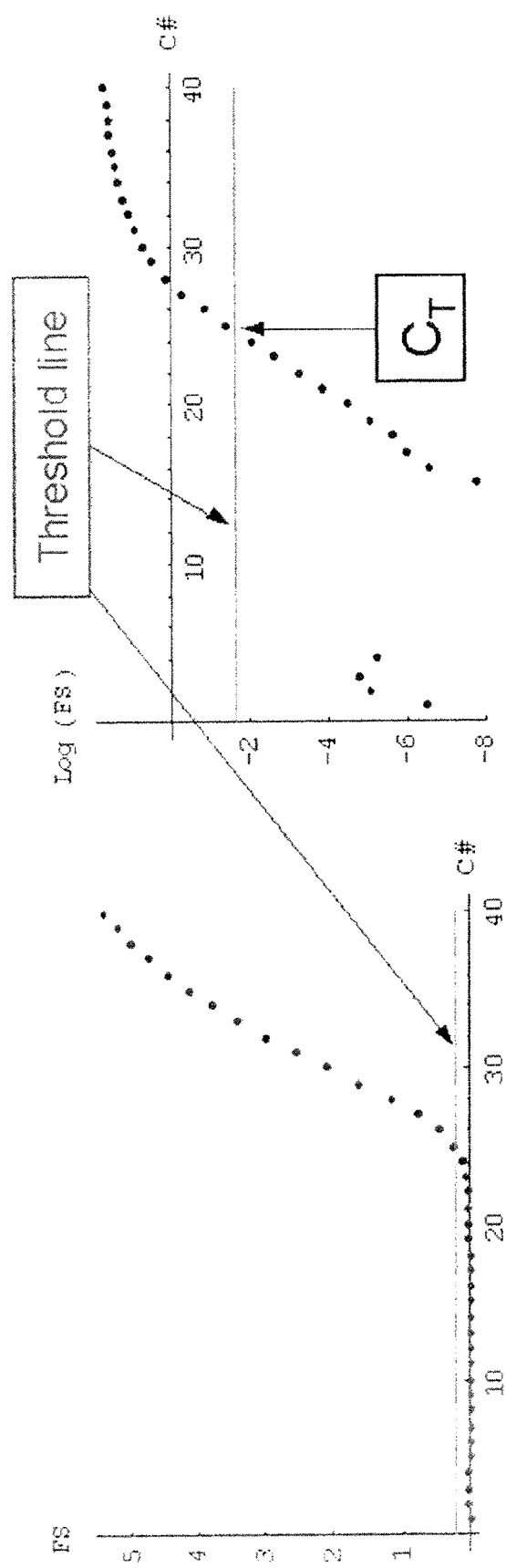
FIG. 3 illustrates the establishment of a threshold line T and the determination of the number of real-time PCR cycles (CT) that are required to achieve a fluorescent signal that is equal to or greater than T.
Figure 4:
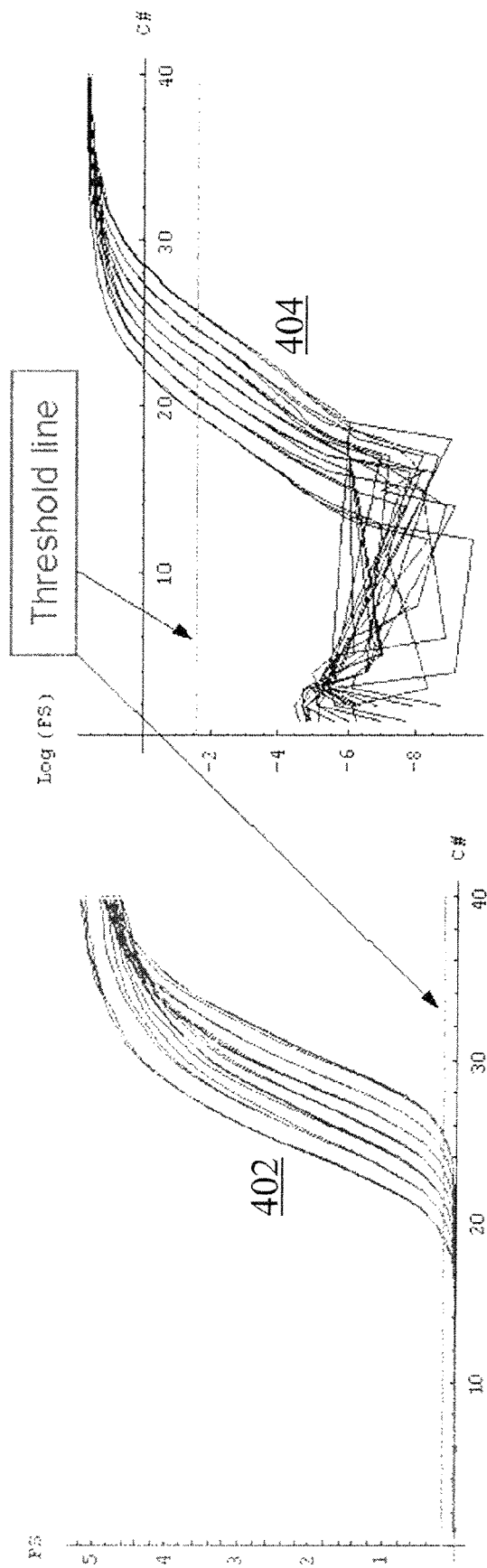
FIG. 4 illustrates quantitative PCR amplification curves on both the linear and logarithmic scale that represent a serial dilution of an initial sample of PBEF1.
Figure 5:
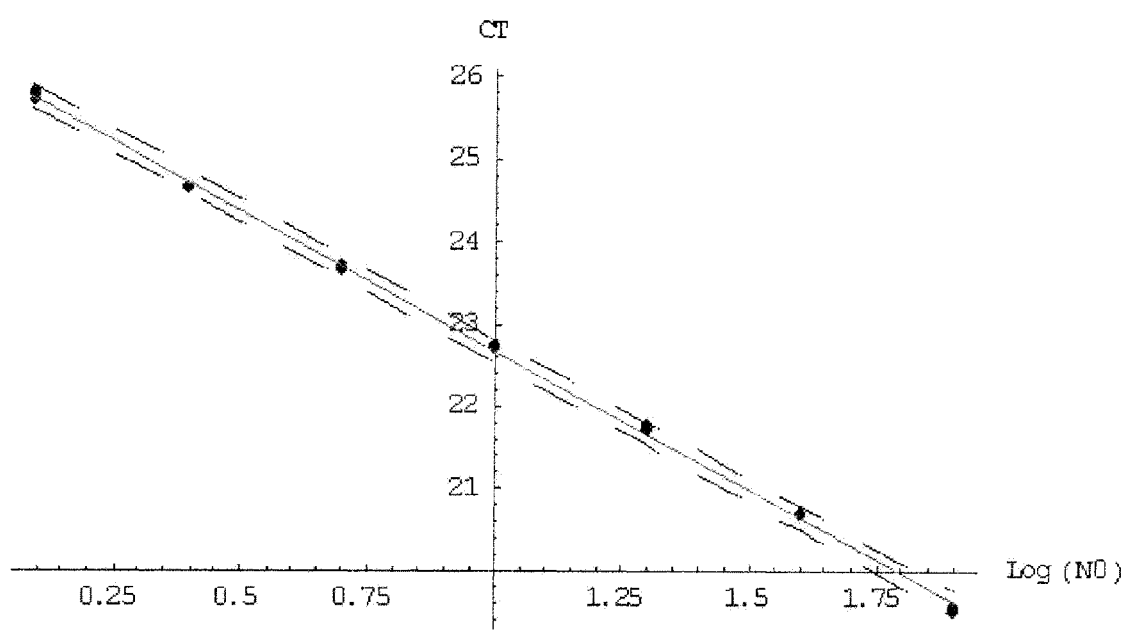
FIG. 5 illustrates computation of a standard curve for PBEF1 from the amplification curves of FIG. 4, where the standard curve plots CT, the number of cycles necessary to achieve a fluorescent signal greater than T, as a function of $Log(N_0)$, where $N_0$ is the concentration of the initial template nucleic acid.
Figure 6:
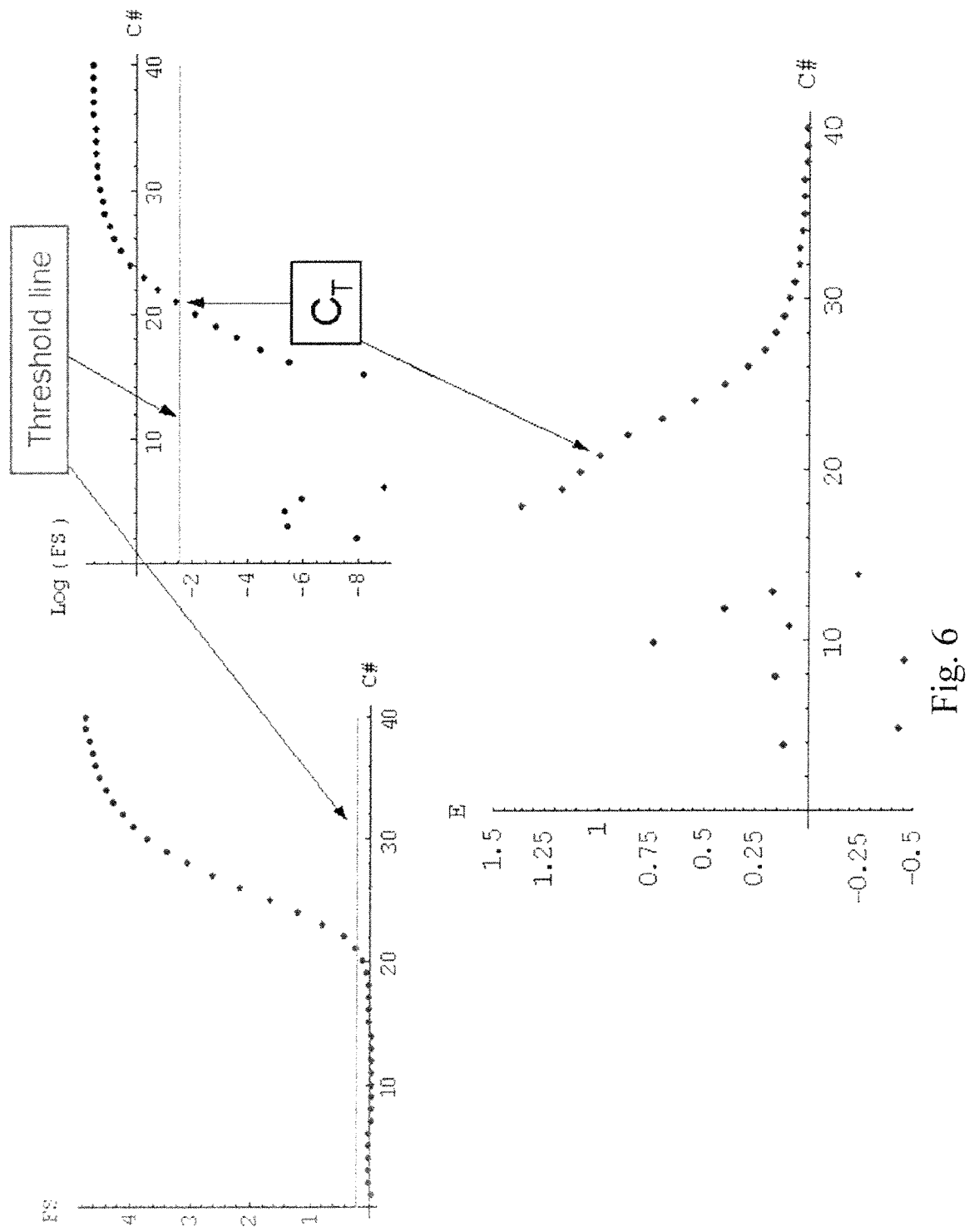
FIG. 6 illustrates the local efficiency $E_n$ of each cycle in a PCR experiment for gene PBEF1.
Figure 7:
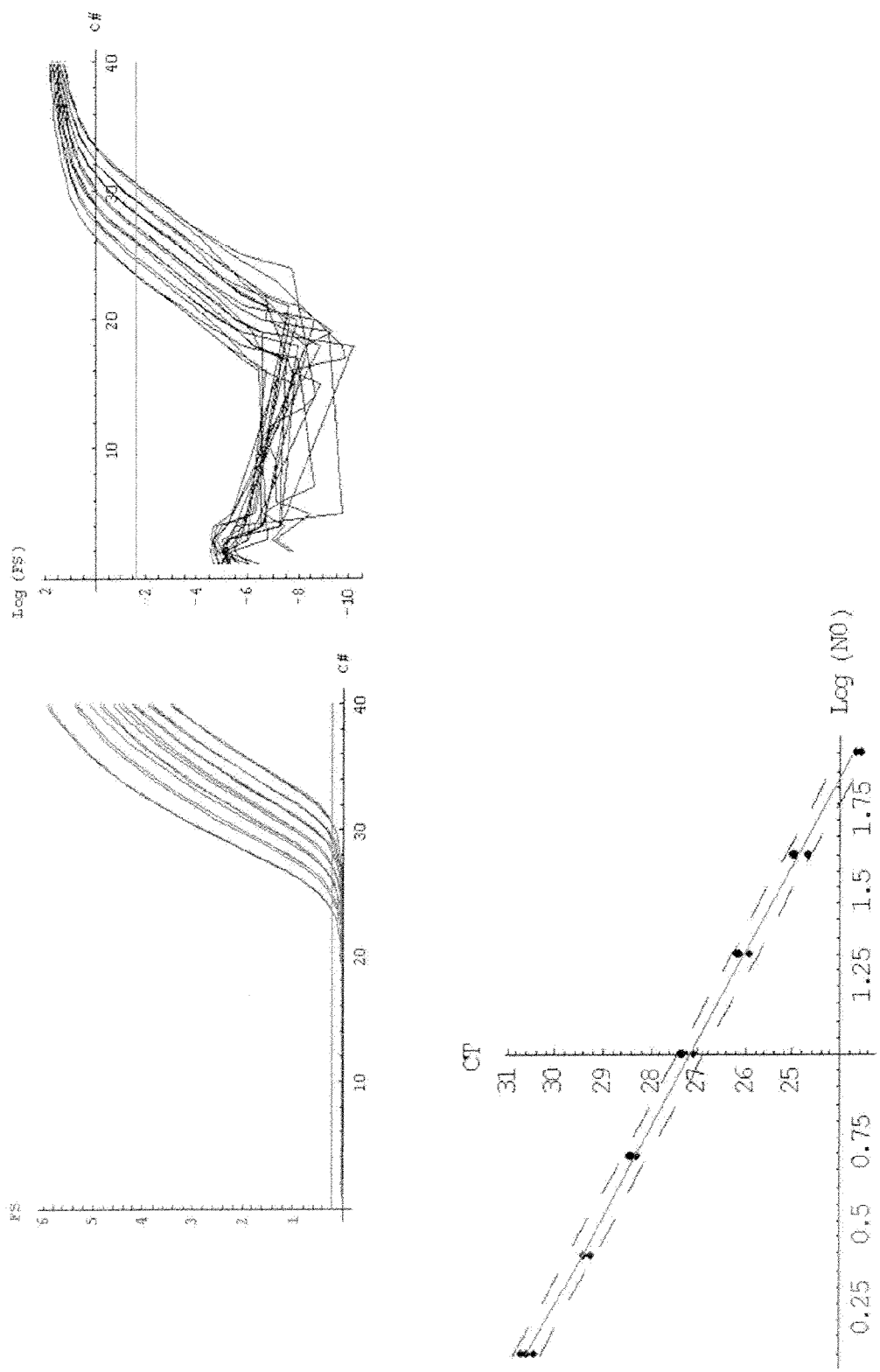
FIG. 7 illustrates quantitative PCR amplification curves on both the linear and logarithmic scale that represent a serial dilution of an initial sample of IFNAR1, and a standard curve for IFNAR1 from the IFNAR1 amplification curves.
Figure 8:
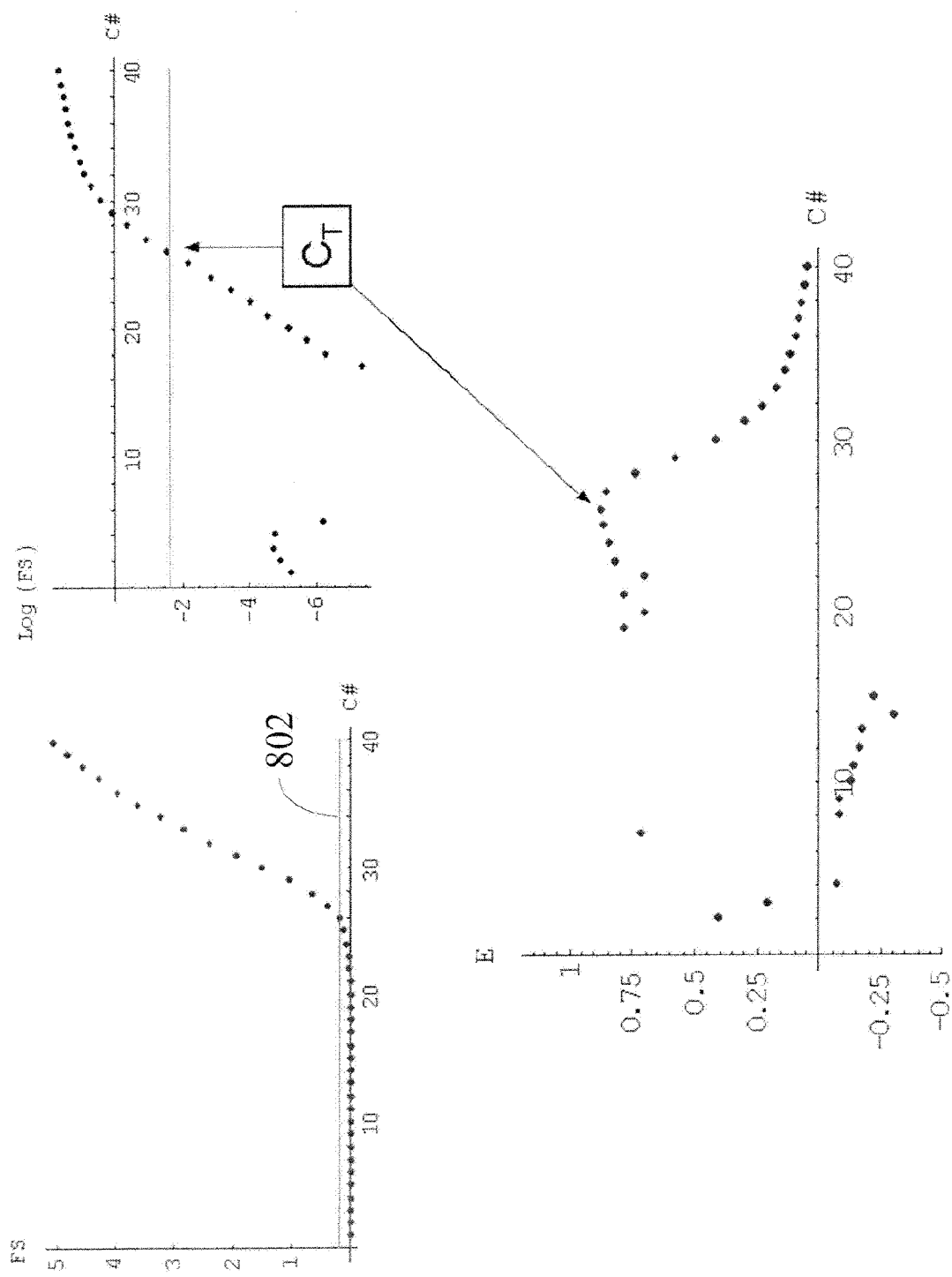
FIG. 8 illustrates the local efficiency $E_n$ of each cycle in a PCR experiment for gene IFNAR1.
Figure 9:
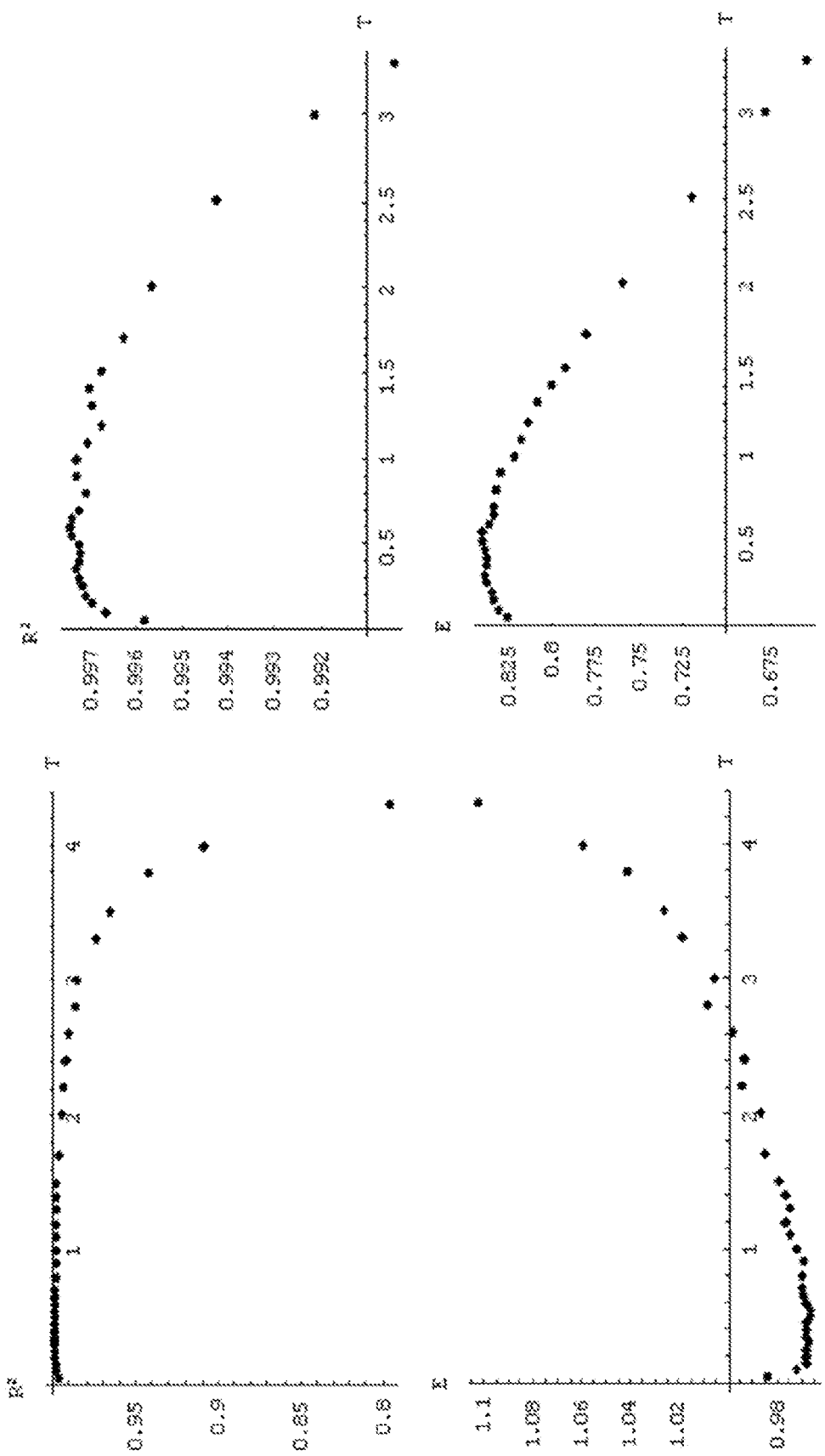
FIG. 9 illustrates variance in the estimated efficiency of a PCR reaction as a function of placement of threshold value T for PBEF1 and IFNAR1 data.
Figure 10:
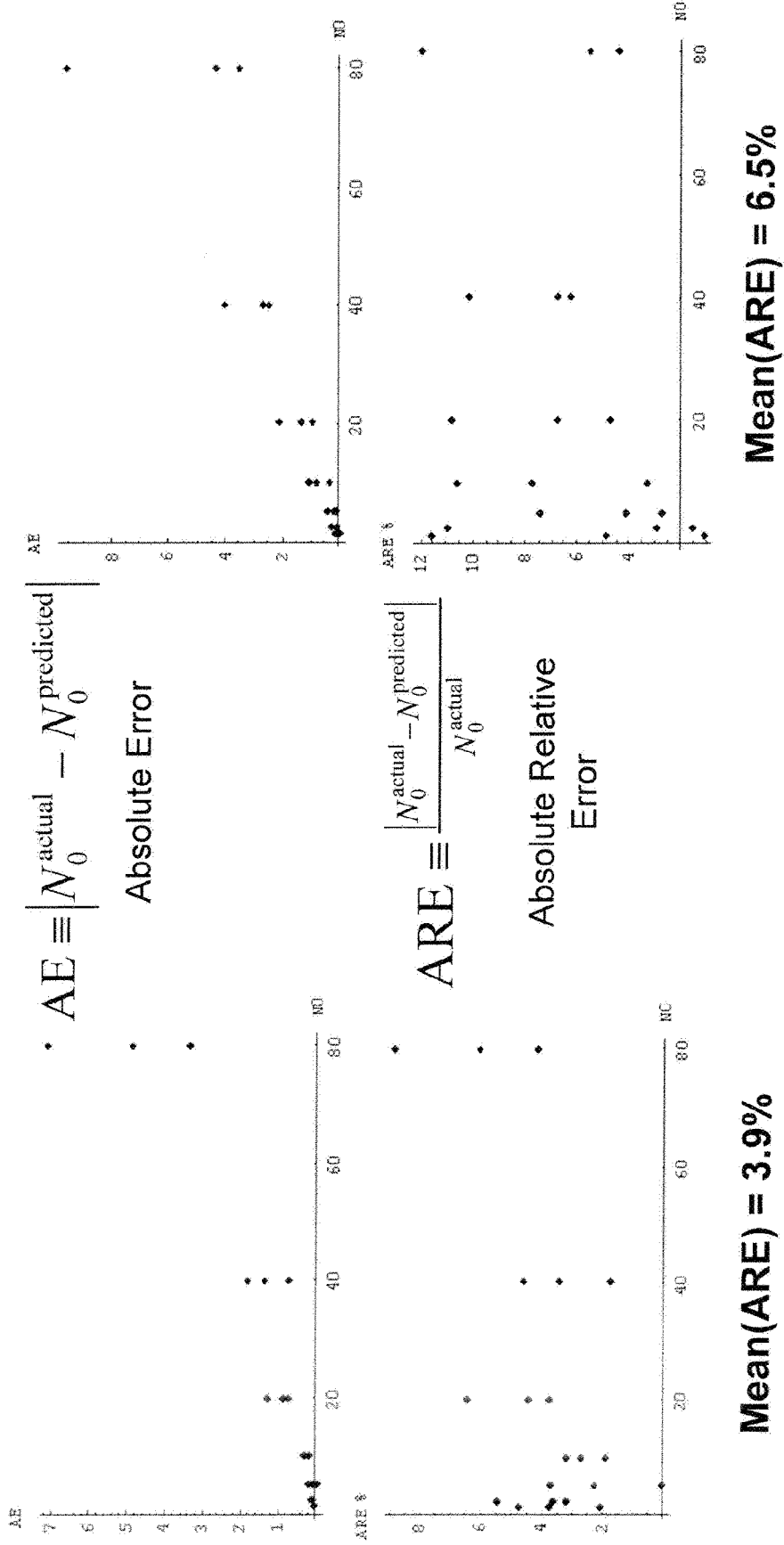

FIG. 10 defines absolute error AE and absolute relative error ARE in the prediction of the starting amount of a target nucleic acid in a quantitative PCR sample when the actual starting amount of target nucleic acid in the quantitative PCR sample is known.

Figure 11:
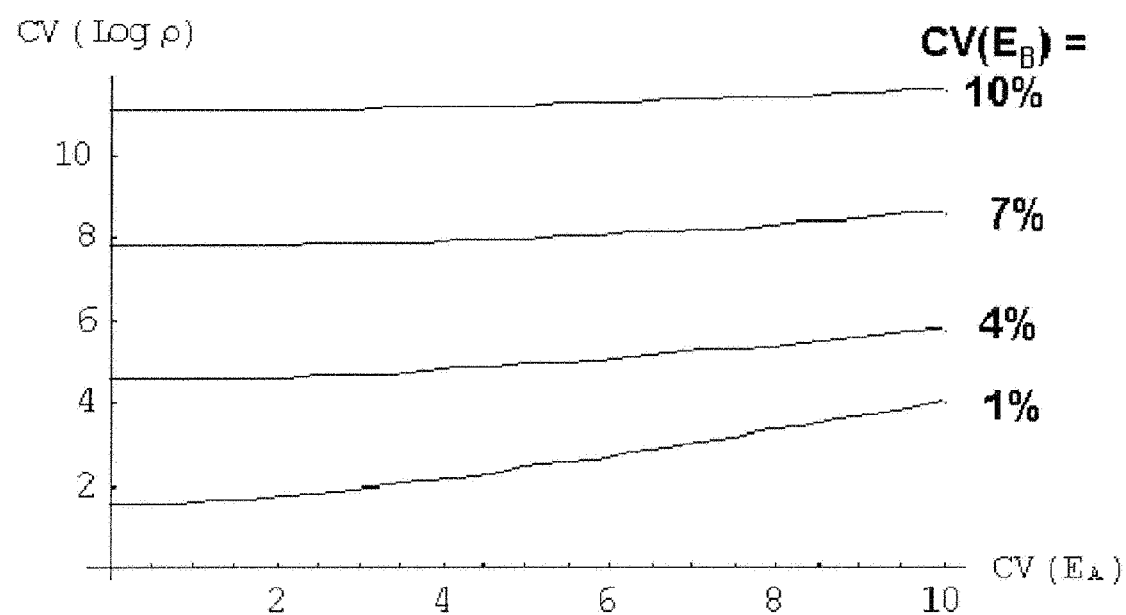
Figure 11:
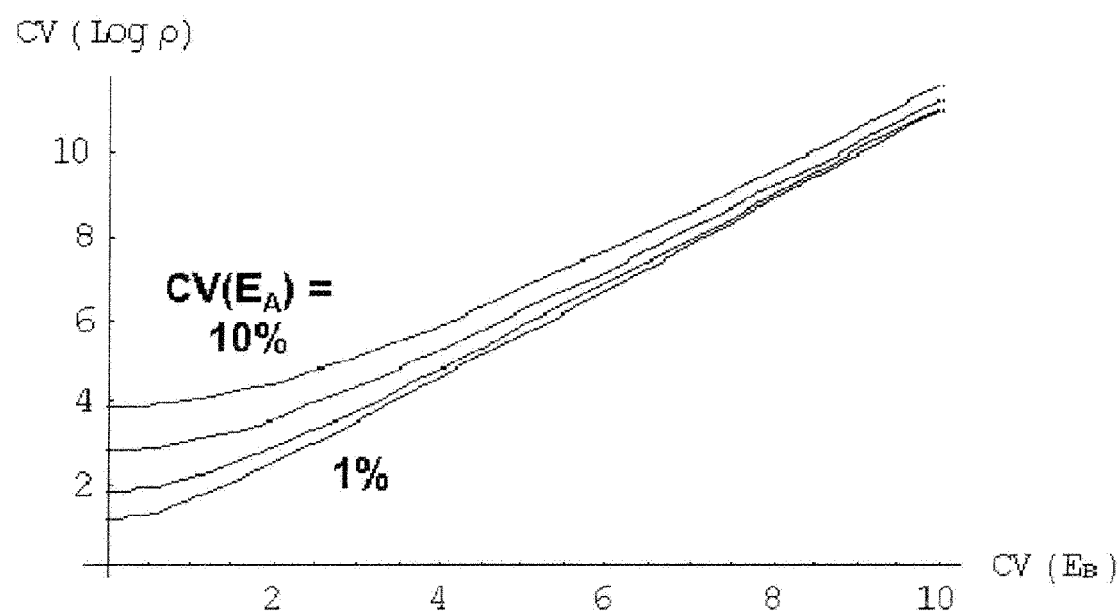

FIG. 11 illustrates how variation in the error of PCR efficiencies of genes with different values for CT affect the magnitude of the error in $Log_{10}\rho$.

Figure 12:
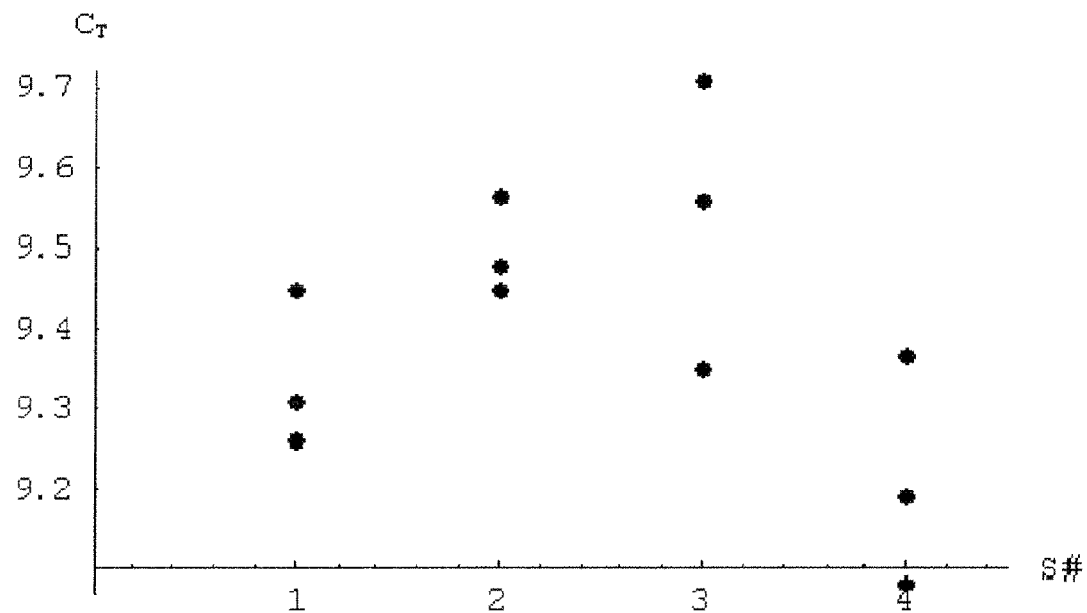

FIG. 12 illustrates $C_T$ values of the reference gene 18S for four different samples with three replicates for each sample.

Figure 13:
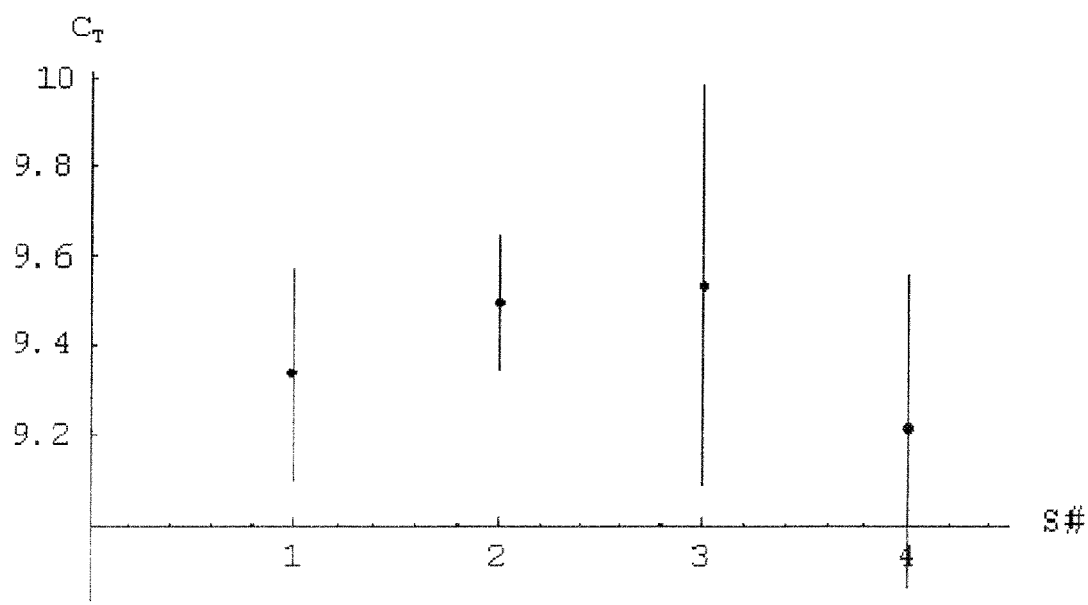

FIG. 13 illustrates mean $C_T$ for the reference gene 18S and their 95 percent confidence intervals (CI) based on three replicates.

Figure 14:
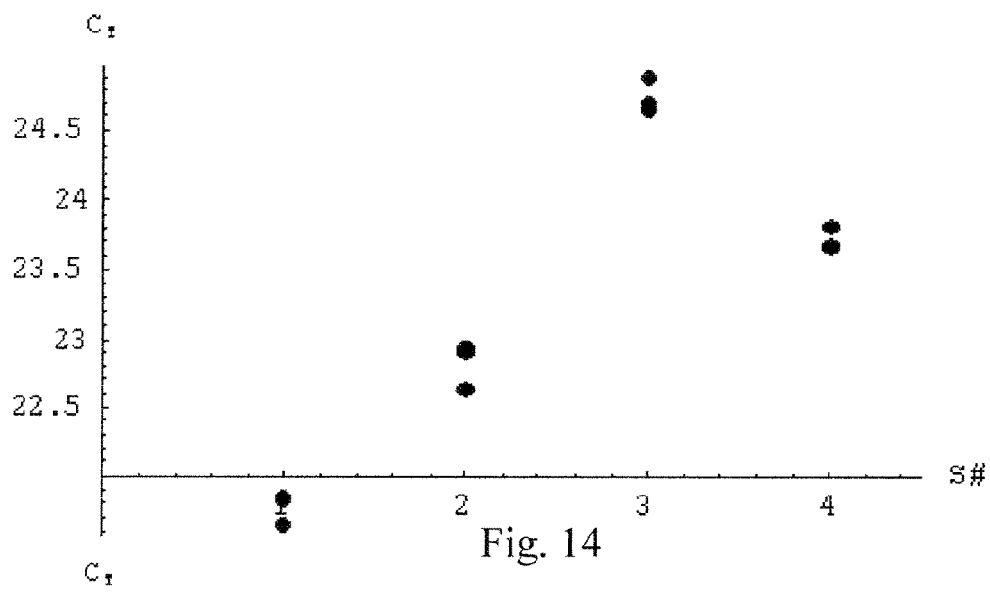

FIG. 14 illustrates $C_T$ values of a gene that is expressed, PBEF1, for four different samples with three replicates for each sample.

Figure 15:
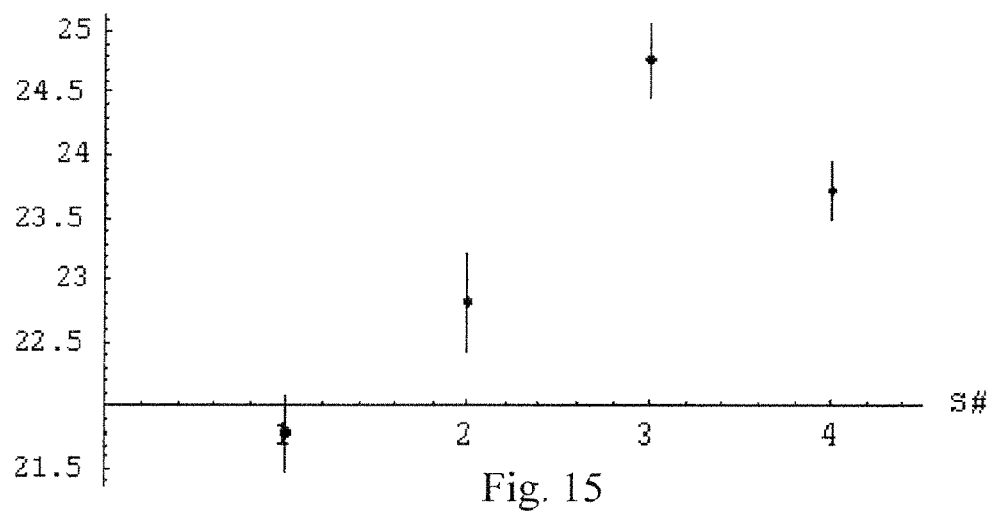

FIG. 15 illustrates mean $C_T$ values for the gene PBEF1 and their 95 percent confidence intervals based on three replicates.

Figure 16:
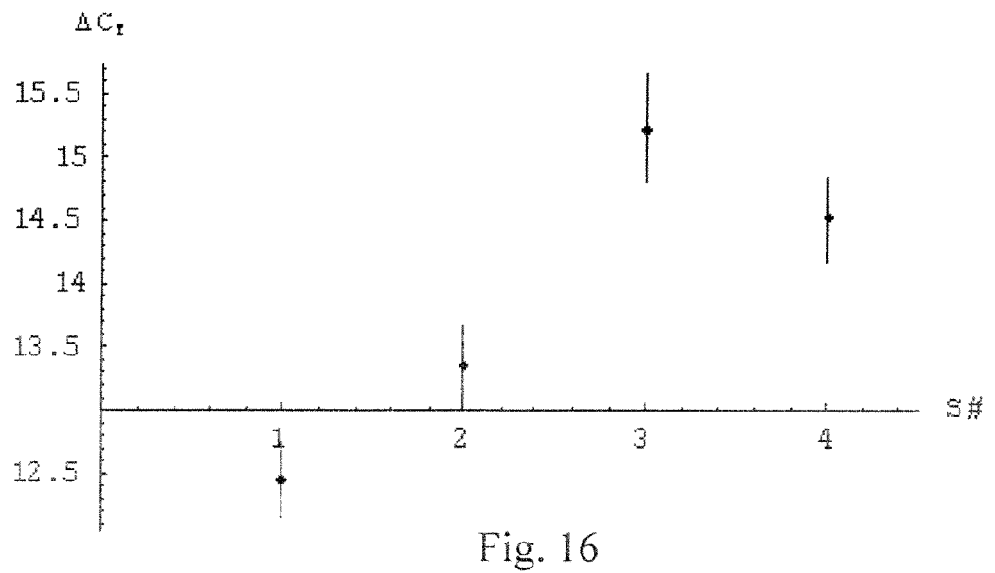

FIG. 16 illustrates the means of $\Delta C_T \equiv CT_{PBEF1} - CT_{18S}$.

Figure 17:
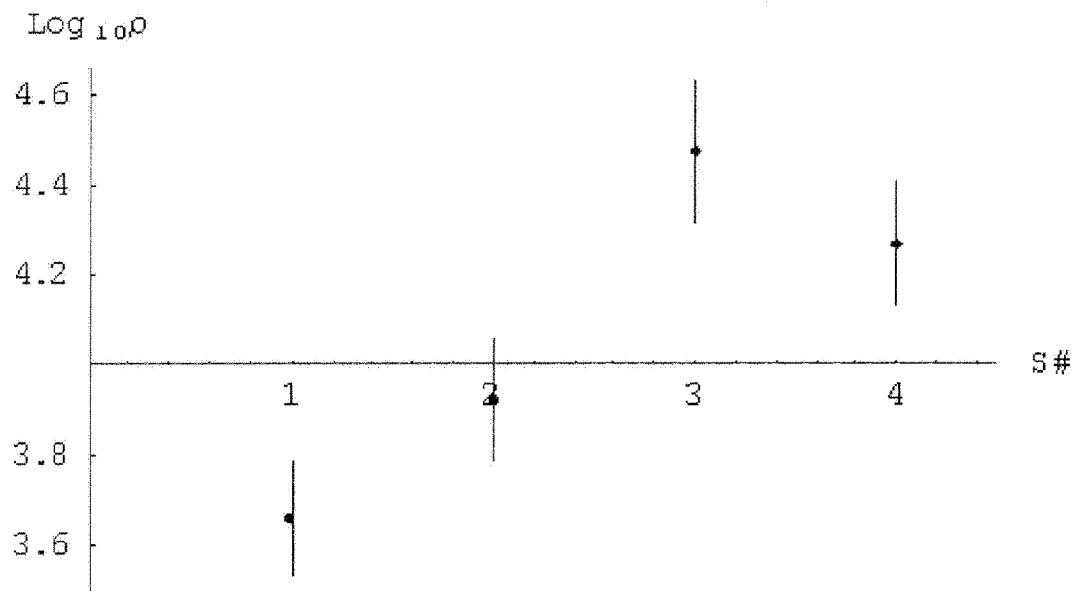

FIG. 17 illustrates $Log_{10}\rho$ for the ratio $N_{18S}/N_{PBEF1}$ assuming that $E_{PBEF1}$ and $E_{18S}$ do no vary.

Figure 18:
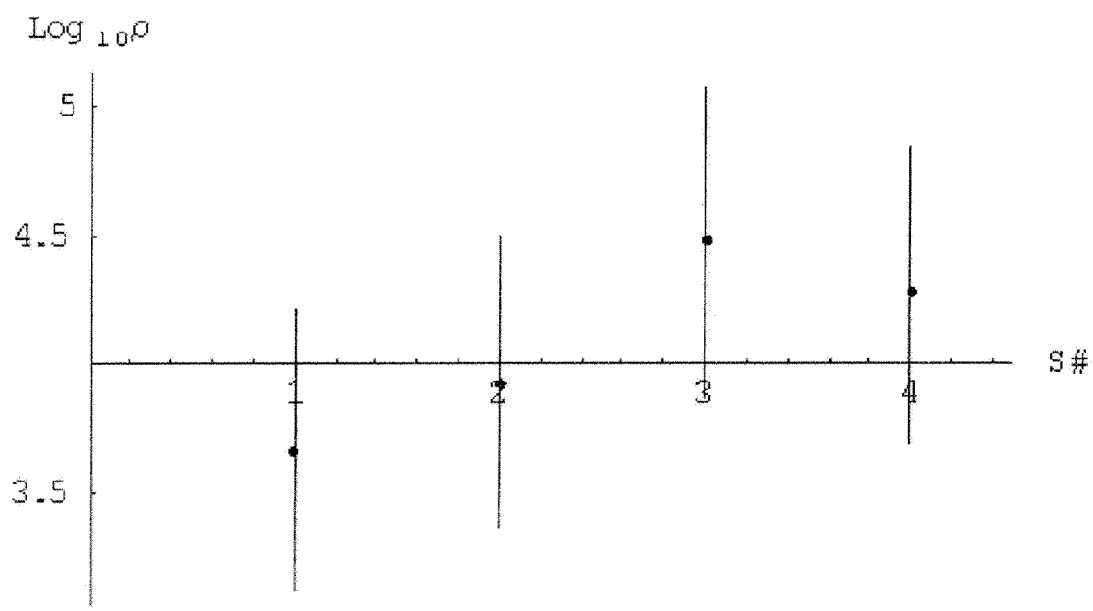

FIG. 18 illustrates confidence intervals of $Log_{10}\rho$ for the ratio $N_{18S}/N_{PBEF1}$ when typical variability of $E_{PBEF1}$ and $E_{18S}$ from sample to sample is taken into account.

Figure 19:
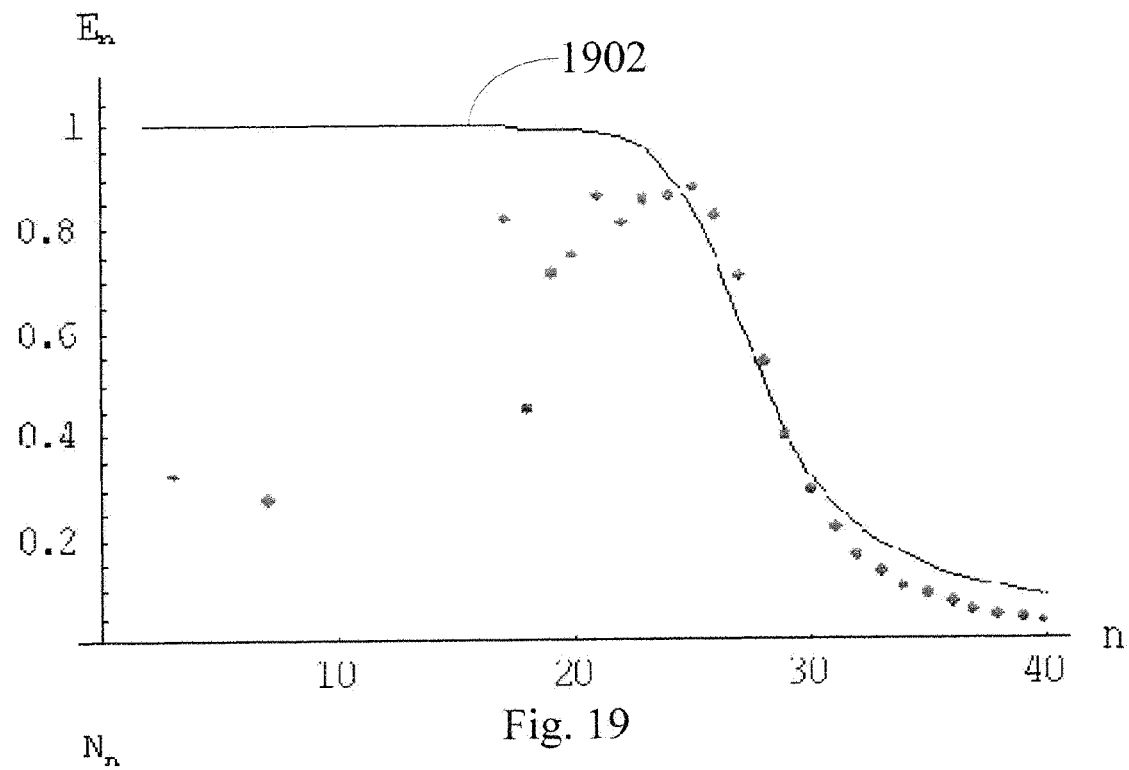

FIG. 19 illustrates local efficiency as a function of PCR cycle number using a model based on Michaelis-Menten kinetics.

Figure 20:
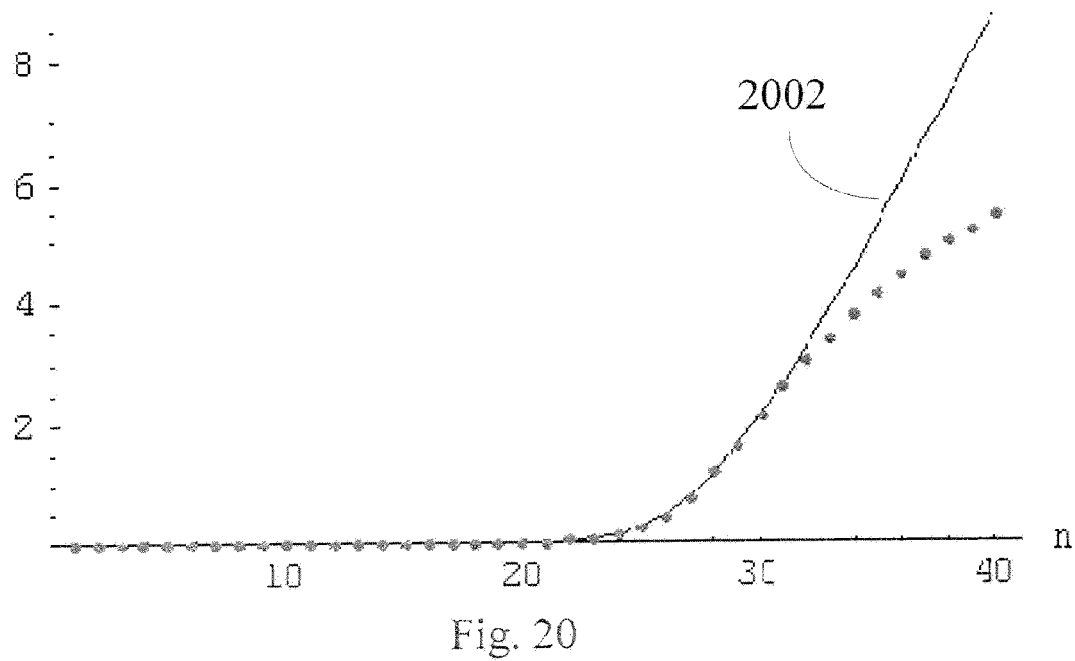

FIG. 20 illustrates the amount of target nucleic acid in a sample as a function of PCR cycle number using a model based on Michaelis-Menten kinetics.

Figure 21:
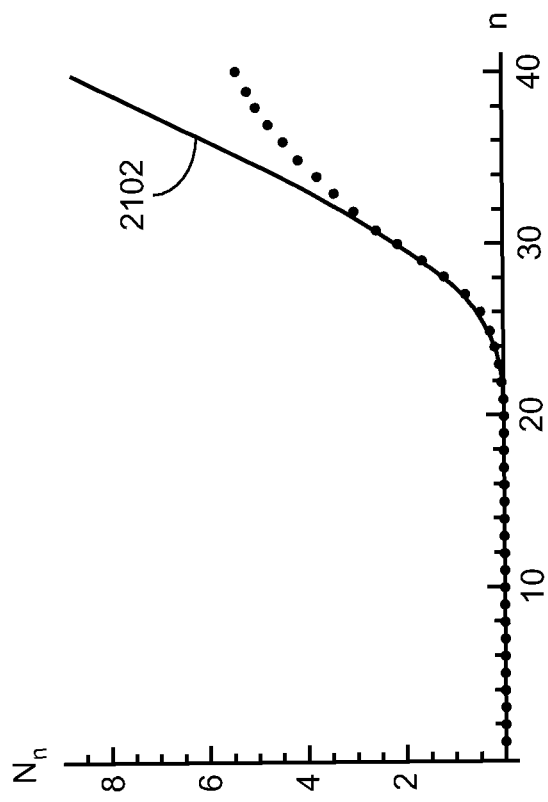

FIG. 21 illustrates the computation of $N_n$ as a function of PCR cycle number n using a model based on Michaelis-Menten kinetics.

Figure 22:
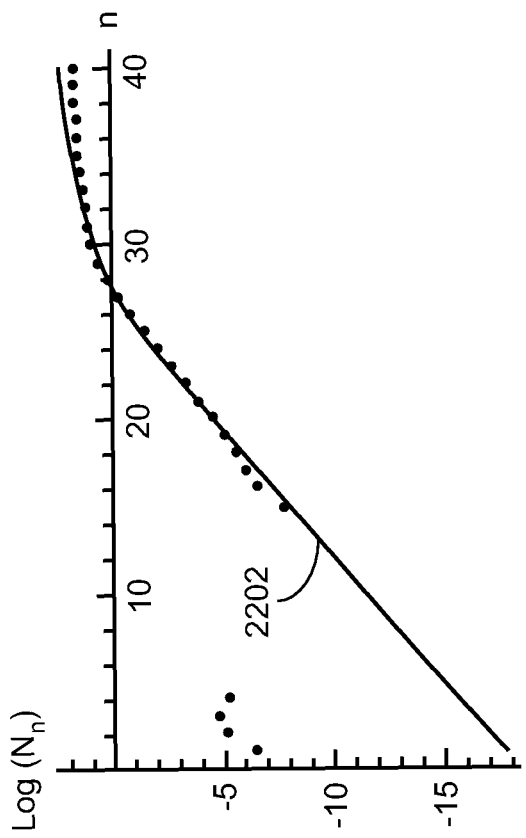

FIG. 22 illustrates the computation of $Log(N_n)$ as a function of PCR cycle number n using a model based on Michaelis-Menten kinetics.

Figure 23:
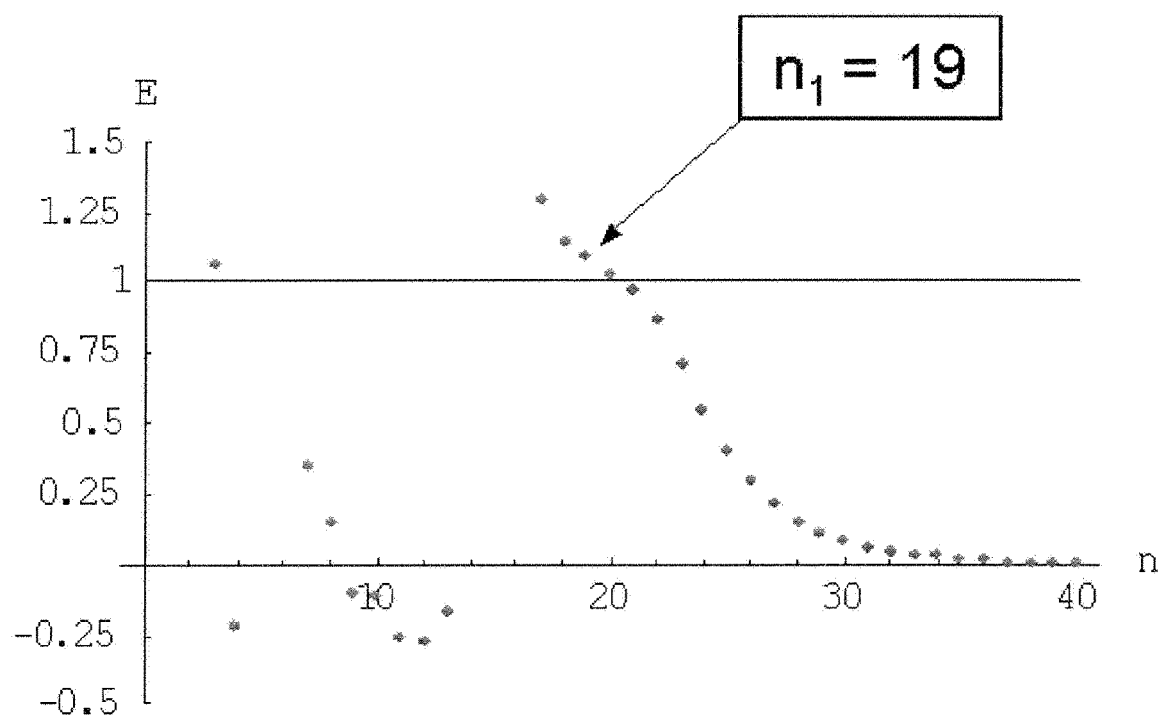

FIG. 23 illustrates how the first PCR cycle $n_{start}$ chosen for fitting the parameters $N_0$ and K is selected in accordance with an embodiment of the present invention.

Figure 24:
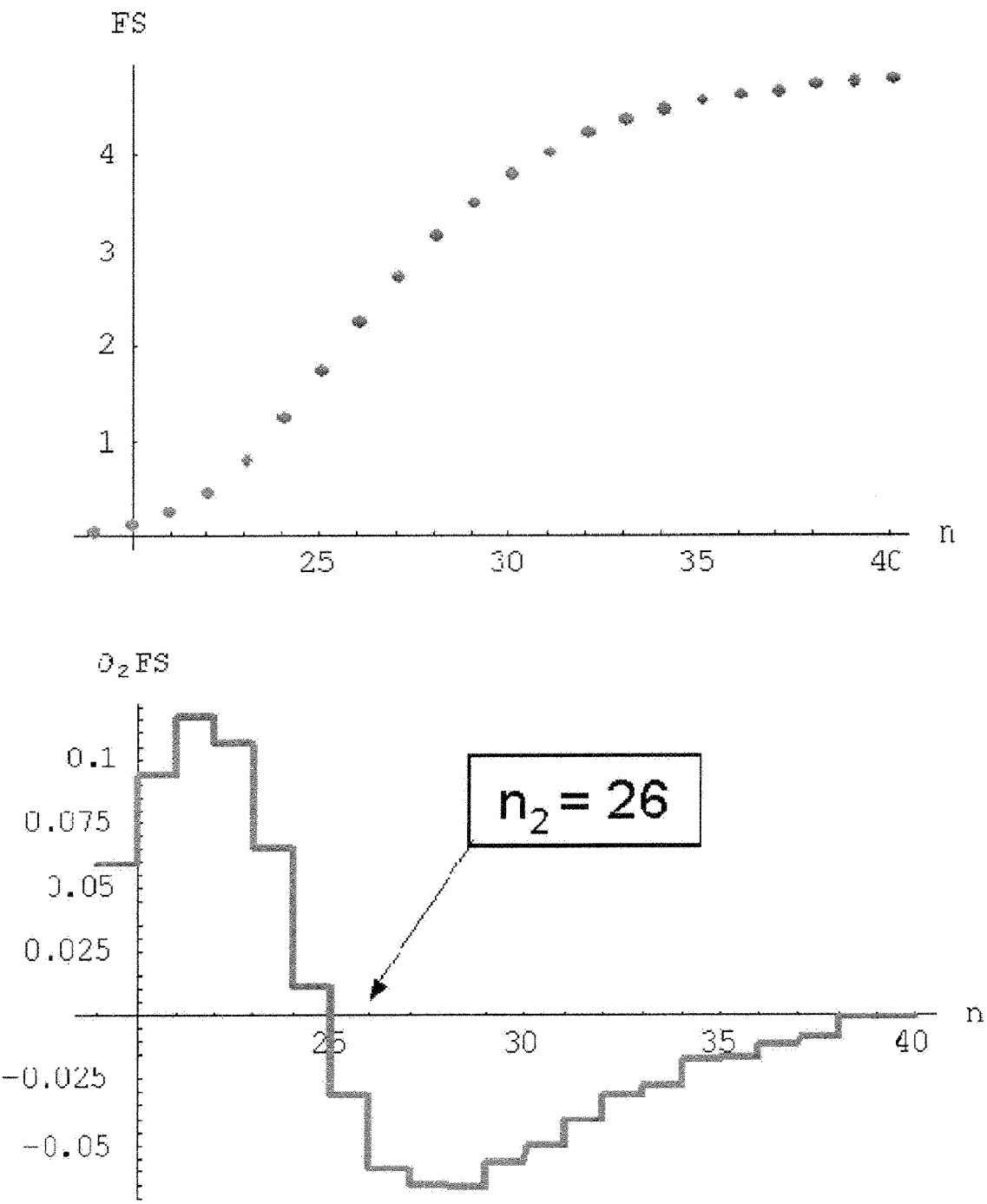

FIG. 24 illustrates how the last PCR cycle $n_{end}$ chosen for fitting the parameters $N_0$ and K is selected in accordance with an embodiment of the present invention.

Figure 25:
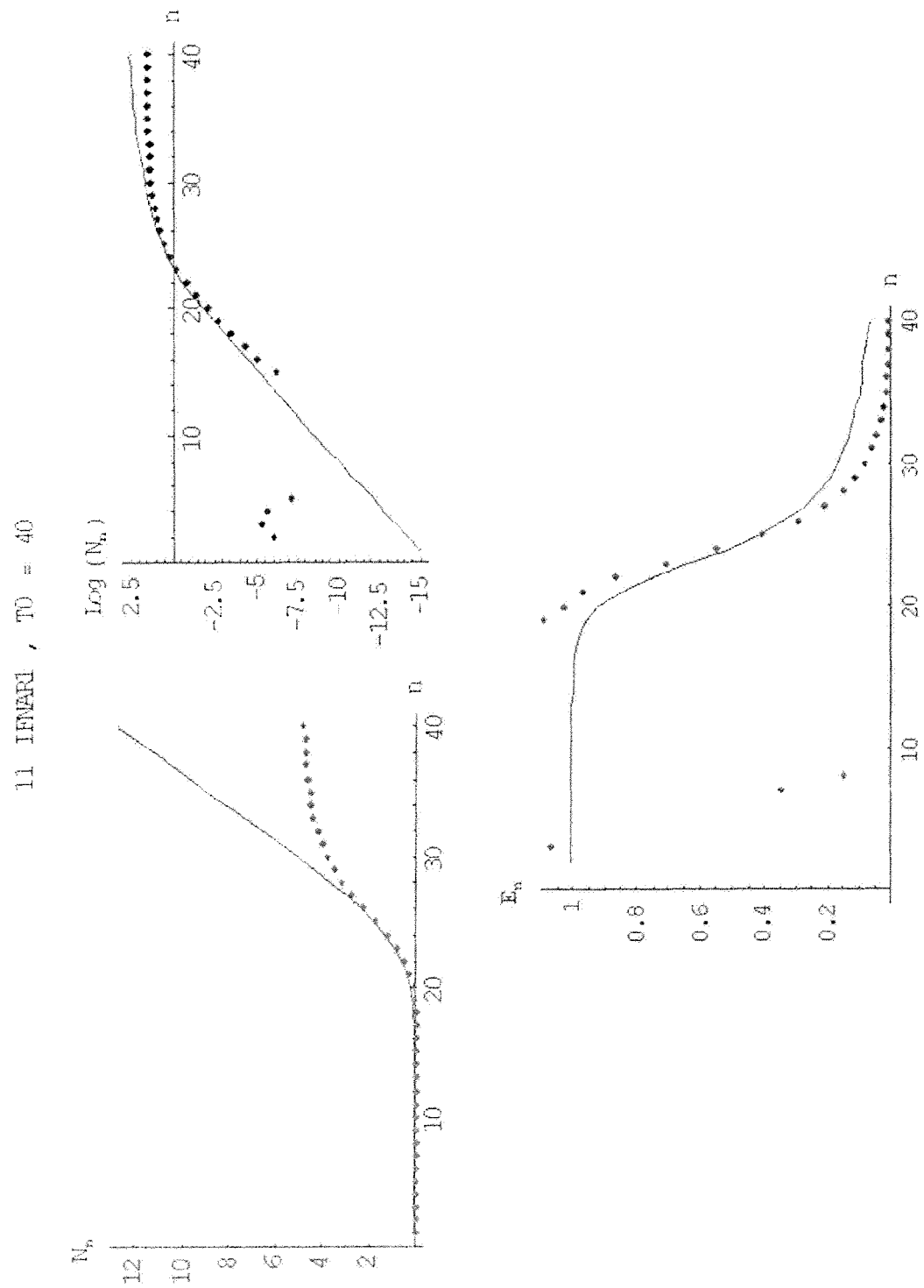

FIG. 25 illustrates a PCR amplification curve that was analyzed using a model based upon Michaelis-Menten kinetics.

Figure 26:
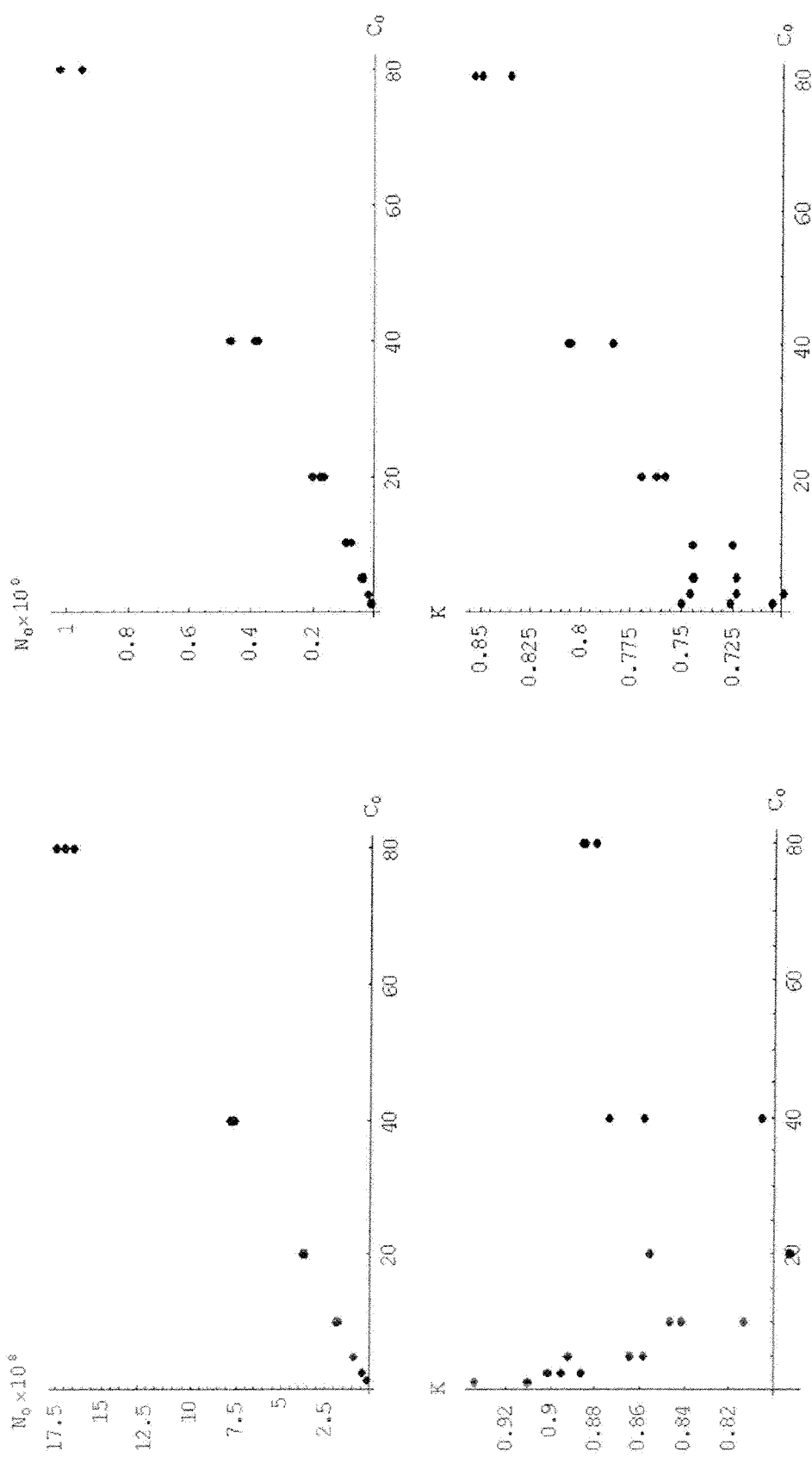

FIG. 26 illustrates standard curves on a linear scale generated by PCR amplification of serial diluted samples of two different genes that were analyzed using a model based upon Michaelis-Menten kinetics.

Figure 27:
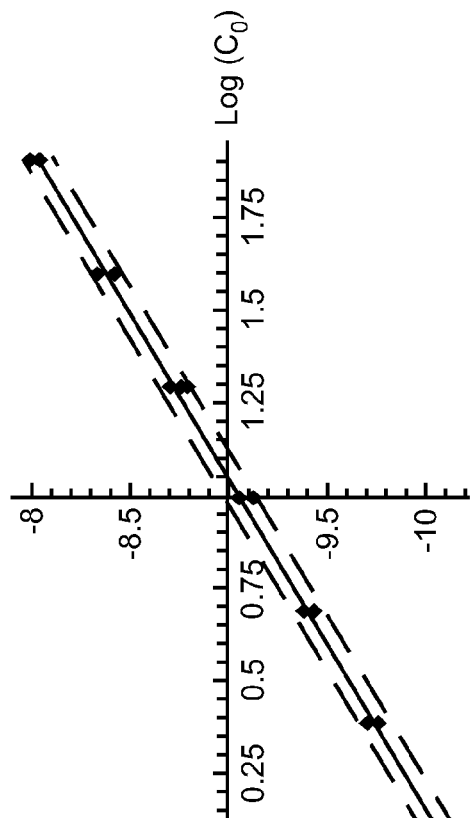
Figure 27:
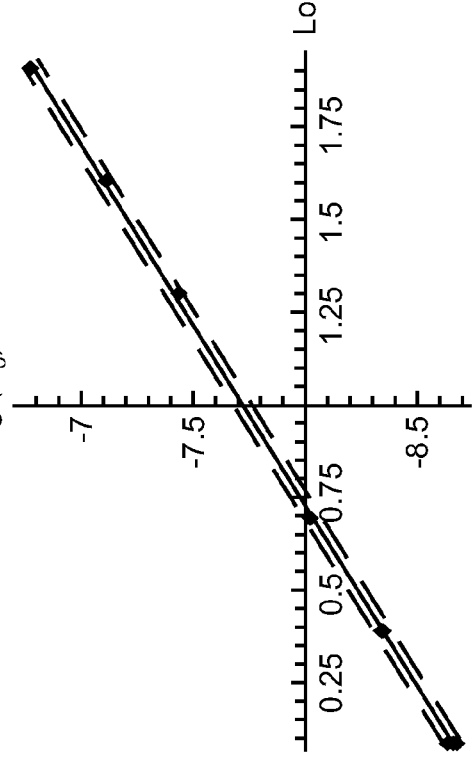

FIG. 27 illustrates standard curves on a post-logarithmic scale generated by PCR amplification of serial diluted samples of two different genes that were analyzed using a model based upon Michaelis-Menten kinetics.

Figure 28:
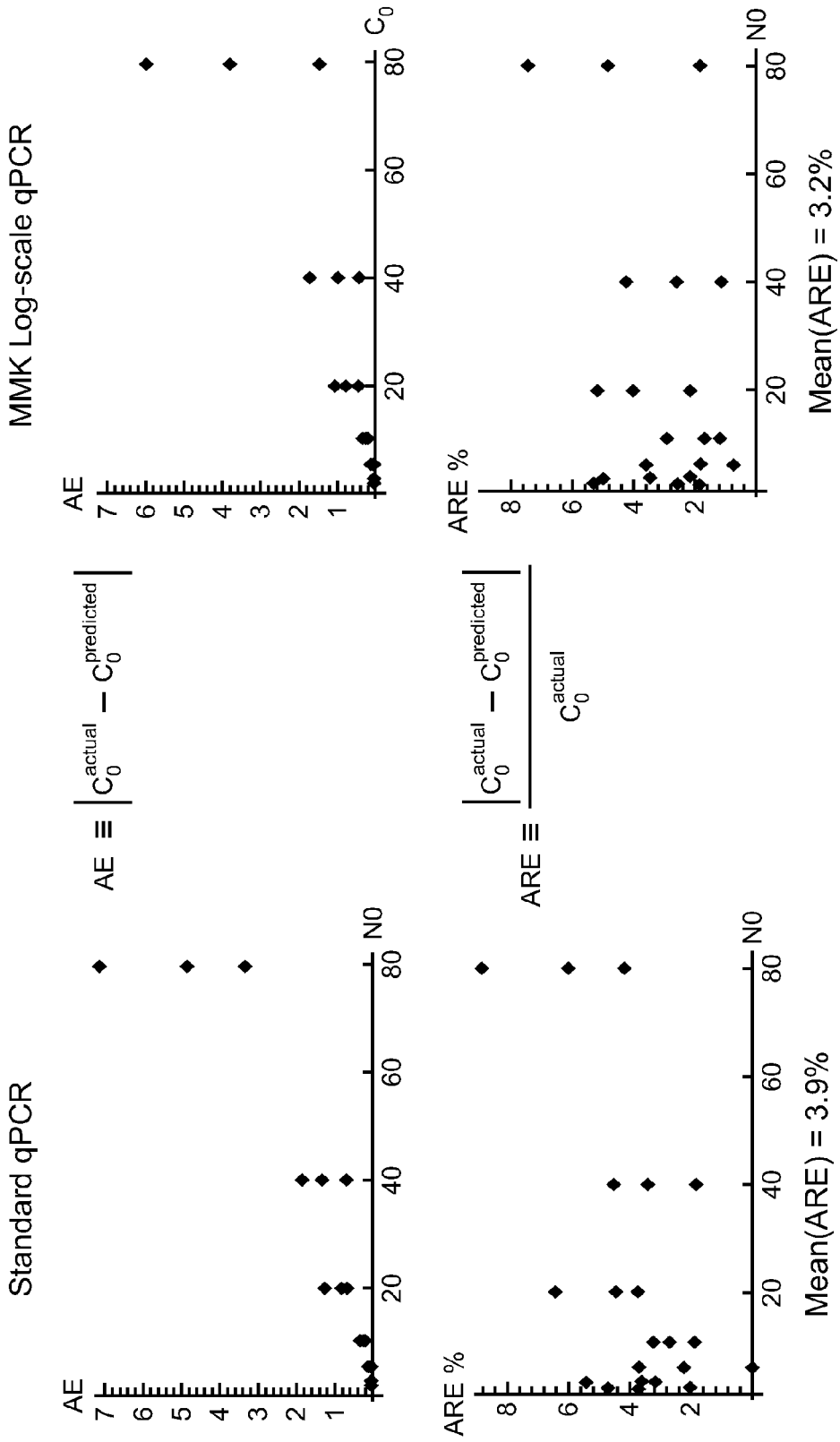

FIG. 28 compares the errors, both the absolute error and absolute relative error, for a conventional quantitative PCR approach and a model based upon Michaelis-Menten kinetics (MMK approach) for serial dilution of samples of PBEF1 in triplicate.

Figure 29:
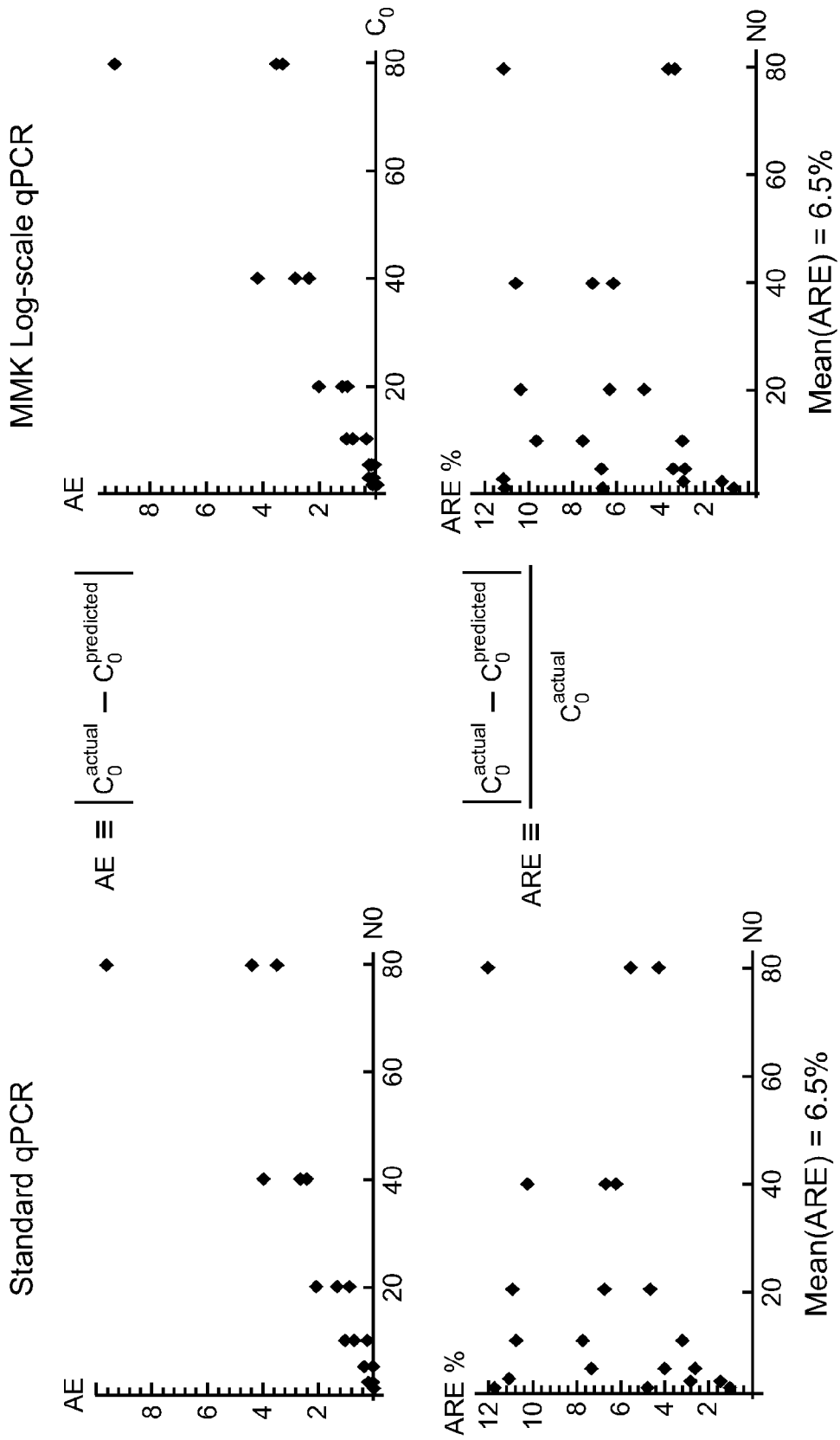

FIG. 29 compares the errors, both the absolute error and absolute relative error, for a conventional quantitative PCR approach and the MMK approach for serial dilution of samples of IFNAR1 in triplicate.

Figure 30:
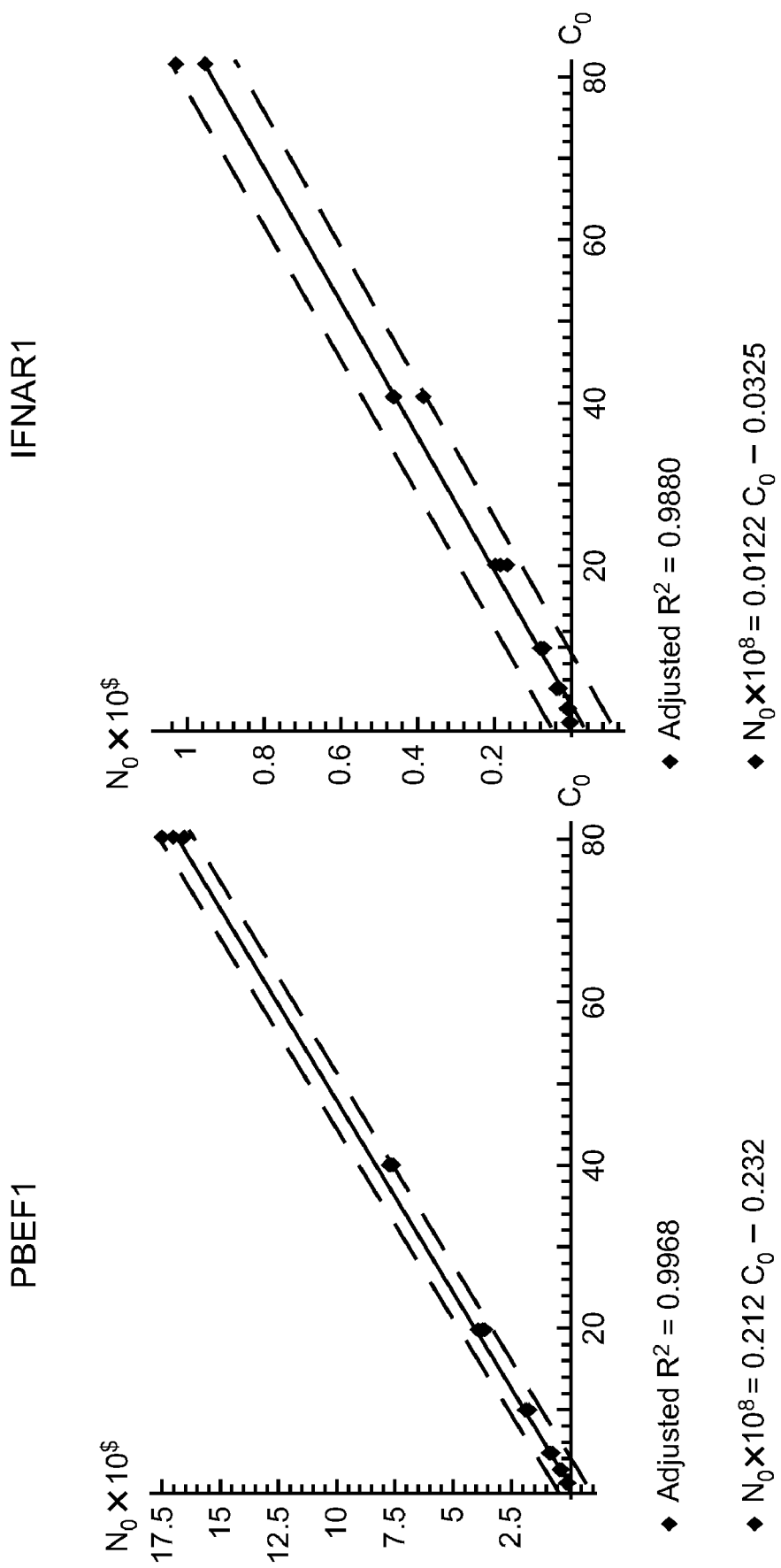

FIG. 30 illustrates how the MMK approach can be used to construct the standard curve on the linear scale and then refined by including a quadratic term.

Figure 31:
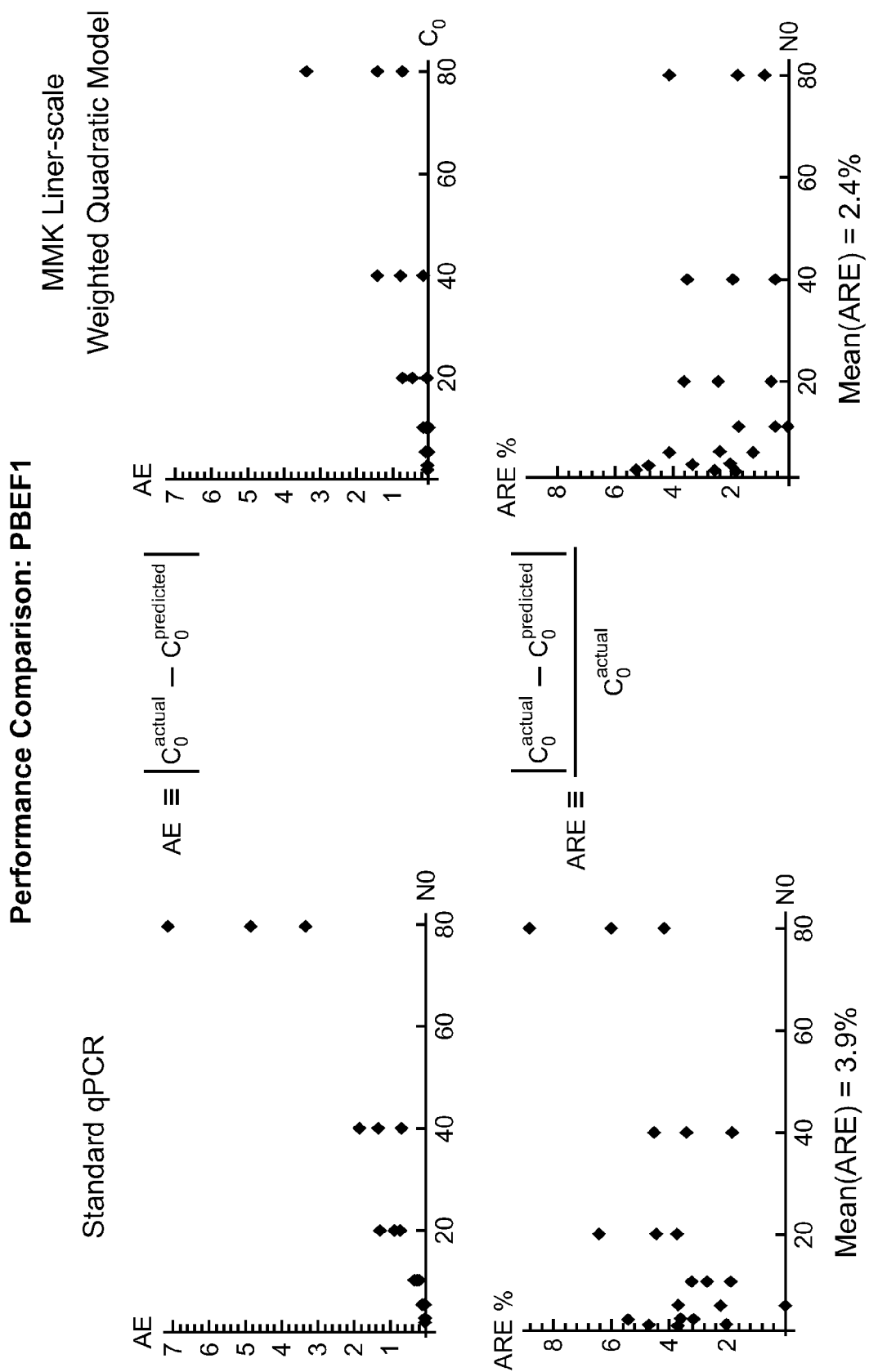

FIG. 31 illustrates how the mean ARE for a MMK linear scale model that incorporates a quadratic term is less (2.4%) than the mean ARE produced by standard qPCR (3.9%) for the PBEF1 data set.

Figure 32:
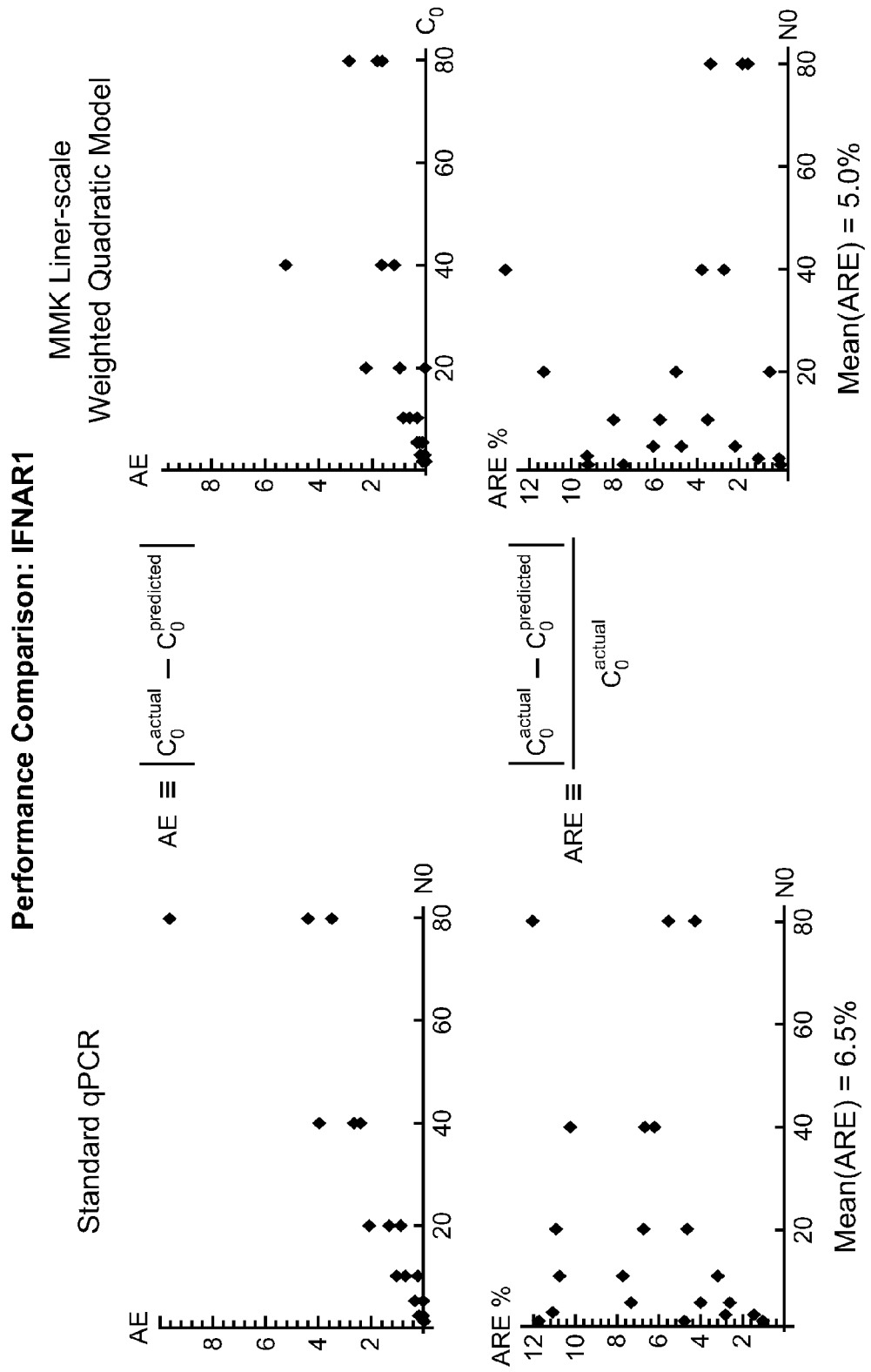

FIG. 32 illustrates how the mean ARE for a MMK linear scale model that incorporates a weighted quadratic term is less (5%) than the mean ARE produced by standard qPCR (6.5%) for the IFNAR1 data set.

Figure 33:
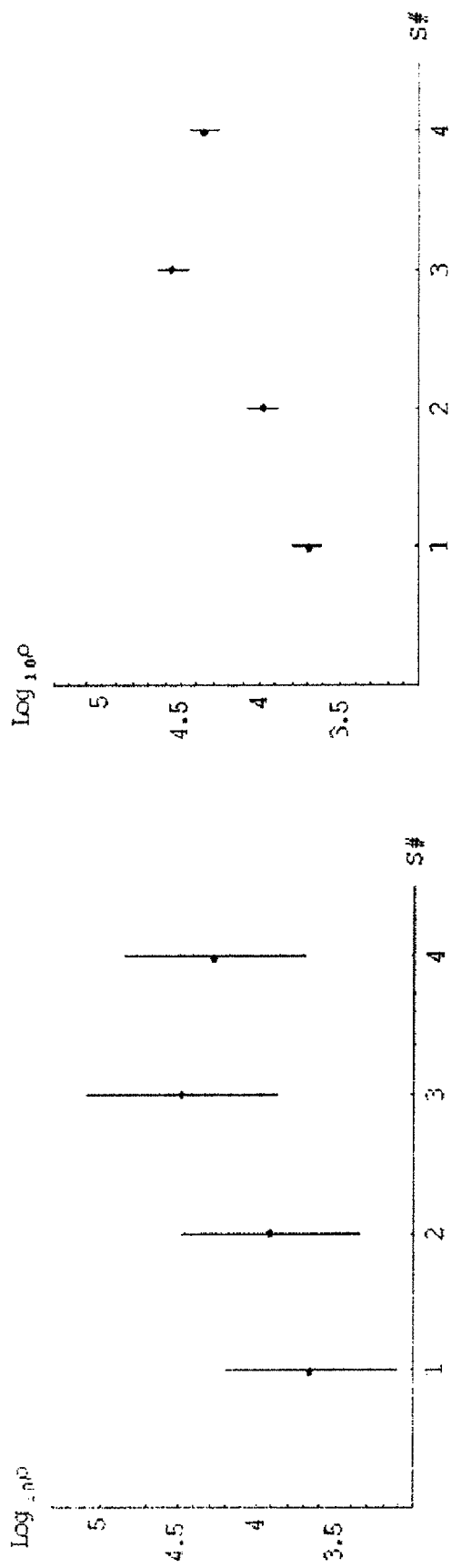

FIG. 33 illustrates how the computation of the coefficient of variance CV for $\log_{10}\rho$ using standard qPCR with the assumption that there is about a 5-10% variation in efficiency from sample to sample produces $\log_{10}\rho$ with larger coefficients of variance as compared to the MMK qPCR approach using the PBEF1 data set.

Figure 34:
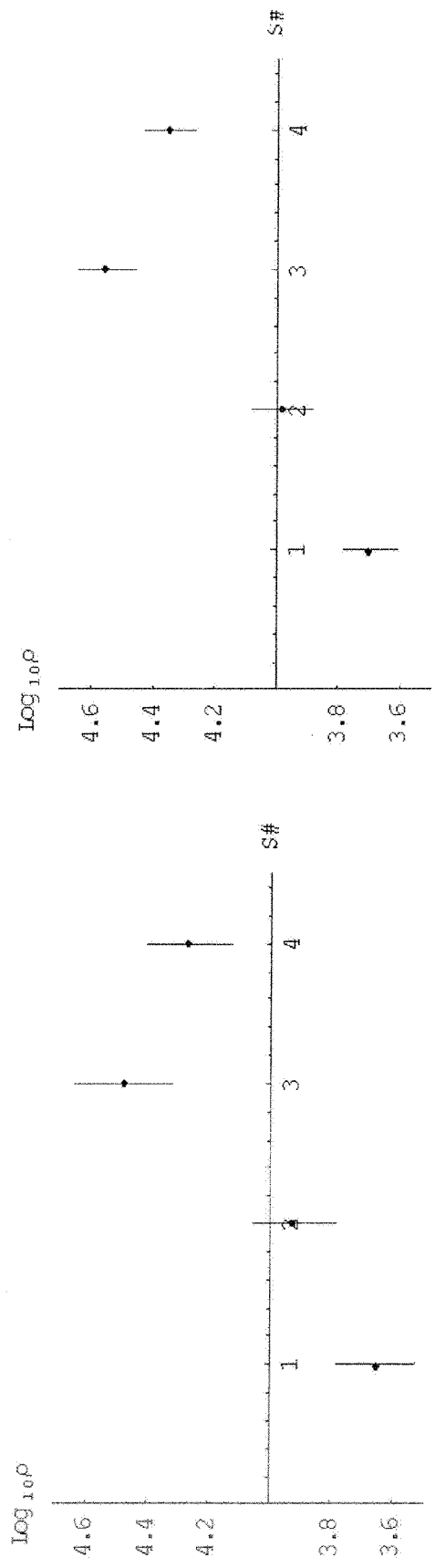

FIG. 34 illustrates how the computation of the coefficient of variance CV for $\log_{10}\rho$ using standard qPCR with the assumption that there is no variation in efficiency from sample to sample produces $\log_{10}\rho$ with larger coefficients of variance as compared to the MMK qPCR approach using the PBEF1 data set.

Figure 35:
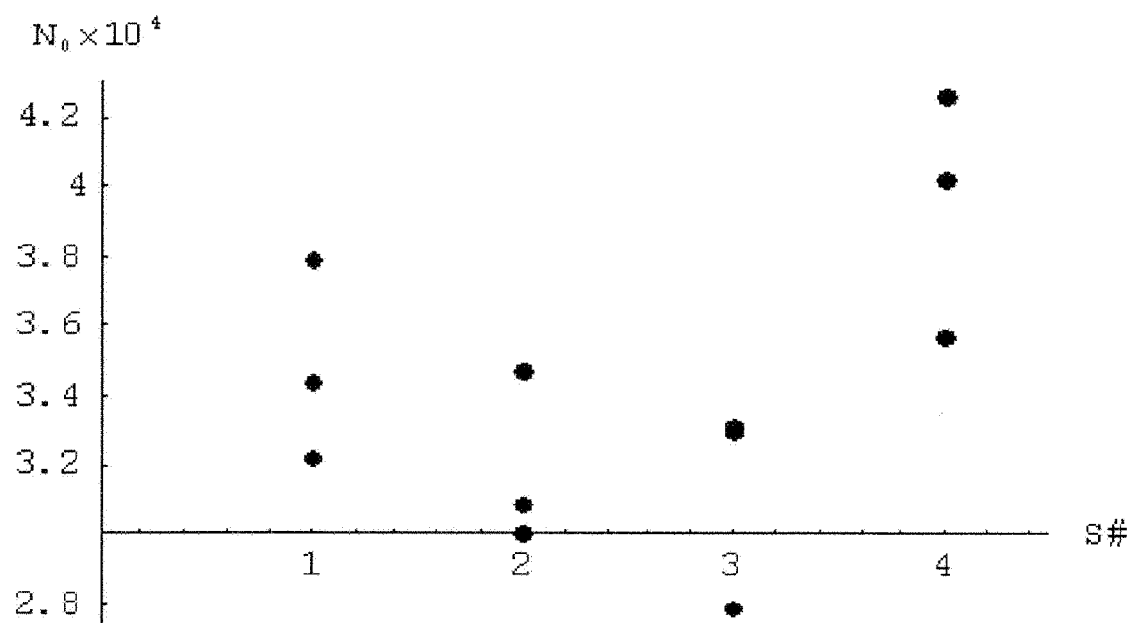
Figure 35:
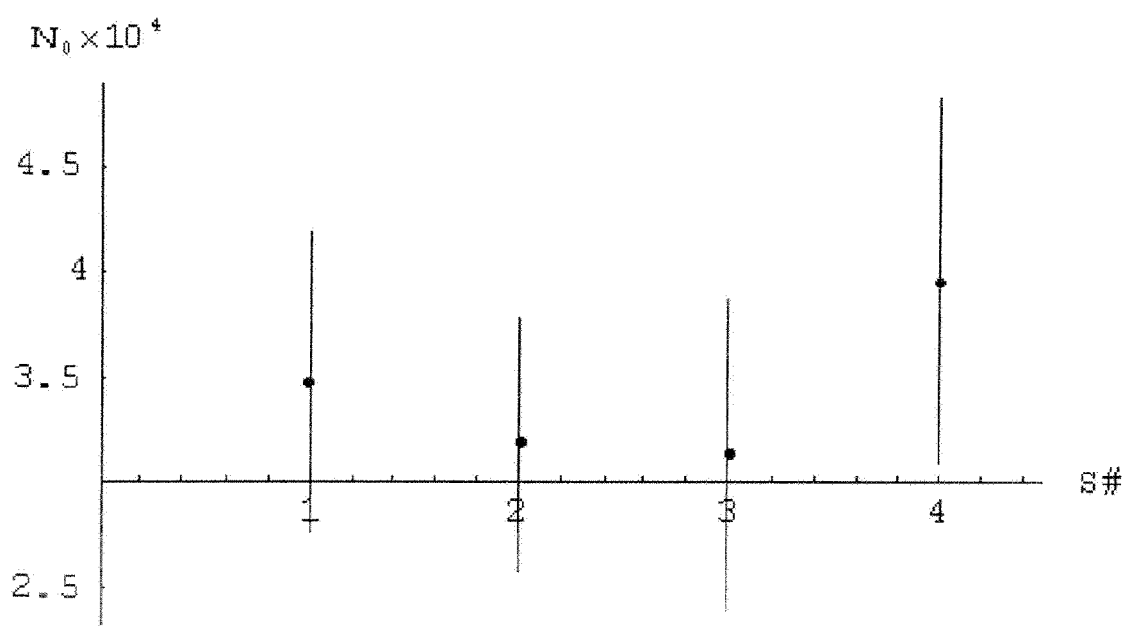

FIG. 35 illustrates $N_0$ values of the reference gene 18S for four different samples with three replicates for each sample computed using an MMK model (upper graph) and the mean $N_0$ values of 18S and their 95% confidence intervals based on the three replicates (lower graph).

Figure 36:
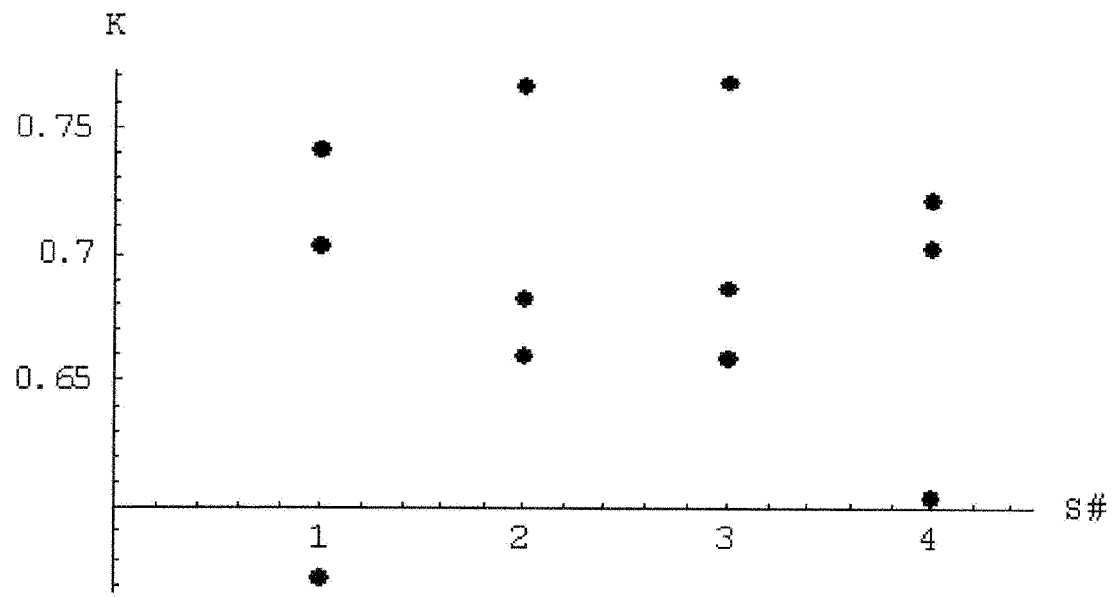
Figure 36:
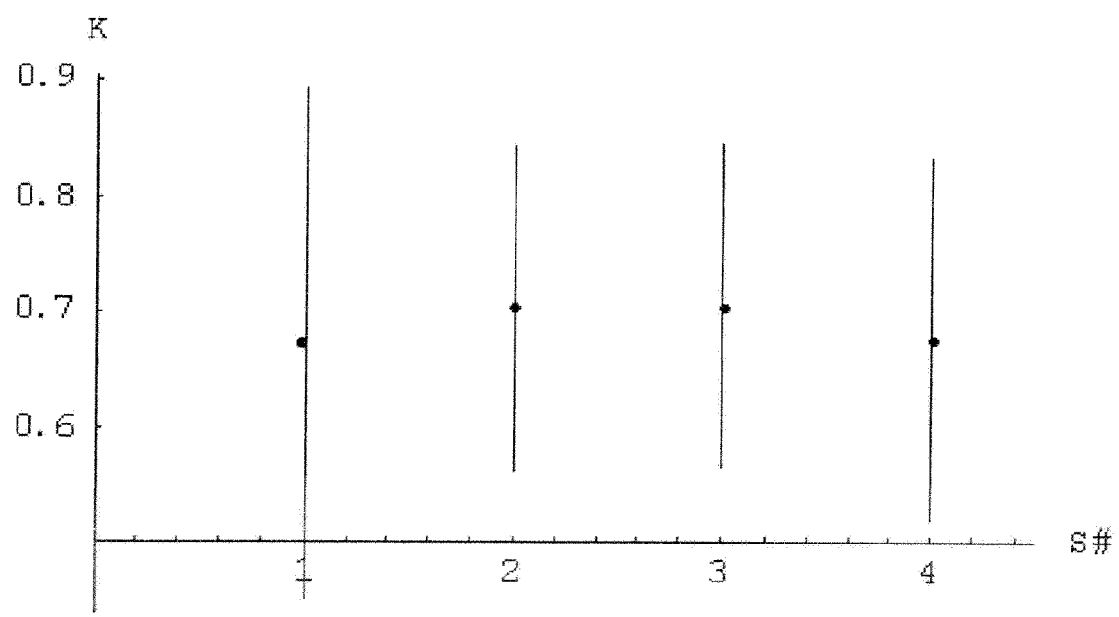

FIG. 36 illustrates the Michaelis-Menten constant K values for each of the three replicates of each of the four different samples run in the 18S dataset of FIG. 35 (upper graph) and the confidence intervals in the value $N_0$ computed for each of the four samples in the 18S dataset (lower graph).

Figure 37:
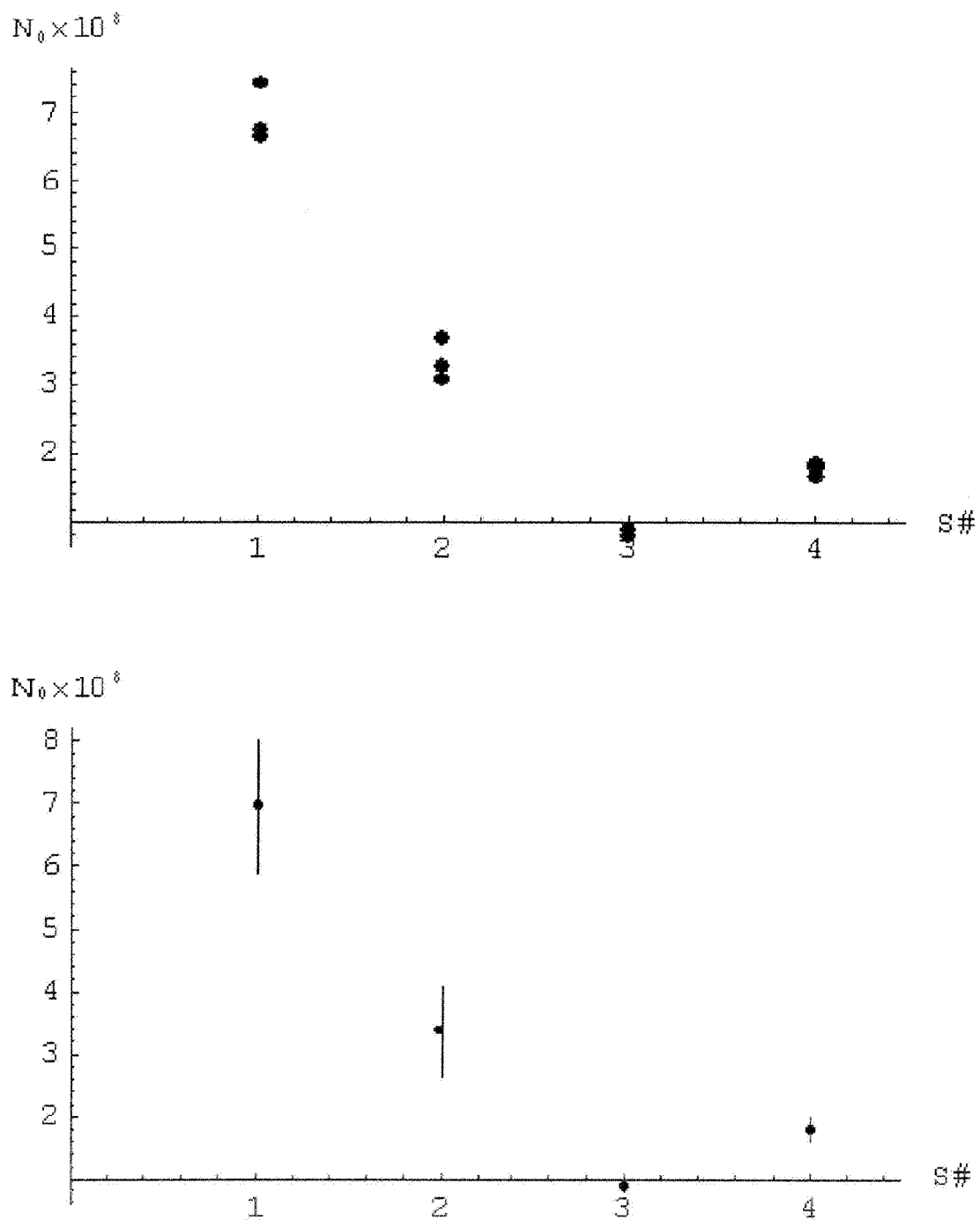

FIG. 37 illustrates $N_0$ values of the gene PBEF1 for four different samples with three replicates for each sample computed using an MMK model (upper graph) and the mean $N_0$ values of 18S and their 95% confidence intervals based on the three replicates (lower graph).

Figure 38:
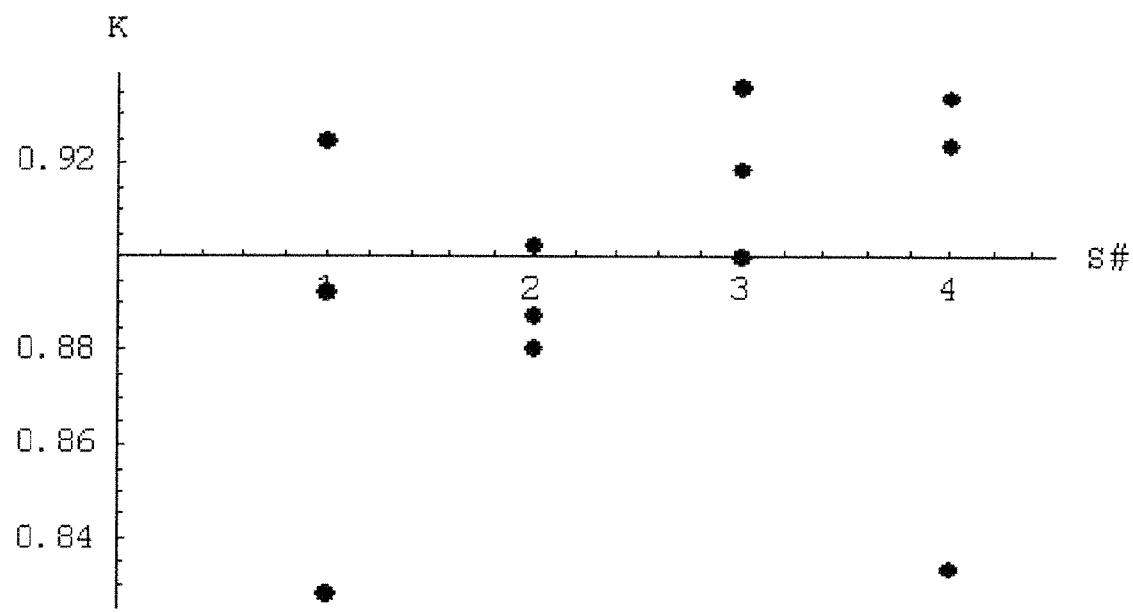
Figure 38:
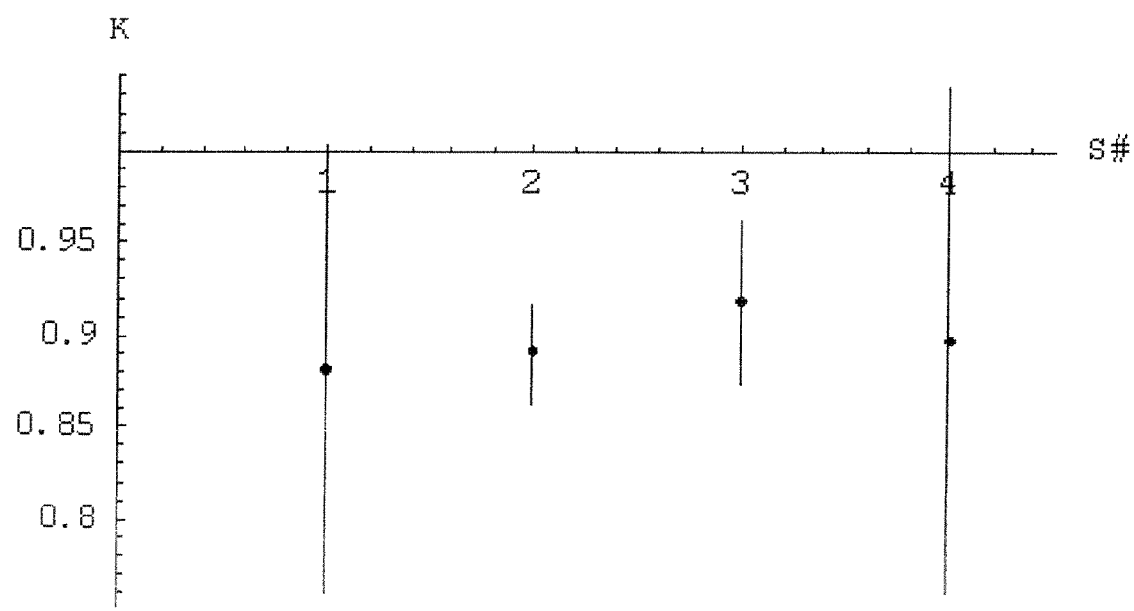

FIG. 38 illustrates the Michaelis-Menten constant K values for each of the three replicates of each of the four different samples run in the PBEF1 dataset of FIG. 37 (upper graph) and the confidence intervals in the value $N_0$ computed for each of the four samples in this PBEF1 dataset (lower graph).

Figure 39:
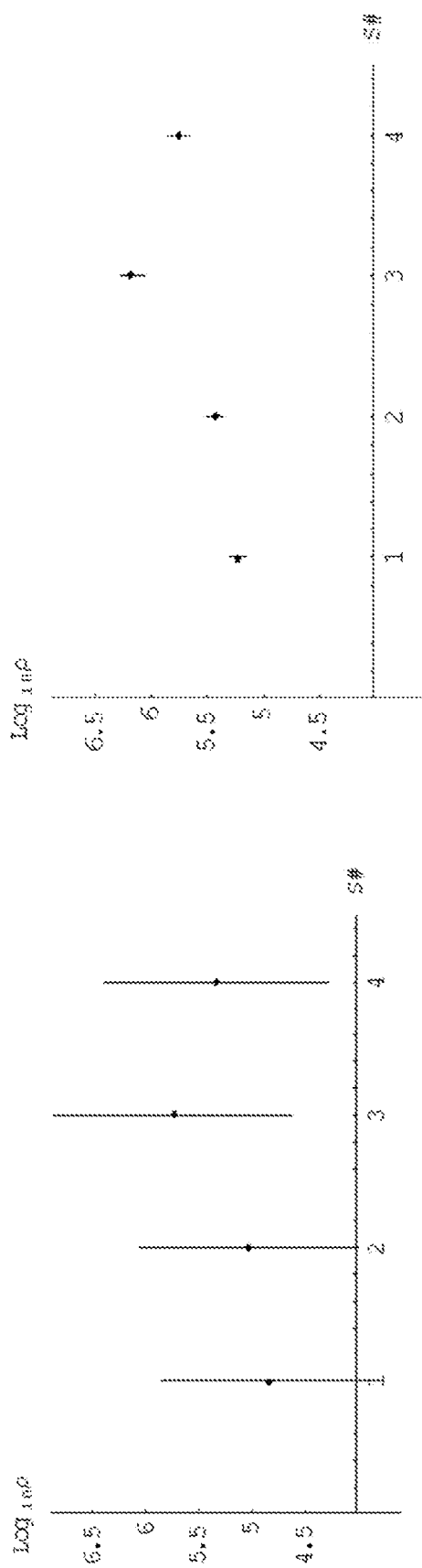

FIG. 39 illustrates the computation of the coefficient of variance CV for $\log_{10}\rho$ using standard qPCR with the assumption that there is about a 5-10% variation of the efficiency from sample to sample, to the MMK qPCR approach using an ADM data set (comprising four different samples, with each sample containing three replicates).

Figure 40:
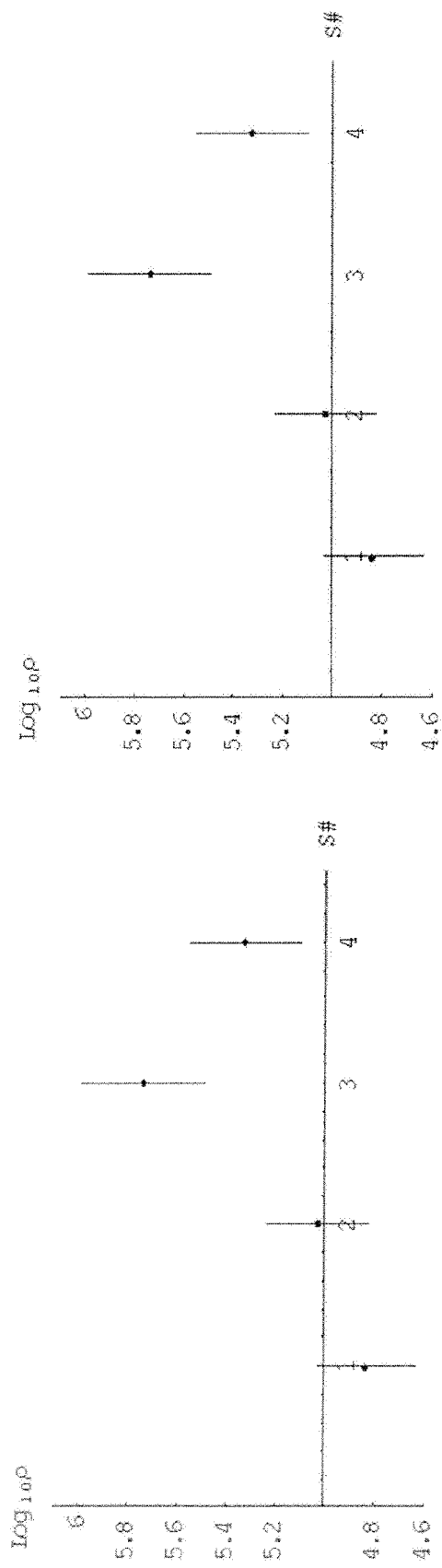

FIG. 40 illustrates the computation of the coefficient of variance CV for $\log_{10}\rho$ using standard qPCR, with the assumption that there is no variation of the efficiency from sample to sample, to the MMK qPCR approach using the ADM data set of FIG. 39.

Figure 41:
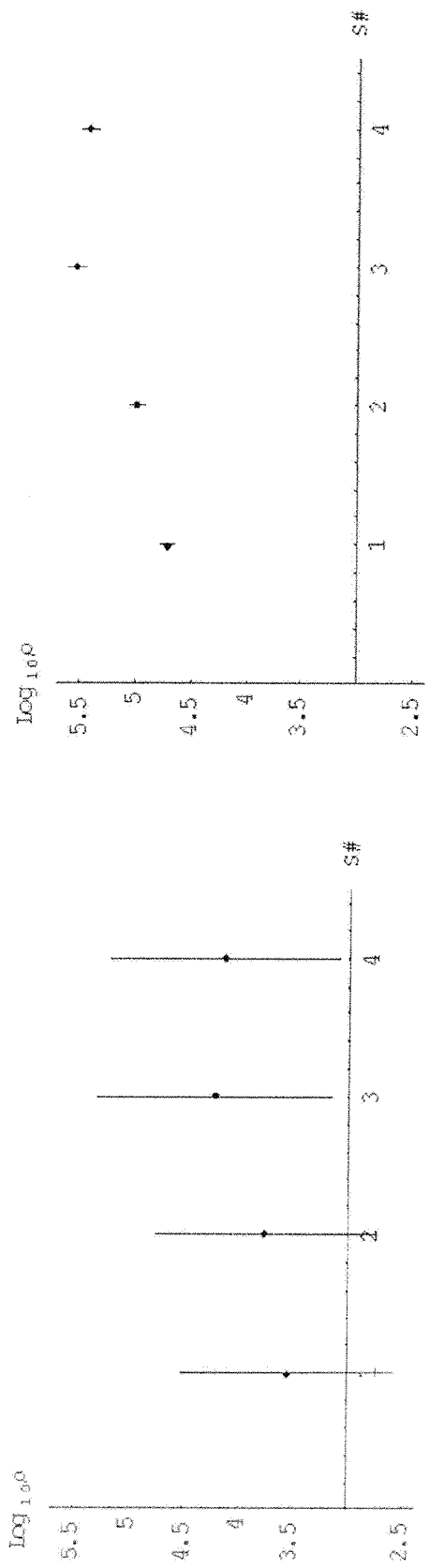

FIG. 41 illustrates the computation of the coefficient of variance CV for $\log_{10}\rho$ using standard qPCR with the assumption that there is about a 5-10% variation of the efficiency from sample to sample, to the MMK qPCR approach using an IL1R2 data set (comprising four different samples, with each sample containing three replicates).

Figure 42:
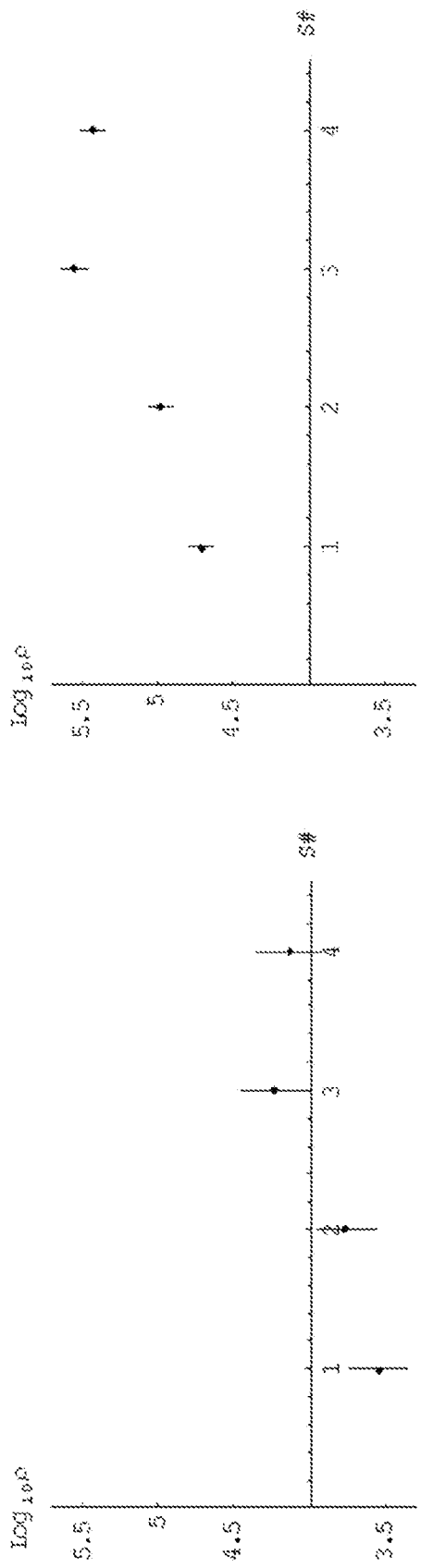

FIG. 42 illustrates the computation of the coefficient of variance CV for $\log_{10}\rho$ using standard qPCR, with the assumption that there is no variation of the efficiency from sample to sample, to the MMK qPCR approach using the IL1R2 data set of FIG. 41.

Figure 43:
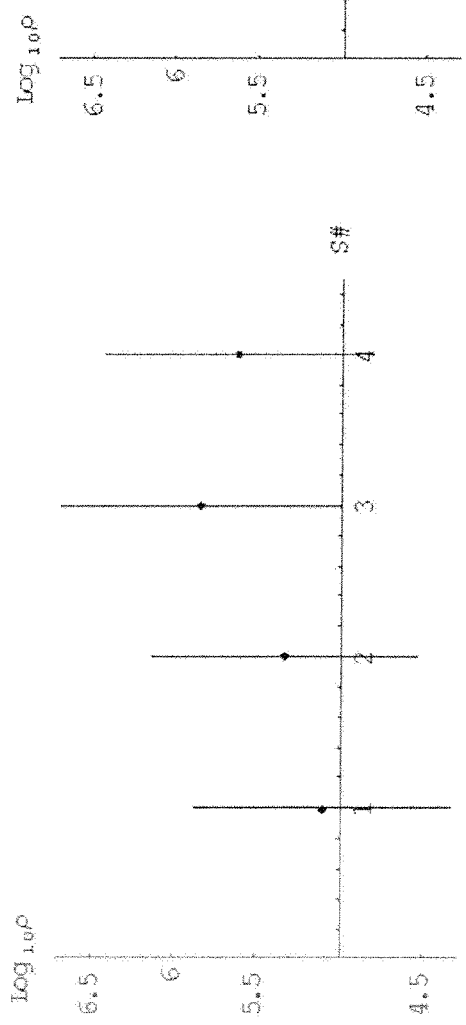

FIG. 43 illustrates the computation of the coefficient of variance CV for $\log_{10}\rho$ using standard qPCR with the assumption that there is about a 5-10% variation of the efficiency from sample to sample, to the MMK qPCR approach using an IRAK3 data set (comprising four different samples, with each sample containing three replicates).

Figure 44:
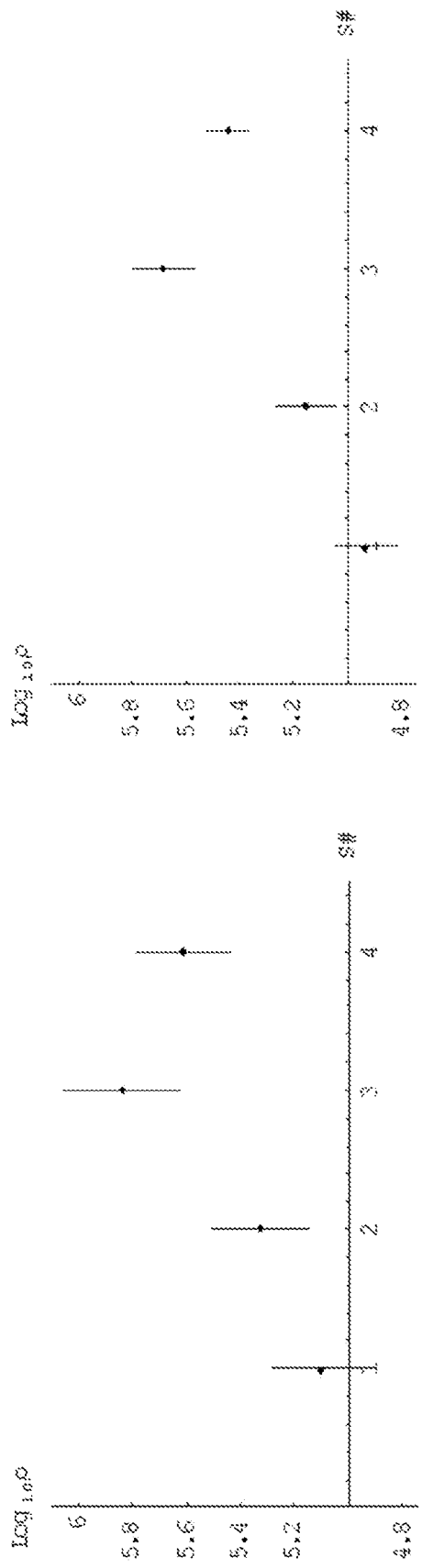

FIG. 44 illustrates the computation of the coefficient of variance CV for $\log_{10}\rho$ using standard qPCR, with the assumption that there is no variation of the efficiency from sample to sample, to the MMK qPCR approach using the IRAK3 data set of FIG. 43.

Figure 45:
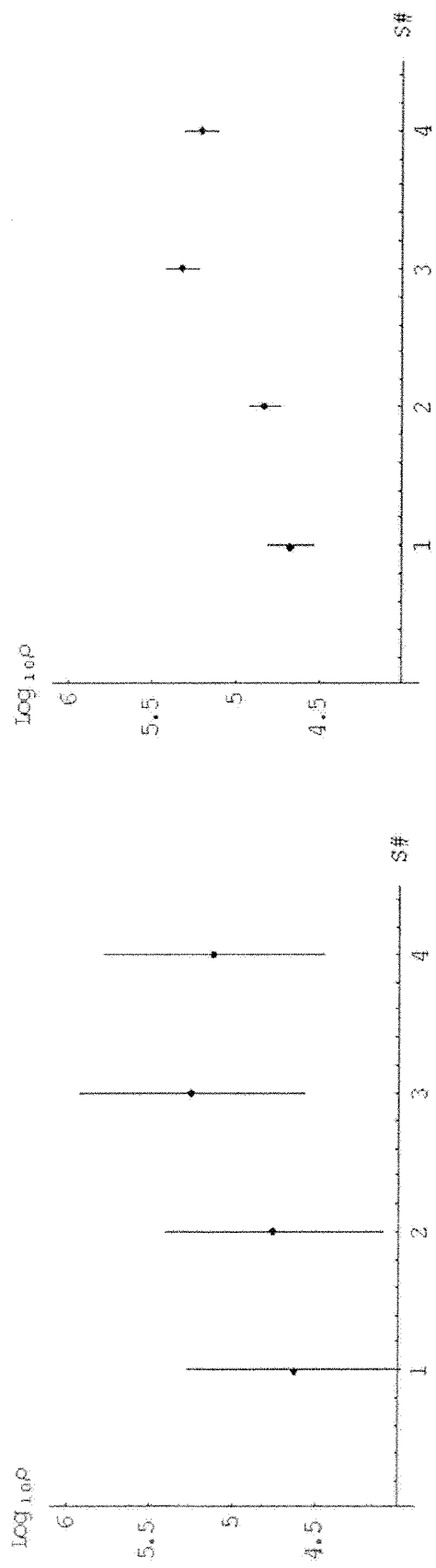

FIG. 45 illustrates the computation of the coefficient of variance CV for $\log_{10}\rho$ using standard qPCR with the assumption that there is about a 5-10% variation of the efficiency from sample to sample, to the MMK qPCR approach using a JAK3 data set (comprising four different samples, with each sample containing three replicates).

Figure 46:
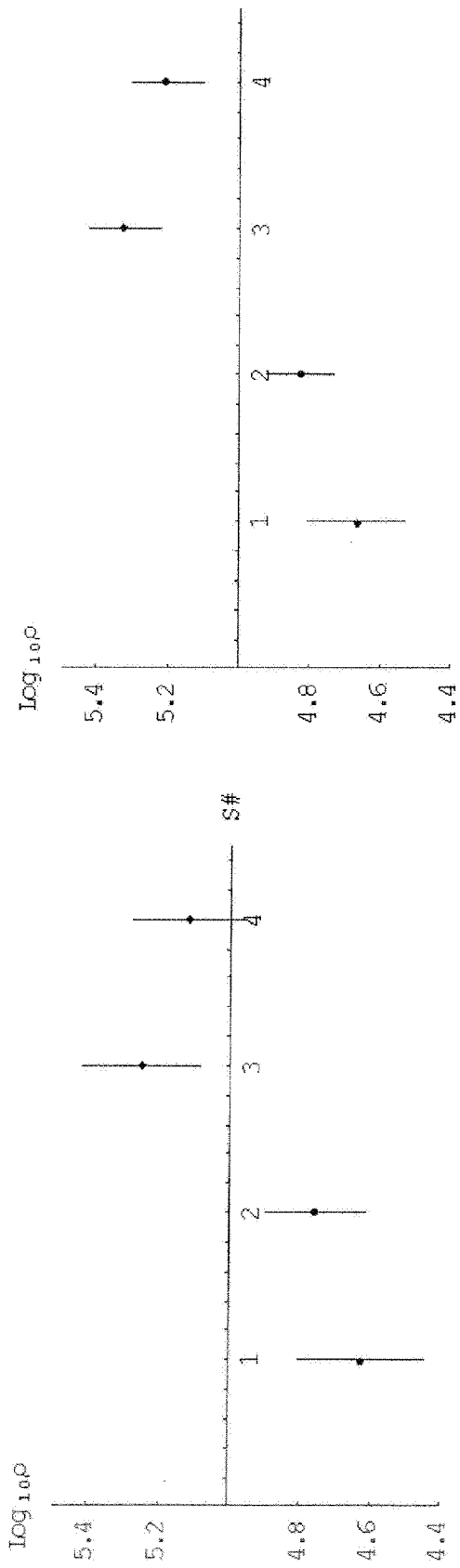

FIG. 46 illustrates the computation of the coefficient of variance CV for $\log_{10}\rho$ using standard qPCR, with the assumption that there is no variation of the efficiency from sample to sample, to the MMK qPCR approach using the JAK3 data set of FIG. 45.

Figure 47:
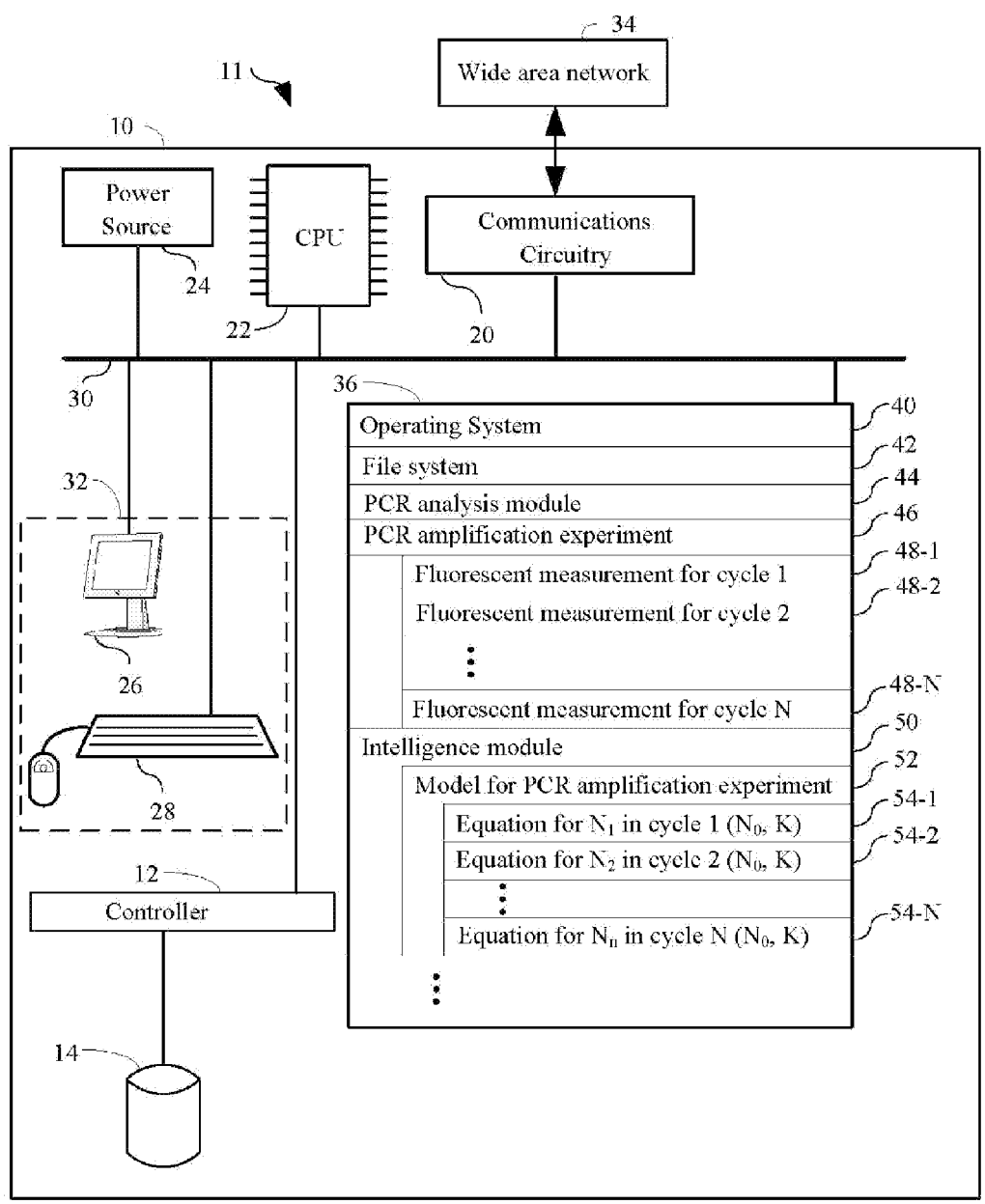

FIG. 47 illustrates a computer system for calculating an initial amount of a target nucleic acid $N_0$ in a sample in accordance with an embodiment of the present invention.

Like reference numerals refer to corresponding parts throughout the several views of the drawings.

5 DETAILED DESCRIPTION OF THE INVENTION

The present invention provides systems and methods for extracting quantitative information about the initial amount of a nucleic acid in a sample from individual PCR amplification curves taken of the sample. The approach is based on the fact that the PCR reaction is governed by Michaelis-Menten kinetics (MMK).

5.1 Definitions

The terms "receive" and "receiving," as used herein, mean "to come into possession of," or "coming into possession of," respectively. This can be done, for example, by retrieving data from a local or remote computer system, a network, or the Internet. This can also be done, for example, by direct measurement.

The term "sample" as used herein refers to any biological sample from an organ, tissue, or biological fluid, e.g., liver tissue sample, pancreatic tissue sample, soft tissue, muscle tissue, bone tissue, bladder tissue, lung tissue, epithelial tissue, endothelial tissue, blood sample, urine, mucosal swab, etc., obtained from any subject may serve as a biological specimen. Typically, the biological sample comprises mRNA for at least a first gene and quantitative information about the mRNA in the sample is desired. Quantitative information for a gene can be, for example, a concentration of the mRNA for the gene in the sample, an abundance of the mRNA for the gene in the sample relative to the abundance of the mRNA of another gene in the sample, and/or a number of molecules of the mRNA for the gene in the sample.

The term "sepsis" as used herein refers to a systemic host response to infection with SIRS plus a documented infection (e.g., a subsequent laboratory confirmation of a clinically significant infection such as a positive culture for an organism). Thus, sepsis refers to the systemic inflammatory response to a documented infection (see, e.g. American College of Chest Physicians Society of Critical Care Medicine, Chest, 1997, 101:1644-1655, the entire contents of which are herein incorporated by reference). As used herein, "sepsis" includes all stages of sepsis including, but not limited to, the onset of sepsis, severe sepsis, septic shock and multiple organ dysfunction ("MOD") associated with the end stages of sepsis.

As used herein, a "subject" is an animal, preferably a mammal, more preferably a non-human primate, and most preferably a human. The terms "subject", "individual" and "patient" are used interchangeably herein.

5.2 The MMK Model

In the present invention, approaches for providing quantitative information about the concentration and/or abundance of a target nucleic acid in a test sample are provided using a model that is referred to herein as the MMK model. The MMK model is based upon the fact that the PCR reaction is an enzymatic reaction and is therefore governed by Michaelis-Menten kinetics. Because the PCR reaction is based upon the same kinetics that governs a typical enzymatic reaction, each step of the PCR reaction is governed by the equation $$Z + S \underset{k_{-1}}{\overset{k_1}{\rightleftarrows}} Z \cdot S \overset{k_{cat}}{\rightarrow} Z + P \tag{18}$$

where Z is the enzyme and S is the substrate. Thus, assuming pseudo-steady-state for Z·S, the concentration of Z·S is determined by Michaelis-Menten kinetics as $$[Z \cdot S] = [Z][S]/K_M \tag{19}$$

where $K_M = (k_{cat} + k_{-1})/k_1$ is the Michaelis-Menten constant. Therefore, the rate of product formation is given by:

$$v = \frac{v_{max}[S]}{[S] + K_M}, \tag{20}$$

$$v_{max} = k_{cat}[Z_t]$$

where $[Z_t]$ is the total enzyme concentration. Equation 20 is provides the rate of product formation for a reaction governed by Michaelis-Menten kinetics. Although the actual elongation process in PCR is a complex, multi-step enzymatic reaction, it is reasonable to describe each PCR cycle as an effective enzymatic reaction governed by the Michaelis-Menten kinetics. Thus, the rate of product (DNA) formation $v_n$ at PCR cycle n is modeled as:

$$v_n = \frac{v_{max}[D_{n-1}]}{[D_{n-1}] + K_M}. \tag{21}$$

The concentration of the target DNA from the previous (n−1) cycle, $[D_{n-1}] \sim N_{n-1}$, plays a role of the substrate concentration at cycle n. $K_M$ is the effective Michaelis-Menten constant of the PCR process, and it is assumed to be constant throughout the process (i.e., $K_M(n) = K_M =$ constant). In equation 21, the concentration of the DNA from the previous cycle is considered to be the substrate for the next cycle.

The local PCR efficiency $E_n$ at cycle n is determined by the ratio of the free to total enzyme concentration and can be expressed in terms of the rate of product formation $v_n$ as:

$$E_n = 1 - \frac{v_n}{v_{max}} = \frac{K_M}{K_M + [D_{n-1}]} \equiv \frac{K}{K + N_{n-1}}. \tag{22}$$

With Equation 21, the efficiency in the $n^{th}$ cycle depends on how many copies of the DNA were in the previous cycle $[D_{n-1}]$.

Starting with $N_0$, the number of copies of the target nucleic acid in the sample, the number of template molecules in each cycle can be computed. Thus, the number of target nucleic acids in the sample after the first cycle ($N_1$) and the second cycle ($N_2$) is given by:

$$N_1 = N_0(1 + E_1) = N_0\left(1 + \frac{K}{K + N_0}\right) \tag{23}$$

$$N_2 = N_1(1 + E_2) =$$

Thus, the entire PCR process can be followed, starting with $N_0$, the starting number of copies of the target nucleic acid. In the first cycle, the number of copies of the target nucleic acid, $N_1$, is $N_0$ multiplied by 1 plus the efficiency in the first cycle $E_1$. But now the efficiency in the first cycle is known from Equation 22. It is K divided by K plus $N_0$, where K is the Michaelis-Menten constant. In the second cycle, the number of copies of the target nucleic acid, $N_2$, is $N_1$ multiplied by 1 plus the efficiency in the second cycle $E_2$. But, the efficiency in the second cycle is known from Equation 22. It is K divided by K plus $N_1$. Further, $N_n$ is known and can be expressed in terms of $N_0$. In this manner, $N_n$ for any given step can be computed, in the recursive manner illustrated by the Equations 23.

Equations of the form given for Equation (23) form the basis of the MMK model. A feature of the MMK model is that it comprises, for each respective fluorescent measurement in the plurality of fluorescent measurements of an PCR amplification experiment a respective equation for $N_n$, where (i) $N_n$ is the calculated amount of the target nucleic acid in cycle n of the PCR amplification experiment from which the respective fluorescent measurement was taken, and (ii) the respective equation for $N_n$ is expressed only in terms of K and $N_0$, regardless of the cycle n of the first PCR amplification experiment, where K is the Michaelis-Menten constant for the PCR amplification experiment. As discussed below, the MMK model can advantageously be used to adjust K and $N_0$ until differences between values $N_n$ computed by the MMK and corresponding fluorescent measurements in the PCR amplification experiment are minimized, thereby calculating the initial amount of a target nucleic acid $N_0$ as the minimized value for $N_0$ for the first model. In some embodiments, the initial amount of a target nucleic acid $N_0$ calculated in this manner is outputted to a user interface device, a monitor, a computer-readable storage medium, a computer-readable memory, or a local or remote computer system. In some embodiments, the initial amount of a target nucleic acid $N_0$ calculated in this manner is displayed.

Referring to FIG. 19, the local efficiency as a function of PCR cycle number is plotted, using the MMK model where the local efficiency is defined as $$E_n = \frac{K}{K + N_{n-1}} \quad (24)$$

and a certain value for K is assumed. In FIG. 19, line 1902 provides the values predicted by the MMK model whereas the data points are measured values. As can be seen in FIG. 19, for a small number of cycles and when $N_0$ is small, $N_{n-1}$ is much less than K. Thus, from Equation 24, the efficiency approaches one hundred percent. Note that in FIG. 19, there is no measurable data for cycles below cycle 20, so the computed efficiencies of these cycles is not considered. As N increases, the efficiency gradually decreases as seen in FIG. 19. As seen in FIG. 20, on the other hand, for large n, the relationship $$N_n = N_0 + \sum_{k=0}^{n-1} \frac{KN_k}{K + N_k} \sim Kn \quad (25)$$

In FIG. 20, line 2002 provides the values predicted by the MMK model whereas the data points are measured values.

Referring to FIGS. 21 and 22, where $N_n$ is computed as a function of PCR cycle number n (FIG. 21) and where $\log(N_n)$ is computed as a function of PCR cycle number (FIG. 22) using the MMK model, it is seen that the MMK model describes both the exponential and linear phases of PCR. In FIG. 21, line 2102 provides the values predicted by the MMK model whereas the data points are measured values. In FIG. 22, line 2202 provides the values predicted by the MMK model whereas the data points are measured values.

Thus, FIGS. 21 and 22 collectively show that the MMK model describes both the exponential part and the linear phase of the PCR reaction. Further, as seen in FIGS. 21 and 22, there is an excellent fit between the MMK model and the measured data up to the plateau phase (about PCR cycle 35 in FIG. 21) where certain reagents start to become depleted and the PCR reaction begins to slow down because there are insufficient primers, not enough of the enzyme, or the enzyme starts to become inefficient. The plateau phase of the PCR reaction provides no informative value on the value of $N_0$.

FIGS. 21 and 22 collectively show that the linear phase of the PCR process is a consequence of the Michaelis-Menten kinetics of the underlying enzymatic reaction and not, as it is commonly thought, a consequence of running out of PCR reagents. The Michaelis-Menten kinetics is responsible for the linear part of the PCR amplification. Reagents are running out in only the plateau phase of the PCR amplification reaction. Moreover, as mentioned above, the plateau phase has no useful information about the initial amount of target nucleic acid ($N_0$) because it depends on the amount of starting reagents, whether they run out earlier or later during the PCR cycles, and other factors that are not specific to $N_0$.

The MMK model, taken out to the third cycle of the PCR reaction is given as:

$$N_1 = N_n(1 + E_1) = N_n\left(1 + \frac{K}{E + N_0}\right) \quad (26)$$

$$N_2 = N_1(1 + E_2) =$$

$$N_1\left(1 + \frac{K}{K + N_1}\right) = N_0\left(1 + \frac{K}{K + N_0}\right)\left(1 + \frac{K}{K + N_0\left(1 + \frac{K}{K + N_0}\right)}\right)$$

$$N_1 = N_2(1 + E_1) = N_2\left(1 + \frac{K}{E + N_2}\right) =$$

$$N_0\left(1 + \frac{K}{K + N_0}\right)\left(1 + \frac{K}{K + N_0\left(1 + \frac{K}{K + N_0}\right)}\right)$$

$$\left(1 + \frac{K}{K + N_n\left(1 + \frac{K}{K + N_0}\right)\left(1 + \frac{K}{K + N_0\left(1 + \frac{K}{K + N_0}\right)}\right)}\right).$$

From (26), it is seen that the entire model only requires fitting for two parameters, $N_0$ and K. Advantageously, no assumption that the efficiency for each sample, and for each serial dilution of the sample, is the same because the value $N_0$ and K are fit to each PCR amplification curve separately. In the method, the sum of squares of the residuals, $N_n$-$FS_n$ (where $N_n$ is from the recursive model and $FS_n$ is the fluorescent signal measured at PCR cycle n) is minimized with respect to $N_0$ and K, leading to a direct estimation of $N_0$ and K of the amplification trajectory. For example, consider cycle 20 of the PCR amplification. A recursive formula that expresses $N_{20}$ in terms of just K and $N_0$ can be written in the same form as Equations 26. Then, the difference between this formula and the measured signal is minimized with respect to the two parameters, $N_0$ and K.

With the model based upon Michaelis-Menten kinetics, one issue is which cycles of the PCR reaction should be fitted in order to derive the values $N_0$ and K. Clearly cycles in which the fluorescent signal is not above background noise are not suitable for fitting. Turning to FIG. 23, in one embodiment, the first PCR cycle $n_{start}$ in a given PCR amplification experiment that is chosen for fitting is the PCR cycle that fits the following criteria: (i) the local efficiency of all subsequent cycles consistently decreases, and (ii) the efficiency of the cycle $n_{start}+1$ is less than 1.05. Referring to FIG. 23, the cycle that fits this set of criteria for the data illustrated in FIG. 23 is PCR amplification experiment cycle number 19.

Turning to FIG. 24, in one embodiment, the last PCR cycle $n_{end}$ of the given PCR amplification experiment that is chosen for fitting is determined by taking the second derivative of the observed fluorescent signal ($d^2FS/dn^2$) for each cycle greater than or equal to $n_{start}$ and choosing $n_{end}$ to be the first cycle where the second derivative is less than zero ($d^2FS/dn^2<0$).

This corresponds to the cycle at which the measures signal starts deviating from the linear dependence. The upper plot in FIG. 24 shows the measured fluorescent signal (FS) as a function of cycle number n. The lower plot in FIG. 24 shows the second derivative of the measured fluorescent signal (FS) with respect to cycle number n. At PCR cycle number 26, for the data illustrated in FIG. 24, $d^2FS/dn^2 < 0$ and thus $n_{end}$ is chosen to be PCR cycle number 26.

In some embodiments, $n_{start}$ and $n_{end}$ are chosen by the criteria set forth above in conjunction with FIGS. 23 and 24. Then, the parameters $N_0$ and K in the model based upon Michaelis-Menten kinetics are adjusted such that the sum of the squares of the residuals $N_n$-$FS_n$ for the PCR cycles in the set $\{n_{start}, \ldots, n_{end}\}$ is minimized in order to obtain values for $N_0$ and K. In some embodiments, the parameters $N_0$ and K in the model based upon Michaelis-Menten kinetics are adjusted such that the sum of the squares of the residuals $N_n$-$FS_n$ for the PCR cycles in a contiguous subset of $\{n_{start}, \ldots, n_{end}\}$ is minimized in order to obtain values for $N_0$ and K. In some embodiments, the parameters $N_0$ and K in the model based upon Michaelis-Menten kinetics are adjusted such that the sum of the squares of the residuals $N_n$-$FS_n$ for the PCR cycles in the set $\{n_{start}, \ldots, n_{end}\}$ is minimized in order to obtain values for $N_0$ and K.

In some embodiments, the parameters $N_0$ and K in the model based upon Michaelis-Menten kinetics are adjusted such that the sum of the squares of the residuals $N_n$-$FS_n$ for the PCR cycles in a set of five to twenty PCR cycles from the measureable exponential phase and linear of the PCR amplification is minimized in order to obtain values for $N_0$ and K. In some embodiments, the parameters $N_0$ and K in the model based upon Michaelis-Menten kinetics are adjusted such that the sum of the squares of the residuals $N_n$-$FS_n$ for the PCR cycles in a set of about seven to twelve PCR cycles from the measurable exponential phase and linear phase of the PCR amplification is minimized in order to obtain values for $N_0$ and K. In some embodiments, the set of PCR cycles that are regressed against the model based upon Michaelis-Menten kinetics is not contiguous (e.g., one or more cycles in the amplification series between $n_{start}$ and $n_{end}$ is not present).

Thus, with the above inventive methods, numerical minimization of the sum of squares of the residuals, $N_n$-$FS_n$, leads to a direct estimation of $N_0$ and K of the PCR amplification experiment. Thus, applying the methods, where $n_{start}$ and $n_{end}$ are identified using the methods respectively used in FIGS. 23 and 24, to the PCR amplification experiment illustrated in FIG. 25 yields $N_0 = 1.57 \times 10^{-7}$ and $K = 0.858$.

To test the accuracy of the model based on Michaelis-Menten kinetics, serial dilutions of a known initial nucleic acid template concentration $[C_0 = 80, 40, 20, \ldots 1.25 \text{ ng/}\mu\text{L}]$ were performed in triplicate and subjected to PCR amplification. It will be appreciated that such dilutions could have been in duplicate or some larger number of replicates and the inclusion of data from any number of replicates in the inventive MMK model is within the scope of the present invention. The resulting PCR amplification reactions were fitted with the model based upon Michaelis-Menten kinetics. The results of these experiments are shown in FIG. 26. FIG. 26 illustrates that there is the expected linear relationship between serial dilutions of the initial sample $[C_0]$ and $N_0$ for both PBEF1 and IFNAR1 data on a linear scale. Moreover, the value of K is limited to the range of about 0.8 to 0.93 for PBEF1 and 0.70 to 0.85 for IFNAR1.

Turning to FIG. 27, in the present invention, using the inventive model based upon Michaelis-Menten kinetics, the standard curve can be constructed on post-log scale, just as in the conventional qPCR analysis. As illustrates in FIG. 27 the adjusted $R^2$ is 0.9993 for PBEF1 and 0.9971 for IFNAR1. This data demonstrates the validity of the inventive model based upon Michaelis-Menten kinetics.

FIG. 28 compares the errors, the absolute error and absolute relative error, for the standard quantitative PCR approach given in the background section and the inventive model based upon Michaelis-Menten kinetics (MMK approach) presented above for serial dilution of samples of PBEF1 in triplicate. As illustrated in FIG. 28, for PBEF1, in the standard quantitative PCR approach, the mean(ARE) across all the serial dilutions is 3.9 percent. In contrast, in the MMK approach, the mean(ARE) across all the serial dilutions is 3.2 percent. Thus, the MMK approach produces a smaller error.

FIG. 29 compares the errors, the absolute error and absolute relative error, for the standard quantitative PCR approach given in the background section and the inventive model based upon Michaelis-Menten kinetics (MMK approach) presented above for serial dilution of samples of IFNAR1 in triplicate. As illustrated in FIG. 29, for IFNAR1, in the standard quantitative PCR approach the mean(ARE) across all the serial dilutions is 6.5 percent. Further, the MMK approach produces the same 6.5 percent value.

In conventional quantitative PCR standard curves can be constructed only on the log scale. However, referring to FIG. 30, since the MMK model provides direct estimation of the initial template DNA concentration, within the MMK approach, it is possible to construct the standard curve in the linear scale and refine it by including a quadratic term or by performing a weighted regression, for example, to minimize mean ARE. The linear scale is advantageous because it can address the case in which $N_0$ approaches zero. In contrast, when actual $N_0$ approaches zero, calculated $N_0$ approaches infinity on the log scale.

Thus, FIGS. 26 through 29, illustrate an aspect of the present invention in which a plurality of fluorescent measurements for each PCR amplification experiment in a plurality of PCR amplification experiments is obtained (received, measured). Then, each MMK model in a plurality of MMK models is refined. Each MMK model in the plurality of MMK models is for a PCR amplification experiment in the plurality of PCR amplification experiments. For each respective model in the plurality of models, the respective model comprises a respective equation for $N_n$ for the corresponding fluorescent measurement n in the PCR amplification experiment corresponding to the respective model where (i) each $N_n$ in the respective model is the amount of target nucleic acid in cycle n of the PCR amplification experiment corresponding to the respective model from which the respective fluorescent measurement was taken and (ii) each respective equation for $N_n$ in the respective model is expressed only in terms of K and $N_0$, regardless of the cycle n of the corresponding fluorescent measurement in the corresponding PCR amplification experiment that is corresponding to the respective equation for $N_n$. Here, K is the Michaelis-Menton constant for the corresponding PCR amplification experiment. Refinement of each respective model in the plurality of models comprises adjusting K and $N_0$ for each equation for $N_n$ in the respective model until differences between values $N_n$ computed by the respective model and corresponding fluorescent measurements in the plurality of fluorescent measurements of the PCR amplification experiment corresponding to the respective model are minimized, thereby calculating the initial amount of a target nucleic acid $N_0$ as the minimized value for $N_0$ for each respective model.

In some embodiments, each PCR amplification experiment in the plurality of PCR amplification experiments represents a serial dilution of the sample, and the method further comprises plotting $\log_{10}(N_0)$ of the initial amount of a target nucleic acid $N_0$ calculated for each model in the plurality of models as a function of relative concentration of the sample used in the PCR amplification experiment for each model in the plurality of models.

In some embodiments, each PCR amplification experiment in the plurality of PCR amplification experiments represents a serial dilution of the sample, and the method further comprises plotting the initial amount of a target nucleic acid $N_0$ calculated for each model in the plurality of models as a function of relative concentration of the sample used in the PCR amplification experiment for each model in the plurality of models.

In some embodiments, each PCR amplification experiment in the plurality of PCR amplification experiments represents a serial dilution of the sample and the method further comprises refining the value $N_0$ calculated for each model in the plurality of models as a function of relative concentration of the sample so that a single refined value for $N_0$ is computed for the plurality of models. In some embodiments, this refining step comprises performing a weighted regression to minimize a mean absolute relative error (ARE) of a plurality of ARE values with respect to the value $N_0$ calculated by each model in the plurality of models, where each $$ARE = \frac{|C_0^{actual} - C_0^{predicted}|}{C_0^{actual}}$$

value in the plurality of ARE values is for a respective model in the plurality of models, and where $C_0^{actual}$ is the actual relative concentration of the sample used for the PCR amplification experiment corresponding to the respective model and $C_0^{predicted}$ is the calculated relative concentration of the sample used for the PCR amplification experiment corresponding to the respective model that is determined by the calculated value $N_0$ for the respective model.

In some embodiments, each PCR amplification experiment in the plurality of PCR amplification experiments represents a serial dilution of the sample, where the serial dilution is done in duplicate or triplicate (or some larger number of replicates) and a different model is computed for each duplicate of each serial dilution or each triplicate (or some larger number of replicates) of each serial dilution.

Thus, the present invention provides an MMK model that can be performed on either the log scale or the linear scale. As illustrated above in conjunction with FIGS. 28 and 29, the performance of the MMK model relative to conventional logarithmic-based quantitative PCR is comparable. However, advantageously, in the present invention, the MMK model can be performed on the linear scale and then refined to produce a better model using, for example, weighted regression. FIG. 31 illustrates how the mean ARE for a MMK linear scale model that incorporates a quadratic term is much less (2.4%) than the mean ARE produced by standard qPCR (3.9%) for the PBEF1 data set. FIG. 32 illustrates how the mean ARE for a MMK linear scale model that incorporates a weighted quadratic term is much less (5.0%) than the mean ARE produced by standard qPCR (6.5%) for the IFNAR1 data set.

Referring to Equation 27, since the relative detection sensitivity and reverse transcriptase-related parameters are not known, the metric $\rho$ is still necessary in order to determine actual mRNA levels in a sample $$\rho = \psi \frac{N_A}{N_B} = \frac{N_{AM}}{N_{BM}} \tag{27}$$

where $N_{AM}$ and $N_{BM}$ are the values calculated by the MMK model for the initial number of molecules of genes A and B. Advantageously, $\rho$ does not depend on any additional parameters. For instance, there is no need to know the efficiencies, or even the Michaelis-Menten constant value K, or to take into account their variability. The initial concentrations $N_{AM}$ and $N_{BM}$ are calculated for individual PCR amplification experiments separately and they do not depend on individual reaction rates and no additional efficiency studies are required.

Given Equation 27 and the inventive MMK model disclosed herein another aspect of the present invention comprises receiving (measuring, obtaining) a first plurality of fluorescent measurements for a first PCR amplification experiment and a second plurality of fluorescent measurement for a second PCR amplification experiment, where the first and second PCR amplification experiment use a given sample that includes mRNA for a first gene and mRNA for the second gene.

For each respective fluorescent measurement in the first plurality of fluorescent measurements, the first model comprises a respective equation for $N_n$, where (i) $N_n$ is the calculated amount of the mRNA for the first gene in cycle n of the first PCR amplification experiment from which the respective fluorescent measurement was taken, and (ii) the respective equation for $N_n$ is expressed only in terms of K and $N_{AM}$, regardless of the cycle n of the first PCR amplification experiment, where K is the Michaelis-Menton constant for the first PCR amplification experiment and $N_{AM}$ is the amount of mRNA for the first gene in the sample prior to the first PCR amplification experiment.

For each respective fluorescent measurement in the second plurality of fluorescent measurements, the second model comprises a respective equation for $N_n$, where (i) $N_n$ is the calculated amount of mRNA for the second gene in cycle n of the second PCR amplification experiment from which the respective fluorescent measurement was taken, (ii) the respective equation for $N_n$ in the second model is expressed only in terms of $K_2$ and $N_{BM}$, regardless of the cycle n, where $K_2$ is the Michaelis-Menton constant for the second PCR amplification experiment and $N_{BM}$ is the mount of mRNA for the second gene in the sample prior to second PCR amplification experiment.

In some embodiments, the first PCR experiment is performed using a first aliquot of the sample and the second PCR experiment is performed using a second aliquot of the sample.

Refinement of the first model comprises adjusting K and $N_{AM}$ until differences between values $N_n$ computed by the first model and corresponding fluorescent measurements in the first plurality of fluorescent measurements are minimized, thereby calculating the initial amount of mRNA for the first gene in the sample prior to amplification in the first PCR amplification experiment ($N_{AM}$) as the minimized value for $N_{AM}$ for the first model. Refinement of the second model comprises adjusting $K_2$ and $N_{BM}$ until a difference between values $N_n$ computed by said second model and corresponding fluorescent measurements in the second plurality of fluorescent measurements are minimized. The method further comprises computing $$\rho = \frac{N_{AM}}{N_{BM}}. \tag{28}$$

In some embodiments, the first gene is a gene associated with a phenotypic characterization and the second gene is a gene is not associated with the phenotypic characterization. For example, in some embodiments, the first gene is known to be up-regulated in subjects that have a particular phenotypic characterization. In some embodiments, the first gene is known to be down-regulated in subjects that have a particular phenotypic characterization. In contrast, the second gene is not up-regulated or down-regulated in subject that have a particular phenotypic characterization relative to subjects that do not have the phenotypic characterization.

In some embodiments, when ρ is above a threshold value, the member of a species (e.g., human, cow, dog, sheep, any mammal, any plant, etc.) that contributed the sample is deemed to have the phenotypic characterization. The threshold value is application specific but may be derived without undue experimentation using conventional techniques. In some embodiments, when ρ is above a threshold value, the member of a species that contributed the sample is deemed to not have the phenotypic characterization. In some embodiments, when ρ is below a threshold value, the member of a species that contributed the sample is deemed to have the phenotypic characterization. In some embodiments, when ρ is below a threshold value, the member of a species that contributed the sample is deemed to not have the phenotypic characterization.

In some embodiments, the phenotypic characterization is a cell type, a cell morphology, a disease state, an abnormal state in a tissue or organ, an abnormal cell type, or an abnormal cell morphology. In some embodiments, the phenotypic characterization is an indication that the test subject from which the sample was taken is likely to develop sepsis. In some embodiments, the initial amount of a target nucleic acid $N_{AM}$ in the sample is a concentration of the mRNA of the first gene in the sample. In some embodiments the initial amount of a target nucleic acid $N_{AM}$ in the sample is a number of mRNA molecules transcribed from the first gene in the sample. In some embodiments, the initial amount of a target nucleic acid $N_{BM}$ in the sample is a concentration of the mRNA of the first gene in the sample. In some embodiments the initial amount of a target nucleic acid $N_{BM}$ in the sample is a number of mRNA molecules transcribed from the first gene in the sample.

Referring to FIG. 33, computation of the coefficient of variance (CV) for $\log_{10}\rho$ using conventional quantitative PCR with the assumption that there is about a 5-10% variation of the efficiency from sample to sample, to the innovative MMK qPCR approach using the PBEF1 data set, it is seen that the coefficient of variance for $\log_{10}\rho$ for the standard qPCR approach ranges from 6.90% to 7.63% whereas the coefficient of variance for the MMK qPCR approach is 0.99% to 1.28%. One reason that the inventive MMK approach provides improved (smaller) coefficient of variance values is that the MMK approach does not have to assume efficiency is constant in each of the PCR amplification experiments because $N_0$ is computed on curve-by-curve basis. However, referring to FIG. 34, even if the assumption is made that there is no variation in efficiency E, the standard qPCR approach still has larger coefficient of variance values for $\log_{10}\rho$.

5.3 Kits

Some embodiments of the invention may also comprise a kit to perform any of the methods described herein. In a non-limiting example, primers, enzymes for reverse transcription, enzymes for amplification and additional agents, and software for performing any combination of the methods disclosed herein may be comprised in a kit. The kits will thus comprise one or more of these reagents in suitable container means. The kits may also comprise agents for RNA isolation, purification of amplification products, labels, etc.

The components of the kits, other than the software, may be packaged either in aqueous media or in lyophilized form. The suitable container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the reagent containers in close confinement for commercial sale. Such containers may include injection or blow-molded plastic containers into which the desired vials are retained.

5.4 Computer Systems

FIG. 47 details an exemplary system 11 for use in calculating an initial amount of a target nucleic acid $N_0$ in a sample in accordance with the methods of the present invention. The system preferably comprises a computer system 10 having:

a central processing unit 22;

a main non-volatile storage unit 14, for example a hard disk drive, for storing software and data, the storage unit 14 controlled by storage controller 12;

a system memory 36, preferably high speed random-access memory (RAM), for storing system control programs, data, and application programs, comprising programs and data loaded from non-volatile storage unit 14; system memory 36 may also include read-only memory (ROM);

a user interface 32, comprising one or more input devices (e.g., keyboard 28, a mouse) and a display 26 or other output device;

a network interface card 20 (communications circuitry) for connecting to any wired or wireless communication network 34 (e.g., a wide area network such as the Internet);

a power source 24 to power the aforementioned elements; and an internal bus 30 for interconnecting the aforementioned elements of the system.

Operation of computer 10 is controlled primarily by operating system 40, which is executed by central processing unit 22. Operating system 40 can be stored in system memory 36. In a typical implementation, system memory 36 also includes:

a file system 42 for controlling access to the various files and data structures used by the present invention;

a PCR analysis module 44 that generates a plurality of fluorescent measurements 48 in a PCR amplification experiment 46, wherein each respective fluorescent measurement $FS_n$ 48 in the plurality of fluorescent measurements is a fluorescent measurement taken in a different cycle n in the PCR amplification experiment 46 of a sample; and an intelligence module 50 adapted to process the plurality of fluorescent measurements 48 by refining a model for the PCR amplification experiment 52, wherein, for each respective fluorescent measurement 48 in the plurality of fluorescent measurements, the model 52 comprises a respective equation for $N_n$ 54.

Here, (i) $N_n$ is the calculated amount of the target nucleic acid in cycle n of the PCR amplification experiment 46 from which the respective fluorescent measurement 48 was taken, and (ii) the respective equation 54 for $N_n$ is expressed only in terms of K and $N_0$, regardless of the cycle n of the PCR amplification experiment 46, wherein K is the Michaelis-Menten constant for the PCR amplification experiment and $N_0$ is an initial amount of a target nucleic acid in the sample. Refinement of the model by intelligence module 50 comprises adjusting K and $N_0$ until differences between values $N_n$ computed by the model and corresponding fluorescent measurements in the plurality of fluorescent measurements are minimized, thereby determining an initial amount of a target nucleic acid $N_0$ in the sample. As illustrated in FIG. 47, computer 10 comprises PCR amplification experiment 46. PCR amplification experiment 46 can be in any form of data storage including, but not limited to, a flat file, a relational database (SQL), or an on-line analytical processing (OLAP) database (MDX and/or variants thereof). In some embodiments, the software, modules and data illustrated in FIG. 47 (e.g. modules 44 and 50) are on a single computer (e.g., computer 10) and in other embodiments they are hosted (stored) by as many as computers (not shown). In fact, any arrangement of the modules illustrated in FIG. 47 on one or more computers is within the scope of the present invention so long as these one or more computers are addressable with respect to each other across network 34 or by other electronic means. Thus, the present invention fully encompasses a broad array of computer systems.

The present invention can be implemented as a computer program product that comprises a computer program mechanism embedded in a computer-readable storage medium. Further, any of the methods of the present invention can be implemented in one or more computers. Further still, any of the methods of the present invention can be implemented in one or more computer program products. Some embodiments of the present invention provide a computer program product that encodes any or all of the methods disclosed herein. Such methods can be stored on a CD-ROM, DVD, magnetic disk storage product, or any other computer-readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer program product that contains any or all of the program modules shown in FIG. 47. These program modules can be stored on a CD-ROM, DVD, magnetic disk storage product, or any other computer-readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

6 EXAMPLES

Example 1

Referring to FIG. 35, what is illustrated in the upper graph are the $N_0$ values of the reference gene 18S for four different samples with three replicates for each sample computed using the innovative MMK model. What is illustrated in the lower graph are the mean $N_0$ values of 18S and their 95% confidence intervals based on the three replicates. FIG. 35 illustrates how the $N_0$ of 18S does not vary much from sample to sample when calculated using the innovative MMK model. Further, the coefficient of variation of $N_0$ is 7.5%-9.5% (note the linear scale of $N_0$). Referring to FIG. 36, in the upper graph, the Michaelis-Menten constant K values for the 18S dataset illustrated in FIG. 35 are given for each of the three replicates of each of the four different samples run. In the lower graph in FIG. 36, the confidence intervals for each of the four samples is given. The data shows that the means of K are almost the same for each sample. However, K varies significantly from replicate to replicate, the coefficient of variation of (K) being ~8%-13.5%. There is no reason to expect that the reactions have the same rate in each well, but, the average K for 18S should be about the same in each of the four samples. As is seen in the lower graph in FIG. 36, there is very little variation in the average K for the samples.

Example 2

Referring to FIG. 37, what is illustrated in the upper graph are the $N_0$ values of the expressed gene PBEF1 for four different samples with three replicates for each sample computed using the innovative MMK model. What is illustrated in the lower graph are the mean $N_0$ values of PBEF1 and their 95% confidence intervals based on the three replicates. FIG. 37 illustrates how the scale of $N_0$ of PBEF1 is 4-5 orders of magnitude smaller than for 18S. Further, the mean $N_0$ values for PBEF1 (and typically also for other expressed genes) are well separated for different samples, meaning that the MMK model is capable of discerning differences in the value of N0 for different samples. In the lower graph of FIG. 37, confidence intervals are based on the three replicates and the coefficient of variation of N0 ($CV(N_0)$ is ~4%-9% on the linear scale. Referring to FIG. 38, in the upper graph, the Michaelis-Menten constant K values for the PBEF1 dataset illustrated in FIG. 37 are given for each of the three replicates of each of the four different samples run. In the lower graph in FIG. 38, the means of K in each of the four samples and their confidence intervals are given. The data shows that the means of K are almost the same for each sample. However, K varies significantly from replicate to replicate, the coefficient of variation of (K) being ~1%-6%. There is no reason to expect that the reactions have the same rate in each well, but, the average K for each sample should be about the same. As is seen in the lower graph in FIG. 38, there is very little variation in the average K for the samples.

Example 3

Referring to FIG. 39, computation of the coefficient of variance CV for $\log_{10}\rho$ using standard qPCR with the assumption that there is about a 5-10% variation of the efficiency from sample to sample, to the innovative MMK qPCR approach using a data set for gene (comprising four different samples, with each sample containing three replicates), it is seen that the coefficient of variance for $\log_{10}\rho$ for the standard qPCR approach ranges from 10.14% to 10.58% whereas the coefficient of variance for the MMK qPCR approach is 0.7% to 0.9%. Referring to FIG. 40, even if the assumption is made that there is no variation in efficiency E, the standard qPCR approach still has larger coefficient of variance values for $\log_{10}\rho$.

Example 4

Referring to FIG. 41, the computation of the coefficient of variance CV for $\log_{10}\rho$ using standard qPCR with the assumption that there is about a 5-10% variation of the efficiency from sample to sample is compared to the computation of the same values based upon the innovative MMK qPCR approach using a data set for gene IL1R2 (comprising four different samples, with each sample containing three replicates). It is seen that the coefficient of variance for $\log_{10}\rho$ for the standard qPCR approach ranges from 12.87% to 13.87% whereas the coefficient of variance for the MMK qPCR approach is 0.77% to 0.84%. Referring to FIG. 42, even if the assumption is made that there is no variation in efficiency E, the standard qPCR approach still has larger coefficient of variance values for $\log_{10}\rho$.

Example 5

Referring to FIG. 43, the computation of the coefficient of variance CV for $\log_{10}\rho$ using standard qPCR with the assumption that there is about a 5-10% variation of the efficiency from sample to sample is compared to the computation of the same values based upon the innovative MMK qPCR approach using a data set for gene IRAK3 (comprising four different samples, with each sample containing three replicates). It is seen that the coefficient of variance for $\log_{10}\rho$ for the standard qPCR approach ranges from 7.32% to 7.73% whereas the coefficient of variance for the MMK qPCR approach is 0.72% to 1.23%. Referring to FIG. 42, even if the assumption is made that there is no variation in efficiency E, the standard qPCR approach still has larger coefficient of variance values for $\log_{10}\rho$.

Example 6

Referring to FIG. 45, the computation of the coefficient of variance CV for $\log_{10}\rho$ using standard qPCR with the assumption that there is about a 5-10% variation of the efficiency from sample to sample is compared to the computation of the same values based upon the innovative MMK qPCR approach using a data set for gene JAK3 (comprising four different samples, with each sample containing three replicates). It is seen that the coefficient of variance for $\log_{10}\rho$ for the standard qPCR approach ranges from 6.57% to 7.05% whereas the coefficient of variance for the MMK qPCR approach is 0.96% to 1.5%. Referring to FIG. 46, even if the assumption is made that there is no variation in efficiency E, the standard qPCR approach still has larger coefficient of variance values for $\log_{10}\rho$.

7 REFERENCES CITED

All references cited herein are incorporated herein by reference in their entirety and for all purposes to the same extent as if each individual publication or patent or patent application was specifically and individually indicated to be incorporated by reference in its entirety herein for all purposes.

8 MODIFICATIONS

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. A method of calculating an initial amount of a target nucleic acid $N_0$ in a sample, the method comprising:
(A) receiving a first plurality of fluorescent measurements, wherein each respective fluorescent measurement $FS_n$ in the first plurality of fluorescent measurements is a fluorescent measurement taken in a different cycle n in a first PCR amplification experiment of the sample;
(B) computing a first model that calculates the initial amount of the target nucleic acid $N_0$ in the first PCR amplification experiment, wherein, for each respective fluorescent measurement in the first plurality of fluorescent measurements, the first model comprises a respective equation for $N_n$, wherein
   (i) $N_n$ is the calculated amount of the target nucleic acid in cycle n of the first PCR amplification experiment from which the respective fluorescent measurement was taken, and
   (ii) the respective equation for $N_n$ is expressed only in terms of K and $N_0$, regardless of the cycle n of the first PCR amplification experiment, wherein K is the Michaelis-Menten constant for the first PCR amplification experiment, wherein the first model comprises an equation for $N_1$, the calculated amount of the target nucleic acid in cycle 1 of the first PCR amplification experiment, wherein $$N_1 = N_0\left(1 + \frac{K}{K + N_0}\right); \text{ and}$$

(C) calculating the initial amount of the target nucleic acid $N_0$ in the first PCR amplification experiment, using the first model.

2. The method of claim 1, the method further comprising:
(D) outputting the calculated initial amount of a target nucleic acid $N_0$ calculated in said calculating step (C) in user readable form to a user interface device, a monitor, a computer-readable storage medium, a computer-readable memory, or a local or remote computer system; or displaying the calculated initial amount of a target nucleic acid $N_0$ calculated in said calculating step (C).

3. The method of claim 1, wherein the first model further comprises an equation for $N_2$, the calculated amount of the target nucleic acid in cycle 2 of the first PCR amplification experiment, and wherein $$N_2 = N_0\left(1 + \frac{K}{K + N_0}\right)\left(1 + \frac{K}{K + N_0\left(1 + \frac{K}{K + N_0}\right)}\right).$$

4. The method of claim 1, wherein the first model further comprises an equation for $N_3$, the calculated amount of the target nucleic acid in cycle 3 of the first PCR amplification experiment, and wherein $$N_3 = N_0\left(1 + \frac{K}{K + N_0}\right)\left(1 + \frac{K}{K + N_0\left(1 + \frac{K}{K + N_0}\right)}\right)\left(1 + \frac{K}{K + N_0\left(1 + \frac{K}{K + N_0}\right)}\right).$$

5. The method of claim 1, the method further comprising:
(C) refining the first model by adjusting K and $N_0$ until differences between values $N_n$ computed by said first model and corresponding fluorescent measurements in the first plurality of fluorescent measurements are minimized, thereby calculating the initial amount of a target nucleic acid $N_0$ as the minimized value for $N_0$ for said first model.

6. The method of claim 5, wherein refinement of the first model by adjustment of K and $N_0$ comprises minimizing the sum of squares of a plurality of residuals $N_n-FS_n$ with respect to $N_0$ and K.

7. The method of claim 1, wherein the first PCR amplification experiment comprises cycles in a linear phase and cycles in an exponential phase, and wherein the first plurality of fluorescent measurements consists of fluorescent measurements taken from cycles in the exponential phase of the first PCR amplification experiment and cycles in the linear phase of the first PCR amplification experiment.

8. The method of claim 1, wherein the first plurality of fluorescent measurements consists of fluorescent measurements taken from a contiguous number of cycles in the first PCR amplification experiment, wherein the first cycle of the contiguous number of cycles in the first PCR amplification experiment is expressed as $n_{start}$ and the last cycle of the contiguous number of cycles in the first PCR amplification experiment is expressed as $n_{end}$.

9. The method of claim 8, wherein $n_{start}$ is the PCR cycle in the first PCR amplification experiment for which (i) the efficiency of all subsequent cycles in the first PCR amplification experiment consistently decreases, and (ii) the efficiency of the cycle $n_{start}+1$ of the first PCR amplification experiment is less than 1.05.

10. The method of claim 8, wherein $n_{end}$ is the first cycle in the first PCR amplification experiment where a second derivative of the observed fluorescent signal ($d^2FS/dn^2$) is less than zero.

11. The method of claim 1, wherein the first PCR amplification experiment comprises cycles in a linear phase, and wherein the first plurality of fluorescent measurements consists of between seven and twelve points in the measurable exponential and linear phase of the first PCR amplification experiment.

12. The method of claim 1, wherein
the receiving step (A) comprises receiving a plurality of fluorescent measurements for each PCR amplification experiment in a plurality of PCR amplification experiments, wherein the first PCR amplification experiment is in the plurality of PCR amplification experiments; and
the computing step (B) comprises computing a model in a plurality of models for each PCR amplification experiment in the plurality of PCR amplification experiments, wherein
for each respective model in the plurality of models, the respective model comprises a respective equation for $N_n$ for the corresponding fluorescent measurement n in the PCR amplification experiment corresponding to the respective model, wherein
(i) each $N_n$ in the respective model is the amount of target nucleic acid in cycle n of the PCR amplification experiment corresponding to the respective model from which the respective fluorescent measurement was taken,
(ii) each respective equation for $N_n$ in the respective model is expressed only in terms of $K_x$ and $N_0$, regardless of the cycle n of the corresponding fluorescent measurement in the corresponding PCR amplification experiment that is corresponding to the respective equation for $N_n$, wherein $K_x$ is the Michaelis-Menton constant for the corresponding PCR amplification experiment x, and (iii) each respective model comprises an equation for $N_n$, comprising $$N_n = N_0 + \sum_{k=0}^{n-1} \left( \frac{K_x}{K_x + N_k} \right).$$

13. The method of claim 12, the method further comprising:
(D) refining each respective model in the plurality of models by adjusting K and $N_0$ for each equation for $N_n$ in the respective model until differences between values $N_n$ computed by the respective model and corresponding fluorescent measurements in the plurality of fluorescent measurements of the PCR amplification experiment corresponding to the respective model are minimized, thereby calculating the initial amount of a target nucleic acid $N_0$ as the minimized value for $N_0$ for each respective model.

14. The method of claim 12, wherein each PCR amplification experiment in the plurality of PCR amplification experiments represents a serial dilution of the sample, the method further comprising:
(D) plotting $\log_{10}(N_0)$ of the initial amount of a target nucleic acid $N_0$ calculated for each model in the plurality of models as a function of relative concentration of the sample used in the PCR amplification experiment for each model in the plurality of models.

15. The method of claim 12, wherein each PCR amplification experiment in the plurality of PCR amplification experiments represents a serial dilution of the sample, the method further comprising:
(C) plotting the initial amount of a target nucleic acid $N_0$ calculated for each model in the plurality of models as a function of relative concentration of the sample used in the PCR amplification experiment for each model in the plurality of models.

16. The method of claim 12, wherein each PCR amplification experiment in the plurality of PCR amplification experiments represents a serial dilution of the sample, the method further comprising:
(C) refining the value $N_0$ calculated for each model in the plurality of models as a function of relative concentration of the sample so that a single refined value for $N_0$ is computed for the plurality of models.

17. The method of claim 16, wherein the refining step (C) comprises performing a weighted regression to minimize a mean absolute relative error (ARE) of a plurality of ARE values with respect to the value $N_0$ calculated by each model in the plurality of models, wherein $$ARE = \frac{\left| C_0^{actual} - C_0^{predicted} \right|}{C_0^{actual}}$$

each value in the plurality of ARE values is for a respective model in the plurality of models, and wherein $C_0^{actual}$ is the actual relative concentration of the sample used for the PCR amplification experiment corresponding to the respective model and $C_0^{predicted}$ is the calculated relative concentration of the sample used for the PCR amplification experiment corresponding to the respective model that is determined by the calculated value $N_0$ for the respective model.

18. The method of claim 12, wherein each PCR amplification experiment in the plurality of PCR amplification experiments represents a serial dilution of the sample, wherein the serial dilution is done in duplicate or triplicate and a different model is computed for each duplicate of each serial dilution or each triplicate of each serial dilution.

19. The method of claim 1, wherein
the receiving step (A) comprises receiving a plurality of fluorescent measurements for a second PCR amplification experiment using the sample; and
the computing step (B) comprises computing a second model for the second PCR amplification experiment, wherein, for each respective fluorescent measurement in the second plurality of fluorescent measurements, the second model comprises a respective equation for $N_n$, wherein
(i) $N_n$ is the calculated amount of target nucleic acid in cycle n of the second PCR amplification experiment from which the respective fluorescent measurement was taken,
(ii) the respective equation for $N_n$ in the second model is expressed only in terms of $K_2$ and $N_0$, regardless of the cycle n, wherein $K_2$ is the Michaelis-Menton constant for the second PCR amplification experiment, wherein for the second model, the equation for $N_n$ comprises $$N_n = N_0 + \sum_{k=0}^{n-1} \left( \frac{K_2}{K_2 + N_k} \right);$$

the method further comprising:
(C) calculating $N_0$ for the sample computed by the first model and $N_0$ for the sample computed by the second model;
(D) computing $$\rho = \frac{N_{AM}}{N_{BM}}$$

wherein,
$N_{AM}$ is the calculated $N_0$ for the sample computed by the first model; and
$N_{BM}$ is the calculated $N_0$ for the sample computed by the second model.

20. The method of claim 19, wherein the second model is refined during said computing step (B) by adjusting $K_2$ and $N_0$ until a difference between values $N_n$ computed by said second model and corresponding fluorescent measurements in the second plurality of fluorescent measurements are minimized.

21. The method of claim 19, wherein the first amplification experiment amplifies mRNA of a first gene and the second amplification experiment amplifies mRNA of a second gene and wherein,
$N_{AM}$ is a measure of an abundance of the mRNA of the first gene in the sample; and
$N_{BM}$ is a measure of an abundance of the mRNA of the second gene in the sample.

22. The method of claim 21, wherein the first gene is a gene associated with a phenotypic characterization and wherein the second gene is a gene that is not associated with the phenotypic characterization.

23. The method of claim 22, wherein, when $\rho$ is above a threshold value, the member of a species that contributed the sample is deemed to have the phenotypic characterization.

24. The method of claim 22, wherein, when $\rho$ is above a threshold value, the member of a species that contributed the sample is deemed to not have the phenotypic characterization.

25. The method of claim 22, wherein, when $\rho$ is below a threshold value, the member of a species that contributed the sample is deemed to have the phenotypic characterization.

26. The method of claim 22, wherein, when $\rho$ is below a threshold value, the member of a species that contributed the sample is deemed to not have the phenotypic characterization.

27. The method of claim 22, wherein the phenotypic characterization is a cell type, a cell morphology, a disease state, an abnormal state in a tissue or organ, an abnormal cell type, or an abnormal cell morphology.

28. The method of claim 22, wherein the phenotypic characterization is an indication that the test subject from which the sample was taken is likely to develop sepsis.

29. The method of claim 1, wherein the initial amount of a target nucleic acid $N_0$ in the sample is a concentration of the mRNA of a first gene in the sample.

30. The method of claim 1, wherein the initial amount of a target nucleic acid $N_0$ in the sample is a number of mRNA molecules transcribed from a first gene in the sample.

31. A method of determining whether a sample has a phenotypic characterization, the method comprising:
(A) calculating a first model for a first PCR amplification experiment comprising a first plurality of cycles, wherein
(i) the first PCR amplification experiment comprises a first plurality of fluorescent measurements,
(ii) each respective measurement in the first plurality of fluorescent measurements is taken from a different cycle in the first plurality of cycles of the first PCR amplification experiment,
(iii) the first PCR amplification experiment is a PCR amplification of a first gene in the sample,
(iv) the first model comprises a respective equation of an amount $N_n$ of the first gene for each cycle n in the first PCR amplification experiment,
(v) each respective equation for $N_n$ in the first model is expressed only in terms of $K_1$ and $N_{AM}$, regardless of the cycle n represented by the respective equation $N_n$, and wherein the equation for $N_n$ for the first model comprises the equation $$N_n = N_0 + \sum_{k=0}^{n-1} \left( \frac{K_1}{K_1 + N_k} \right),$$

(vi) $K_1$ is the Michaelis-Menton constant for the first PCR amplification experiment, and
(vii) $N_{AM}$ is the amount of the first gene in the sample prior to the first PCR amplification experiment of the sample; and
(B) calculating a second model for a second PCR amplification experiment comprising a second plurality of cycles, wherein
(i) the second PCR amplification experiment comprises a second plurality of fluorescent measurements,
(ii) each respective measurement in the second plurality of fluorescent measurements is taken from a different cycle in the second plurality of cycles of the second PCR amplification experiment, (iii) the second PCR amplification experiment is a PCR amplification of a second gene in the sample, (iv) the second model comprises a respective equation of an amount $N_n$ of the second gene for each cycle n in the second PCR amplification experiment, (v) each respective equation for $N_n$ in the second model is expressed only in terms of $K_2$ and $N_{BM}$, regardless of the cycle n represented by the respective equation $N_n$, and wherein the equation for $N_n$ for the second model comprises the equation $$N_n = N_0 + \sum_{k=0}^{n-1} \left( \frac{K_2}{K_2 + N_k} \right),$$

(vi) $K_2$ is the Michaelis-Menton constant for the second PCR amplification experiment, and (vii) $N_{BM}$ is the amount of the second gene in the sample prior to the second PCR amplification experiment of the sample; and (C) using the first model to calculate a value for $N_{AM}$ and the second model to calculate a value for $N_{BM}$; and (D) computing $$\rho = \frac{N_{AM}}{N_{BM}}; \text{ and}$$

(E) determining whether $\rho$ is above or below a threshold value, wherein the value computed for $\rho$ is indicative of whether the sample has the phenotypic characterization.

32. The method of claim 31, wherein step (A) further comprises calculating a plurality of first models, wherein each first model is a PCR amplification experiment of the first gene from a serial dilution of the sample and wherein $N_{AM}$ is taken as a measure of central tendency of the values $N_{AM}$ determined from each of the first models; and step (B) further comprises calculating a plurality of second models, wherein each second model is a PCR amplification experiment of the second gene from a serial dilution of the sample and wherein $N_{BM}$ is taken as a measure of central tendency of the values $N_{BM}$ determined from each of the second models.

33. The method of claim 32, wherein a first aliquot of the sample is used in the serial dilutions of step (A) and a second aliquot of the sample is used in the serial dilutions of step (B).

34. The method of claim 32, wherein the serial dilution of step (A) is done in duplicate or triplicate and a different first model is computed for each PCR amplification experiment of each dilution, for the first gene, and wherein $N_{AM}$ is deemed to be a measure of central tendency of the values $N_{AM}$ computed from each of the first models; and the serial dilution of step (B) is done in duplicate or triplicate and a different first model is computed for each PCR amplification experiment of each dilution, for the second gene, and wherein $N_{BM}$ is deemed to be a measure of central tendency of the values $N_{BM}$ computed from each of the second models.

35. The method of claim 32, wherein each PCR amplification experiment in the plurality of PCR amplification experiments represents a serial dilution of the sample, the method further comprising:

refining the value $N_{AM}$ calculated for each model in the plurality of first models as a function of relative concentration of the sample prior to said computing step (C); and refining the value $N_{BM}$ calculated for each model in the plurality of second models as a function of relative concentration of the sample prior to said computing step (C); wherein refinement of $N_{AM}$ comprises performing a weighted regression to minimize mean absolute relative error (ARE) of a plurality of ARE values with respect to $N_{AM}$ calculated by each of the first models, wherein each $$ARE = \frac{|C_0^{actual} - C_0^{predicted}|}{C_0^{actual}}$$

value in the plurality of ARE values is for a respective first model in the plurality of first models, and wherein $C_0^{actual}$ is the actual relative concentration of the sample used in a first PCR amplification experiment corresponding to the respective first model and $C_0^{predicted}$ is the calculated relative concentration of the sample used for the first PCR amplification experiment corresponding to the respective first model that is determined by the calculated value $N_{AM}$ for the respective first model; and refinement of $N_{BM}$ comprises performing a weighted regression to minimize mean absolute relative error (ARE) of a plurality of ARE values with respect to $N_{BM}$ calculated by each of the second models, wherein each $$ARE = \frac{|C_0^{actual} - C_0^{predicted}|}{C_0^{actual}}$$

value in the plurality of ARE values is for a respective second model in the plurality of second models, and wherein $C_0^{actual}$ is the actual relative concentration of the sample used in a second PCR amplification experiment corresponding to the respective second model and $C_0^{predicted}$ is the calculated relative concentration of the sample used for the second PCR amplification experiment corresponding to the respective second model that is determined by the calculated value $N_{AM}$ for the respective second model.

36. The method of claim 31, wherein $N_{AM}$ is a concentration of the mRNA for the first gene in the sample; and $N_{BM}$ is a concentration of the mRNA for the second gene in the sample.

37. The method of claim 31, wherein $N_{AM}$ is a number of mRNA molecules transcribed from the first gene in the sample; and $N_{BM}$ is a number of mRNA molecules transcribed from the second gene in the sample.

38. The method of claim 31, wherein the first amplification experiment amplifies mRNA of a first gene and the second amplification experiment amplifies mRNA of a second gene and wherein, $N_{AM}$ is a measure of an abundance of the mRNA of the first gene in the sample; and $N_{BM}$ is a measure of an abundance of the mRNA of the second gene in the sample.

39. The method of claim 31, wherein the first gene is a gene associated with a phenotypic characterization and wherein the second gene is a gene that is not associated with the phenotypic characterization.

40. The method of claim 39 wherein, when ρ is above a threshold value, the member of a species that contributed the sample is deemed to have the phenotypic characterization.

41. The method of claim 39 wherein, when ρ is above a threshold value, the member of a species that contributed the sample is deemed to not have the phenotypic characterization.

42. The method of claim 39 wherein, when ρ is below a threshold value, the member of a species that contributed the sample is deemed to have the phenotypic characterization.

43. The method of claim 39 wherein, when ρ is below a threshold value, the member of a species that contributed the sample is deemed to not have the phenotypic characterization.

44. The method of claim 39, wherein the phenotypic characterization is a cell type, a cell morphology, a disease state, an abnormal state in a tissue or organ, an abnormal cell type, or an abnormal cell morphology.

45. The method of claim 31, wherein the amount of the first gene in the sample prior to the first PCR amplification experiment of the sample is a concentration of the mRNA of the first gene in the sample.

46. The method of claim 31, wherein the amount of the first gene in the sample prior to the first PCR amplification experiment of the sample is a number of mRNA molecules transcribed from the first gene in the sample.

47. The method of claim 31, the method further comprising:
  (D) outputting ρ in user readable form to a user interface device, a monitor, a computer-readable storage medium, a computer-readable memory, or a local or remote computer system; or displaying ρ.

48. A polymerase chain reaction (PCR) system, comprising:
  a PCR analysis module that generates a plurality of fluorescent measurements, wherein each respective fluorescent measurement $FS_n$ in the plurality of fluorescent measurements is a fluorescent measurement taken in a different cycle n in a PCR amplification experiment of a sample; and
  an intelligence module adapted to process the plurality of fluorescent measurements by computing a model for the PCR amplification experiment that provides a calculated initial amount of the target nucleic acid $N_0$ in the sample, wherein, for each respective fluorescent measurement in the plurality of fluorescent measurements, the intelligence model comprises a respective equation for $N_n$, wherein
    (i) $N_n$ is the calculated amount of the target nucleic acid in cycle n of the PCR amplification experiment from which the respective fluorescent measurement was taken, and
    (ii) the respective equation for $N_n$ is expressed only in terms of K and $N_0$, regardless of the cycle n of the PCR amplification experiment, wherein K is the Michaelis-Menton constant for the PCR amplification experiment, wherein the equation for $N_n$ comprises $$N_n = N_0 + \sum_{k=0}^{n-1} \left( \frac{K}{K + N_k} \right).$$

49. The PCR system of claim 48, wherein the intelligence module comprises instructions for adjusting K and $N_0$ until differences between values $N_n$ computed by said model and corresponding fluorescent measurements in the plurality of fluorescent measurements are minimized, thereby determining the calculated initial amount of the target nucleic acid $N_0$ in the sample.

50. The PCR system of claim 48, wherein the intelligence module further comprises instructions for outputting $N_0$ to a user interface device, a monitor, a computer-readable storage medium, a computer-readable memory, or a local or remote computer system; or displaying $N_0$.

51. A computer system for calculating an initial amount of a target nucleic acid $N_0$ in a sample, the computer system comprising a processor and a memory, coupled to the processor, the memory storing a module comprising:
  (A) instructions for receiving a plurality of fluorescent measurements, wherein each respective fluorescent measurement $FS_n$ in the plurality of fluorescent measurements is a fluorescent measurement taken in a different cycle n in a PCR amplification experiment of the sample; and
  (B) instructions for computing a model for the PCR amplification experiment that provides a calculated initial amount of the target nucleic acid $N_0$ in the sample, wherein, for each respective fluorescent measurement in the plurality of fluorescent measurements, the model comprises a respective equation for $N_n$, wherein
    (i) $N_n$ is the calculated amount of the target nucleic acid in cycle n of the PCR amplification experiment from which the respective fluorescent measurement was taken, and
    (ii) the respective equation for $N_n$ is expressed only in terms of K and $N_0$, regardless of the cycle n of the PCR amplification experiment, wherein K is the Michaelis-Menton constant for the PCR amplification experiment, wherein the equation for $N_n$ comprises $$N_n = N_0 + \sum_{k=0}^{n-1} \left( \frac{K}{K + N_k} \right).$$

52. The computer system of claim 51, wherein the instructions for computing the model include instructions for refining the model by adjusting K and $N_0$ until differences between values $N_n$ computed by said model and corresponding fluorescent measurements in the plurality of fluorescent measurements are minimized, thereby calculating the calculated initial amount of a target nucleic acid $N_0$ as the minimized value for $N_0$ for said model.

53. The computer system of claim 51, wherein the module further comprises instructions for outputting the calculated initial amount of a target nucleic acid $N_0$ calculated by said instructions for computing (B) to a user interface device, a monitor, a computer-readable storage medium, a computer-readable memory, or a local or remote computer system; or displaying the calculated initial amount of a target nucleic acid $N_0$ calculated by said instructions for computing (B).

54. A non-transitory computer-readable medium storing a computer program, executable by a computer, to calculate an initial amount of a target nucleic acid $N_0$ in a sample, wherein the computer program comprises:
  (A) instructions for receiving a plurality of fluorescent measurements, wherein each respective fluorescent measurement $FS_n$ in the plurality of fluorescent measurements is a fluorescent measurement taken in a different cycle n in a PCR amplification experiment of the sample; and
  (B) instructions for computing a model for the PCR amplification experiment that provides a calculated initial amount of the target nucleic acid $N_0$ in the sample, wherein, for each respective fluorescent measurement in the plurality of fluorescent measurements, the model comprises a respective equation for $N_n$, wherein (i) $N_n$ is the calculated amount of the target nucleic acid in cycle n of the PCR amplification experiment from which the respective fluorescent measurement was taken, and (ii) the respective equation for $N_n$ is expressed only in terms of K and $N_0$, regardless of the cycle n of the PCR amplification experiment, wherein K is the Michaelis-Menton constant for the PCR amplification experiment, wherein the equation for $N_n$ comprises $$N_n = N_0 + \sum_{k=0}^{n-1}\left(\frac{K}{K+N_k}\right).$$

55. The non-transitory computer-readable medium of claim 54, wherein the instructions for computing further comprise refining the model by adjusting K and $N_0$ until differences between values $N_n$ computed by the model and corresponding fluorescent measurements in the plurality of fluorescent measurements are minimized, thereby calculating the initial amount of a target nucleic acid $N_0$ as the minimized value for $N_0$ for said model.

56. The non-transitory computer-readable medium of claim 54, wherein the computer program product further comprises instructions for outputting the calculated initial amount of a target nucleic acid $N_0$ calculated by said instructions for computing (B) in user readable form to a user interface device, a monitor, a computer-readable storage medium, a computer-readable memory, or a local or remote computer system; or displaying the calculated initial amount of a target nucleic acid $N_0$ calculated in said instructions for computing (B).

* * * * *